US012789046B2

(12) United States Patent
Ashley et al.

(10) Patent No.: US 12,789,046 B2
(45) Date of Patent: Nov. 10, 2026

(54) SYSTEM AND METHOD FOR GENERATING TREATMENT PLANS TO ENHANCE PATIENT RECOVERY BASED ON SPECIFIC OCCUPATIONS

(71) Applicant: ROM TECHNOLOGIES, INC., Brookfield, CT (US)

(72) Inventors: John Ashley, San Francisco, CA (US); Steven Mason, Las Vegas, NV (US)

(73) Assignee: ROM Technologies, Inc., Brookfield, CT (US)

(*) Notice: Subject to any disclaimer, the term of this patent is extended or adjusted under 35 U.S.C. 154(b) by 845 days.

(21) Appl. No.: 17/827,380

(22) Filed: May 27, 2022

(65) Prior Publication Data

US 2022/0288462 A1 Sep. 15, 2022

Related U.S. Application Data

(63) Continuation-in-part of application No. 17/739,906, filed on May 9, 2022, now Pat. No. 12,558,594, (Continued)

(51) Int. Cl.
*A63B 24/00* (2006.01)
*A63B 21/005* (2006.01)
(Continued)

(52) U.S. Cl.
CPC ...... *A63B 24/0075* (2013.01); *A63B 21/0058* (2013.01); *A63B 24/0062* (2013.01);
(Continued)

(58) Field of Classification Search
CPC ............ A63B 24/0075; A63B 21/0058; A63B 24/0062; A63B 22/0605; A63B 2024/0093; G16H 20/30; G06N 20/00
See application file for complete search history.

(56) References Cited

U.S. PATENT DOCUMENTS

| | | | |
|---|---|---|---|
| 823,712 | A | 6/1906 | Uhlmann |
| 4,499,900 | A | 2/1985 | Petrofsky et al. |

(Continued)

FOREIGN PATENT DOCUMENTS

| | | | |
|---|---|---|---|
| CA | 3193419 | A1 | 3/2022 |
| CN | 2885238 | Y | 4/2007 |

(Continued)

OTHER PUBLICATIONS

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

(Continued)

*Primary Examiner* — Vincent H Tran
(74) *Attorney, Agent, or Firm* — Dickinson Wright PLLC; Stephen A. Mason; Jonathan H. Harder

(57) ABSTRACT

A method is disclosed for generating a treatment plan to modify an attribute of a user, wherein the attribute of the user is associated with an attribute of an occupational task. The method includes receiving data associated with the user, wherein the data comprises the modified attribute of the user and the attribute of the occupational task; accessing a database comprising data associated with exercises associated with the modified attribute of the user and the attribute of the occupational task; and generating, via an artificial intelligence engine, the treatment plan comprising an exercise of the exercises associated with the modified attribute of the first user and the attribute of the occupational task, wherein the artificial intelligence engine generates the treatment plan comprising the exercise based on the data associated with the user and the data associated with the exercises.

18 Claims, 14 Drawing Sheets

Related U.S. Application Data which is a continuation of application No. 17/150,938, filed on Jan. 15, 2021, now Pat. No. 11,325,005, which is a continuation-in-part of application No. 17/021,895, filed on Sep. 15, 2020, now Pat. No. 11,071,597.

(60) Provisional application No. 63/194,684, filed on May 28, 2021, provisional application No. 63/066,488, filed on Aug. 17, 2020, provisional application No. 62/910,232, filed on Oct. 3, 2019.

(51) Int. Cl.
*G06N 20/00* (2019.01)
*G16H 10/60* (2018.01)
*G16H 20/30* (2018.01)
*A63B 22/00* (2006.01)
*A63B 22/06* (2006.01)

(52) U.S. Cl.
CPC ............. *G06N 20/00* (2019.01); *G16H 10/60* (2018.01); *G16H 20/30* (2018.01); *A63B 2022/0094* (2013.01); *A63B 22/0605* (2013.01); *A63B 2024/0093* (2013.01)

(56) References Cited

U.S. PATENT DOCUMENTS

| | | | |
|---|---|---|---|
| 4,822,032 | A | 4/1989 | Whitmore et al. |
| 4,860,763 | A | 8/1989 | Schminke |
| 4,869,497 | A | 9/1989 | Stewart et al. |
| 4,932,650 | A | 6/1990 | Bingham et al. |
| 5,137,501 | A | 8/1992 | Mertesdorf |
| 5,161,430 | A | 11/1992 | Febey |
| 5,202,794 | A | 4/1993 | Schnee et al. |
| 5,240,417 | A | 8/1993 | Smithson et al. |
| 5,247,853 | A | 9/1993 | Dalebout |
| 5,256,117 | A | 10/1993 | Potts et al. |
| D342,299 | S | 12/1993 | Birrell et al. |
| 5,282,748 | A | 2/1994 | Little |
| 5,284,131 | A | 2/1994 | Gray |
| 5,316,532 | A | 5/1994 | Butler |
| 5,318,487 | A | 6/1994 | Golen |
| 5,324,241 | A | 6/1994 | Artigues et al. |
| 5,336,147 | A | 8/1994 | Sweeney, III |
| 5,338,272 | A | 8/1994 | Sweeney, III |
| 5,356,356 | A | 10/1994 | Hildebrandt |
| 5,361,649 | A | 11/1994 | Slocum, Jr. |
| D359,777 | S | 6/1995 | Hildebrandt |
| 5,429,140 | A | 7/1995 | Burdea et al. |
| 5,458,022 | A | 10/1995 | Mattfeld et al. |
| 5,487,713 | A | 1/1996 | Butler |
| 5,566,589 | A | 10/1996 | Buck |
| 5,580,338 | A | 12/1996 | Scelta et al. |
| 5,676,349 | A | 10/1997 | Wilson |
| 5,685,804 | A | 11/1997 | Whan-Tong et al. |
| 5,738,636 | A | 4/1998 | Saringer et al. |
| 5,860,941 | A | 1/1999 | Saringer et al. |
| 5,950,813 | A | 9/1999 | Hoskins et al. |
| 6,007,459 | A | 12/1999 | Burgess |
| D421,075 | S | 2/2000 | Hildebrandt |
| 6,053,847 | A | 4/2000 | Stearns et al. |
| 6,077,201 | A | 6/2000 | Cheng |
| 6,102,834 | A | 8/2000 | Chen |
| 6,110,130 | A | 8/2000 | Kramer |
| 6,155,958 | A | 12/2000 | Goldberg |
| 6,162,189 | A | 12/2000 | Girone et al. |
| 6,182,029 | B1 | 1/2001 | Friedman |
| D438,580 | S | 3/2001 | Shaw |
| 6,253,638 | B1 | 7/2001 | Bermudez |
| 6,267,735 | B1 | 7/2001 | Blanchard et al. |
| 6,273,863 | B1 | 8/2001 | Avni et al. |
| D450,100 | S | 11/2001 | Hsu |
| D450,101 | S | 11/2001 | Hsu |
| D451,972 | S | 12/2001 | Easley |
| D452,285 | S | 12/2001 | Easley |
| D454,605 | S | 3/2002 | Lee |
| 6,371,891 | B1 | 4/2002 | Speas |
| D459,776 | S | 7/2002 | Lee |
| 6,413,190 | B1 | 7/2002 | Wood et al. |
| 6,430,436 | B1 | 8/2002 | Richter |
| 6,436,058 | B1 | 8/2002 | Krahner et al. |
| 6,450,923 | B1 | 9/2002 | Vatti |
| 6,474,193 | B1 | 11/2002 | Farney |
| 6,491,649 | B1 | 12/2002 | Ombrellaro |
| 6,514,085 | B2 | 2/2003 | Slattery et al. |
| 6,535,861 | B1 | 3/2003 | OConnor et al. |
| 6,543,309 | B2 | 4/2003 | Heim |
| 6,589,139 | B1 | 7/2003 | Butterworth |
| 6,601,016 | B1 | 7/2003 | Brown et al. |
| 6,602,191 | B2 | 8/2003 | Quy |
| 6,613,000 | B1 | 9/2003 | Reinkensmeyer et al. |
| 6,626,800 | B1 | 9/2003 | Casler |
| 6,626,805 | B1 | 9/2003 | Lightbody |
| 6,640,122 | B2 | 10/2003 | Manoli |
| 6,640,662 | B1 | 11/2003 | Baxter |
| 6,652,425 | B1 | 11/2003 | Martin et al. |
| 6,659,946 | B1 | 12/2003 | Batchelor et al. |
| 6,820,517 | B1 | 11/2004 | Farney |
| 6,865,969 | B2 | 3/2005 | Stevens |
| 6,890,312 | B1 | 5/2005 | Priester et al. |
| 6,895,834 | B1 | 5/2005 | Baatz |
| 6,902,513 | B1 | 6/2005 | McClure |
| 7,058,453 | B2 | 6/2006 | Nelson et al. |
| 7,063,643 | B2 | 6/2006 | Arai |
| 7,156,665 | B1 | 1/2007 | OConnor et al. |
| 7,156,780 | B1 | 1/2007 | Fuchs et al. |
| 7,169,085 | B1 | 1/2007 | Killin et al. |
| 7,204,788 | B2 | 4/2007 | Andrews |
| 7,209,886 | B2 | 4/2007 | Kimmel |
| 7,226,394 | B2 | 6/2007 | Johnson |
| RE39,904 | E | 10/2007 | Lee |
| 7,406,003 | B2 | 7/2008 | Burkhardt et al. |
| 7,507,188 | B2 | 3/2009 | Nurre |
| 7,594,879 | B2 | 9/2009 | Johnson |
| 7,628,730 | B1 | 12/2009 | Watterson et al. |
| D610,635 | S | 2/2010 | Hildebrandt |
| 7,778,851 | B2 | 8/2010 | Schoenberg et al. |
| 7,809,601 | B2 | 10/2010 | Shaya et al. |
| 7,815,551 | B2 | 10/2010 | Merli |
| 7,833,135 | B2 | 11/2010 | Radow et al. |
| 7,837,472 | B1 | 11/2010 | Elsmore et al. |
| 7,890,342 | B1 | 2/2011 | Yruko |
| 7,955,219 | B2 | 6/2011 | Birrell et al. |
| 7,969,315 | B1 | 6/2011 | Ross et al. |
| 7,988,599 | B2 | 8/2011 | Ainsworth et al. |
| 8,012,107 | B2 | 9/2011 | Einav et al. |
| 8,021,270 | B2 | 9/2011 | D'Eredita |
| 8,038,578 | B2 | 10/2011 | Olrik et al. |
| 8,079,937 | B2 | 12/2011 | Bedell |
| 8,113,991 | B2 | 2/2012 | Kutliroff |
| 8,172,724 | B2 | 5/2012 | Solomon |
| 8,177,732 | B2 | 5/2012 | Einav et al. |
| 8,287,434 | B2 | 10/2012 | Zavadsky et al. |
| 8,298,123 | B2 | 10/2012 | Hickman |
| 8,371,990 | B2 | 2/2013 | Shea |
| 8,419,593 | B2 | 4/2013 | Ainsworth et al. |
| 8,465,398 | B2 | 6/2013 | Lee et al. |
| 8,503,086 | B2 | 8/2013 | French |
| 8,506,458 | B2 | 8/2013 | Dugan |
| 8,515,777 | B1 | 8/2013 | Rajasenan |
| 8,540,515 | B2 | 9/2013 | Williams et al. |
| 8,540,516 | B2 | 9/2013 | Williams et al. |
| 8,556,778 | B1 | 10/2013 | Dugan |
| 8,607,465 | B1 | 12/2013 | Edwards |
| 8,613,689 | B2 | 12/2013 | Dyer et al. |
| 8,615,529 | B2 | 12/2013 | Reiner |
| 8,672,812 | B2 | 3/2014 | Dugan |
| 8,751,264 | B2 | 6/2014 | Beraja et al. |
| 8,784,273 | B2 | 7/2014 | Dugan |
| 8,818,496 | B2 | 8/2014 | Dziubinski et al. |
| 8,823,448 | B1 | 9/2014 | Shen |
| 8,845,493 | B2 | 9/2014 | Watterson et al. |

(56) References Cited

U.S. PATENT DOCUMENTS

| | | | |
|---|---|---|---|
| 8,849,681 B2 | 9/2014 | Hargrove et al. | |
| 8,864,628 B2 | 10/2014 | Boyette et al. | |
| 8,893,287 B2 | 11/2014 | Gjonej et al. | |
| 8,911,327 B1 | 12/2014 | Boyette | |
| 8,979,711 B2 | 3/2015 | Dugan | |
| 9,004,598 B2 | 4/2015 | Weber | |
| 9,044,630 B1 | 6/2015 | Lampert et al. | |
| 9,167,281 B2 | 10/2015 | Petrov et al. | |
| D744,050 S | 11/2015 | Colburn | |
| 9,248,071 B1 | 2/2016 | Brenda | |
| 9,256,711 B2 * | 2/2016 | Horseman | G16H 40/63 |
| 9,272,091 B2 | 3/2016 | Skelton | |
| 9,272,185 B2 | 3/2016 | Dugan | |
| 9,283,434 B1 | 3/2016 | Wu | |
| 9,295,878 B2 | 3/2016 | Corbalis et al. | |
| 9,311,789 B1 | 4/2016 | Gwin | |
| 9,312,907 B2 | 4/2016 | Auchinleck et al. | |
| 9,367,668 B2 | 6/2016 | Flynt et al. | |
| 9,409,054 B2 | 8/2016 | Dugan | |
| 9,443,205 B2 | 9/2016 | Wall | |
| 9,474,935 B2 | 10/2016 | Abbondanza et al. | |
| 9,480,873 B2 | 11/2016 | Chuang | |
| 9,481,428 B2 | 11/2016 | Gros | |
| 9,514,277 B2 | 12/2016 | Hassing et al. | |
| 9,566,472 B2 | 2/2017 | Dugan | |
| 9,579,056 B2 | 2/2017 | Rosenbek et al. | |
| 9,629,558 B2 | 4/2017 | Yuen et al. | |
| 9,640,057 B1 | 5/2017 | Ross | |
| 9,707,147 B2 | 7/2017 | Levital et al. | |
| 9,713,744 B2 | 7/2017 | Suzuki | |
| D794,142 S | 8/2017 | Zhou | |
| 9,717,947 B2 | 8/2017 | Lin | |
| 9,737,761 B1 | 8/2017 | Govindarajan | |
| 9,757,612 B2 | 9/2017 | Weber | |
| 9,773,330 B1 | 9/2017 | Douglas | |
| 9,782,621 B2 | 10/2017 | Chiang et al. | |
| 9,802,076 B2 | 10/2017 | Murray et al. | |
| 9,802,081 B2 | 10/2017 | Ridgel et al. | |
| 9,813,239 B2 | 11/2017 | Chee et al. | |
| 9,827,445 B2 | 11/2017 | Marcos et al. | |
| 9,849,337 B2 | 12/2017 | Roman et al. | |
| 9,868,028 B2 | 1/2018 | Shin | |
| 9,872,087 B2 | 1/2018 | DelloStritto et al. | |
| 9,872,637 B2 | 1/2018 | Kording et al. | |
| 9,914,053 B2 | 3/2018 | Dugan | |
| 9,919,198 B2 | 3/2018 | Romeo et al. | |
| 9,937,382 B2 | 4/2018 | Dugan | |
| 9,939,784 B1 | 4/2018 | Berardinelli | |
| 9,974,478 B1 | 5/2018 | Brokaw | |
| 9,977,587 B2 | 5/2018 | Mountain | |
| 9,993,181 B2 | 6/2018 | Ross | |
| 9,997,082 B2 | 6/2018 | Kaleal | |
| 10,004,946 B2 | 6/2018 | Ross | |
| 10,026,052 B2 | 7/2018 | Brown et al. | |
| D826,349 S | 8/2018 | Oblamski | |
| 10,055,550 B2 | 8/2018 | Goetz | |
| 10,058,473 B2 | 8/2018 | Oshima et al. | |
| 10,074,148 B2 | 9/2018 | Cashman et al. | |
| 10,089,443 B2 | 10/2018 | Miller et al. | |
| 10,111,643 B2 | 10/2018 | Shulhauser et al. | |
| 10,130,311 B1 | 11/2018 | De Sapio et al. | |
| 10,137,328 B2 | 11/2018 | Baudhuin | |
| 10,143,395 B2 | 12/2018 | Chakravarthy et al. | |
| 10,155,134 B2 | 12/2018 | Dugan | |
| 10,159,872 B2 | 12/2018 | Sasaki et al. | |
| 10,173,094 B2 | 1/2019 | Gomberg | |
| 10,173,095 B2 | 1/2019 | Gomberg et al. | |
| 10,173,096 B2 | 1/2019 | Gomberg et al. | |
| 10,173,097 B2 | 1/2019 | Gomberg et al. | |
| 10,198,928 B1 | 2/2019 | Ross et al. | |
| 10,226,663 B2 | 3/2019 | Gomberg et al. | |
| 10,231,664 B2 | 3/2019 | Ganesh | |
| 10,244,990 B2 | 4/2019 | Hu et al. | |
| 10,258,823 B2 | 4/2019 | Cole | |
| 10,322,315 B2 | 6/2019 | Foley et al. | |
| 10,325,070 B2 | 6/2019 | Beale et al. | |
| 10,327,697 B1 | 6/2019 | Stein et al. | |
| 10,362,940 B2 | 7/2019 | Tran | |
| 10,369,021 B2 | 8/2019 | Zoss et al. | |
| 10,380,866 B1 | 8/2019 | Ross et al. | |
| 10,413,222 B1 | 9/2019 | Kayyall | |
| 10,413,238 B1 | 9/2019 | Cooper | |
| 10,424,033 B2 | 9/2019 | Romeo | |
| 10,430,552 B2 | 10/2019 | Mihai | |
| D866,957 S | 11/2019 | Ross et al. | |
| 10,468,131 B2 | 11/2019 | Macoviak et al. | |
| 10,475,323 B1 | 11/2019 | Ross | |
| 10,475,537 B2 | 11/2019 | Purdie et al. | |
| 10,492,977 B2 | 12/2019 | Kapure et al. | |
| 10,507,358 B2 | 12/2019 | Kinnunen et al. | |
| 10,542,914 B2 | 1/2020 | Forth et al. | |
| 10,546,467 B1 | 1/2020 | Luciano, Jr. et al. | |
| 10,569,122 B2 | 2/2020 | Johnson | |
| 10,572,626 B2 | 2/2020 | Balram | |
| 10,576,331 B2 | 3/2020 | Kuo | |
| 10,581,896 B2 | 3/2020 | Nachenberg | |
| 10,625,114 B2 | 4/2020 | Ercanbrack | |
| 10,646,746 B1 | 5/2020 | Gomberg et al. | |
| 10,660,534 B2 | 5/2020 | Lee et al. | |
| 10,678,890 B2 | 6/2020 | Bitran et al. | |
| 10,685,092 B2 | 6/2020 | Paparella et al. | |
| 10,741,285 B2 | 8/2020 | Moturu | |
| 10,777,200 B2 | 9/2020 | Will et al. | |
| D899,605 S | 10/2020 | Ross et al. | |
| 10,792,495 B2 | 10/2020 | Zvorski et al. | |
| 10,814,170 B2 | 10/2020 | Wang et al. | |
| 10,857,426 B1 | 12/2020 | Neumann | |
| 10,867,695 B2 | 12/2020 | Neagle | |
| 10,874,905 B2 | 12/2020 | Belson et al. | |
| D907,143 S | 1/2021 | Ach et al. | |
| 10,881,911 B2 | 1/2021 | Kwon et al. | |
| 10,902,944 B1 | 1/2021 | Casey | |
| 10,918,332 B2 | 2/2021 | Belson et al. | |
| 10,931,643 B1 | 2/2021 | Neumann | |
| 10,987,176 B2 | 4/2021 | Poltaretskyi et al. | |
| 10,991,463 B2 | 4/2021 | Kutzko et al. | |
| 11,000,735 B2 | 5/2021 | Orady et al. | |
| 11,045,709 B2 | 6/2021 | Putnam | |
| 11,065,170 B2 | 7/2021 | Yang et al. | |
| 11,065,527 B2 | 7/2021 | Putnam | |
| 11,069,436 B2 | 7/2021 | Mason et al. | |
| 11,071,597 B2 | 7/2021 | Posnack et al. | |
| 11,075,000 B2 | 7/2021 | Mason et al. | |
| D928,635 S | 8/2021 | Hacking et al. | |
| 11,087,865 B2 | 8/2021 | Mason et al. | |
| 11,094,400 B2 | 8/2021 | Riley et al. | |
| 11,101,028 B2 | 8/2021 | Mason et al. | |
| 11,107,591 B1 | 8/2021 | Mason | |
| 11,139,060 B2 | 10/2021 | Mason et al. | |
| 11,185,735 B2 | 11/2021 | Arn et al. | |
| 11,185,738 B1 | 11/2021 | McKirdy et al. | |
| D939,096 S | 12/2021 | Lee | |
| D939,644 S | 12/2021 | Ach et al. | |
| D940,797 S | 1/2022 | Ach et al. | |
| D940,891 S | 1/2022 | Lee | |
| 11,229,727 B2 | 1/2022 | Tatonetti | |
| 11,229,788 B1 | 1/2022 | John | |
| 11,265,234 B2 | 3/2022 | Guaneri et al. | |
| 11,270,795 B2 | 3/2022 | Mason et al. | |
| 11,272,879 B2 | 3/2022 | Wiedenhoefer et al. | |
| 11,278,766 B2 | 3/2022 | Lee | |
| 11,282,599 B2 | 3/2022 | Mason et al. | |
| 11,282,604 B2 | 3/2022 | Mason et al. | |
| 11,282,608 B2 | 3/2022 | Mason et al. | |
| 11,284,797 B2 | 3/2022 | Mason et al. | |
| D948,639 S | 4/2022 | Ach et al. | |
| 11,295,848 B2 | 4/2022 | Mason et al. | |
| 11,298,284 B2 | 4/2022 | Bayerlein | |
| 11,309,085 B2 | 4/2022 | Mason et al. | |
| 11,317,975 B2 | 5/2022 | Mason et al. | |
| 11,325,005 B2 | 5/2022 | Mason et al. | |
| 11,328,807 B2 | 5/2022 | Mason et al. | |
| 11,337,648 B2 | 5/2022 | Mason | |
| 11,347,829 B1 | 5/2022 | Sclar et al. | |

(56) References Cited

U.S. PATENT DOCUMENTS

| | | | |
|---|---|---|---|
| 11,348,683 | B2 | 5/2022 | Guaneri et al. |
| 11,370,328 | B2 | 6/2022 | Main |
| 11,376,470 | B2 | 7/2022 | Weldemariam |
| 11,404,150 | B2 | 8/2022 | Guaneri et al. |
| 11,410,768 | B2 | 8/2022 | Mason et al. |
| 11,422,841 | B2 | 8/2022 | Jeong |
| 11,437,137 | B1 | 9/2022 | Harris |
| 11,495,355 | B2 | 11/2022 | McNutt et al. |
| 11,508,258 | B2 | 11/2022 | Nakashima et al. |
| 11,508,482 | B2 | 11/2022 | Mason et al. |
| 11,515,021 | B2 | 11/2022 | Mason |
| 11,515,028 | B2 | 11/2022 | Mason |
| 11,524,210 | B2 | 12/2022 | Kim et al. |
| 11,527,326 | B2 | 12/2022 | McNair et al. |
| 11,532,402 | B2 | 12/2022 | Farley et al. |
| 11,534,654 | B2 | 12/2022 | Silcock et al. |
| D976,339 | S | 1/2023 | Li |
| 11,541,274 | B2 | 1/2023 | Hacking |
| 11,553,969 | B1 | 1/2023 | Lang et al. |
| 11,621,067 | B1 | 4/2023 | Nolan |
| 11,636,944 | B2 | 4/2023 | Hanrahan et al. |
| 11,654,327 | B2 | 5/2023 | Phillips et al. |
| 11,663,673 | B2 | 5/2023 | Pyles |
| 11,673,024 | B2 | 6/2023 | Omid-Zohoor |
| 11,701,548 | B2 | 7/2023 | Posnack et al. |
| 11,776,676 | B2 | 10/2023 | Savolainen |
| 11,944,579 | B2 | 4/2024 | Sankai |
| 11,957,960 | B2 | 4/2024 | Bissonnette et al. |
| 12,004,871 | B1 * | 6/2024 | Fazeli .................. A61B 5/0064 |
| 12,020,511 | B1 | 6/2024 | Denton et al. |
| 12,057,210 | B2 | 8/2024 | Akinola et al. |
| 12,205,704 | B2 | 1/2025 | Hosoi et al. |
| 2001/0044573 | A1 | 11/2001 | Manoli |
| 2002/0010596 | A1 | 1/2002 | Matory |
| 2002/0072452 | A1 | 6/2002 | Torkelson |
| 2002/0143279 | A1 | 10/2002 | Porter et al. |
| 2002/0160883 | A1 | 10/2002 | Dugan |
| 2002/0183599 | A1 | 12/2002 | Castellanos |
| 2003/0013072 | A1 | 1/2003 | Thomas |
| 2003/0036683 | A1 | 2/2003 | Kehr et al. |
| 2003/0064860 | A1 | 4/2003 | Yamashita et al. |
| 2003/0064863 | A1 | 4/2003 | Chen |
| 2003/0083596 | A1 | 5/2003 | Kramer et al. |
| 2003/0092536 | A1 | 5/2003 | Romanelli et al. |
| 2003/0181832 | A1 | 9/2003 | Carnahan et al. |
| 2004/0072652 | A1 | 4/2004 | Alessandri et al. |
| 2004/0102931 | A1 | 5/2004 | Ellis et al. |
| 2004/0106502 | A1 | 6/2004 | Sher |
| 2004/0147969 | A1 | 7/2004 | Mann et al. |
| 2004/0172093 | A1 | 9/2004 | Rummerfield |
| 2004/0194572 | A1 | 10/2004 | Kim |
| 2004/0197727 | A1 | 10/2004 | Sachdeva et al. |
| 2004/0204959 | A1 | 10/2004 | Moreano et al. |
| 2005/0015118 | A1 | 1/2005 | Davis et al. |
| 2005/0020411 | A1 | 1/2005 | Andrews |
| 2005/0043153 | A1 | 2/2005 | Krietzman |
| 2005/0049122 | A1 | 3/2005 | Vallone et al. |
| 2005/0085346 | A1 | 4/2005 | Johnson |
| 2005/0085353 | A1 | 4/2005 | Johnson |
| 2005/0115561 | A1 | 6/2005 | Stahmann |
| 2005/0143641 | A1 | 6/2005 | Tashiro |
| 2005/0274220 | A1 | 12/2005 | Reboullet |
| 2006/0003871 | A1 | 1/2006 | Houghton et al. |
| 2006/0046905 | A1 | 3/2006 | Doody, Jr. et al. |
| 2006/0058648 | A1 | 3/2006 | Meier |
| 2006/0064136 | A1 | 3/2006 | Wang |
| 2006/0064329 | A1 | 3/2006 | Abolfathi et al. |
| 2006/0129432 | A1 | 6/2006 | Choi et al. |
| 2006/0199700 | A1 | 9/2006 | LaStayo et al. |
| 2006/0247095 | A1 | 11/2006 | Rummerfield |
| 2006/0277074 | A1 | 12/2006 | Einav |
| 2007/0042868 | A1 | 2/2007 | Fisher et al. |
| 2007/0118389 | A1 | 5/2007 | Shipon |
| 2007/0118406 | A1 | 5/2007 | Killin et al. |
| 2007/0137307 | A1 | 6/2007 | Gruben et al. |
| 2007/0173392 | A1 | 7/2007 | Stanford |
| 2007/0184414 | A1 | 8/2007 | Perez |
| 2007/0194939 | A1 | 8/2007 | Alvarez et al. |
| 2007/0219059 | A1 | 9/2007 | Schwartz |
| 2007/0271065 | A1 | 11/2007 | Gupta et al. |
| 2007/0287597 | A1 | 12/2007 | Cameron |
| 2008/0021834 | A1 | 1/2008 | Holla et al. |
| 2008/0077619 | A1 | 3/2008 | Gilley et al. |
| 2008/0082356 | A1 | 4/2008 | Friedlander et al. |
| 2008/0096726 | A1 | 4/2008 | Riley et al. |
| 2008/0103023 | A1 | 5/2008 | Chung |
| 2008/0153592 | A1 | 6/2008 | James-Herbert |
| 2008/0161166 | A1 | 7/2008 | Lo |
| 2008/0161733 | A1 | 7/2008 | Einav et al. |
| 2008/0183500 | A1 | 7/2008 | Banigan |
| 2008/0281633 | A1 | 11/2008 | Burdea et al. |
| 2008/0300914 | A1 | 12/2008 | Karkanias et al. |
| 2008/0312040 | A1 | 12/2008 | Ochi |
| 2009/0011907 | A1 | 1/2009 | Radow et al. |
| 2009/0037334 | A1 | 2/2009 | Hsu |
| 2009/0058635 | A1 | 3/2009 | LaLonde et al. |
| 2009/0070138 | A1 | 3/2009 | Langheier et al. |
| 2009/0157617 | A1 | 6/2009 | Herlocker |
| 2009/0211395 | A1 | 8/2009 | Mule |
| 2009/0270227 | A1 | 10/2009 | Ashby et al. |
| 2009/0287503 | A1 | 11/2009 | Angell et al. |
| 2009/0299766 | A1 | 12/2009 | Friedlander et al. |
| 2010/0048358 | A1 | 2/2010 | Tchao et al. |
| 2010/0062818 | A1 | 3/2010 | Haughay, Jr |
| 2010/0076786 | A1 | 3/2010 | Dalton et al. |
| 2010/0121160 | A1 | 5/2010 | Stark et al. |
| 2010/0173747 | A1 | 7/2010 | Chen et al. |
| 2010/0216168 | A1 | 8/2010 | Heinzman et al. |
| 2010/0234184 | A1 | 9/2010 | Le Page et al. |
| 2010/0248899 | A1 | 9/2010 | Bedell et al. |
| 2010/0248905 | A1 | 9/2010 | Lu |
| 2010/0262052 | A1 | 10/2010 | Lunau et al. |
| 2010/0268304 | A1 | 10/2010 | Matos |
| 2010/0293003 | A1 | 11/2010 | Abbo |
| 2010/0298102 | A1 | 11/2010 | Bosecker et al. |
| 2010/0326207 | A1 | 12/2010 | Topel |
| 2010/0332583 | A1 | 12/2010 | Szabo |
| 2011/0010188 | A1 | 1/2011 | Yoshikawa et al. |
| 2011/0047108 | A1 | 2/2011 | Chakrabarty et al. |
| 2011/0082007 | A1 | 4/2011 | Birrell |
| 2011/0087137 | A1 * | 4/2011 | Hanoun ................. G16H 20/30 600/587 |
| 2011/0119212 | A1 | 5/2011 | De Bruin et al. |
| 2011/0172059 | A1 | 7/2011 | Watterson et al. |
| 2011/0195819 | A1 | 8/2011 | Shaw et al. |
| 2011/0218462 | A1 | 9/2011 | Smith |
| 2011/0218814 | A1 | 9/2011 | Coats |
| 2011/0275483 | A1 | 11/2011 | Dugan |
| 2011/0281249 | A1 | 11/2011 | Gammell et al. |
| 2011/0306846 | A1 | 12/2011 | Osorio |
| 2012/0041771 | A1 | 2/2012 | Cosentino et al. |
| 2012/0065987 | A1 | 3/2012 | Farooq et al. |
| 2012/0116258 | A1 | 5/2012 | Lee |
| 2012/0130196 | A1 | 5/2012 | Jain et al. |
| 2012/0130197 | A1 | 5/2012 | Kugler et al. |
| 2012/0167709 | A1 | 7/2012 | Chen et al. |
| 2012/0183939 | A1 | 7/2012 | Aragones et al. |
| 2012/0190502 | A1 | 7/2012 | Paulus et al. |
| 2012/0232438 | A1 | 9/2012 | Cataldi et al. |
| 2012/0253241 | A1 | 10/2012 | Levital |
| 2012/0259648 | A1 | 10/2012 | Mallon et al. |
| 2012/0259649 | A1 | 10/2012 | Mallon et al. |
| 2012/0278759 | A1 | 11/2012 | Curl et al. |
| 2012/0295240 | A1 | 11/2012 | Walker et al. |
| 2012/0296455 | A1 | 11/2012 | Ohnemus et al. |
| 2012/0310667 | A1 | 12/2012 | Altman et al. |
| 2013/0066647 | A1 | 3/2013 | Andrie |
| 2013/0079925 | A1 | 3/2013 | Alaklabi et al. |
| 2013/0083054 | A1 | 4/2013 | Bayouk |
| 2013/0108594 | A1 | 5/2013 | Martin-Rendon et al. |
| 2013/0110545 | A1 | 5/2013 | Smallwood |
| 2013/0123071 | A1 | 5/2013 | Rhea |
| 2013/0123667 | A1 | 5/2013 | Komatireddy et al. |
| 2013/0137550 | A1 | 5/2013 | Skinner et al. |

(56) References Cited

U.S. PATENT DOCUMENTS

| | | | | |
|---|---|---|---|---|
| 2013/0137552 | A1 | 5/2013 | Kemp et al. | |
| 2013/0158368 | A1* | 6/2013 | Pacione | A61B 5/318 600/595 |
| 2013/0165195 | A1 | 6/2013 | Watterson | |
| 2013/0178334 | A1 | 7/2013 | Brammer | |
| 2013/0211281 | A1 | 8/2013 | Ross et al. | |
| 2013/0211774 | A1 | 8/2013 | Bentley | |
| 2013/0253943 | A1 | 9/2013 | Lee et al. | |
| 2013/0274069 | A1 | 10/2013 | Watterson et al. | |
| 2013/0296987 | A1 | 11/2013 | Rogers et al. | |
| 2013/0318027 | A1 | 11/2013 | Almogy et al. | |
| 2013/0332616 | A1 | 12/2013 | Landwehr | |
| 2013/0345025 | A1 | 12/2013 | van der Merwe | |
| 2014/0006042 | A1 | 1/2014 | Keefe et al. | |
| 2014/0011640 | A1 | 1/2014 | Dugan | |
| 2014/0031174 | A1 | 1/2014 | Huang | |
| 2014/0038781 | A1 | 2/2014 | Foley et al. | |
| 2014/0062900 | A1 | 3/2014 | Kaula et al. | |
| 2014/0074179 | A1 | 3/2014 | Heldman et al. | |
| 2014/0089836 | A1 | 3/2014 | Damani et al. | |
| 2014/0108035 | A1 | 4/2014 | Akbay | |
| 2014/0113261 | A1 | 4/2014 | Akiba | |
| 2014/0113768 | A1 | 4/2014 | Lin et al. | |
| 2014/0135173 | A1 | 5/2014 | Watterson | |
| 2014/0149129 | A1 | 5/2014 | Getchius | |
| 2014/0155129 | A1 | 6/2014 | Dugan | |
| 2014/0163439 | A1 | 6/2014 | Uryash et al. | |
| 2014/0172442 | A1 | 6/2014 | Broderick | |
| 2014/0172460 | A1 | 6/2014 | Kohli | |
| 2014/0172514 | A1 | 6/2014 | Schumann et al. | |
| 2014/0188009 | A1 | 7/2014 | Lange et al. | |
| 2014/0194250 | A1 | 7/2014 | Reich et al. | |
| 2014/0194251 | A1 | 7/2014 | Reich et al. | |
| 2014/0200414 | A1 | 7/2014 | Osorio | |
| 2014/0207264 | A1 | 7/2014 | Quy | |
| 2014/0207486 | A1 | 7/2014 | Carty et al. | |
| 2014/0228649 | A1 | 8/2014 | Rayner et al. | |
| 2014/0246499 | A1 | 9/2014 | Proud et al. | |
| 2014/0256511 | A1 | 9/2014 | Smith | |
| 2014/0257837 | A1 | 9/2014 | Walker et al. | |
| 2014/0274565 | A1 | 9/2014 | Boyette et al. | |
| 2014/0274622 | A1 | 9/2014 | Leonhard | |
| 2014/0275816 | A1 | 9/2014 | Sandmore | |
| 2014/0303540 | A1 | 10/2014 | Baym | |
| 2014/0309083 | A1 | 10/2014 | Dugan | |
| 2014/0322686 | A1 | 10/2014 | Kang | |
| 2014/0347265 | A1 | 11/2014 | Aimone et al. | |
| 2014/0371816 | A1 | 12/2014 | Matos | |
| 2014/0372133 | A1 | 12/2014 | Austrum et al. | |
| 2015/0025816 | A1 | 1/2015 | Ross | |
| 2015/0045700 | A1 | 2/2015 | Cavanagh et al. | |
| 2015/0046192 | A1 | 2/2015 | Raduchel | |
| 2015/0051721 | A1 | 2/2015 | Cheng | |
| 2015/0065213 | A1 | 3/2015 | Dugan | |
| 2015/0073814 | A1 | 3/2015 | Linebaugh | |
| 2015/0088544 | A1 | 3/2015 | Goldberg | |
| 2015/0094192 | A1 | 4/2015 | Skwortsow et al. | |
| 2015/0099458 | A1 | 4/2015 | Weisner et al. | |
| 2015/0099952 | A1 | 4/2015 | Lain et al. | |
| 2015/0111644 | A1 | 4/2015 | Larson | |
| 2015/0112230 | A1 | 4/2015 | Iglesias | |
| 2015/0112702 | A1 | 4/2015 | Joao et al. | |
| 2015/0130830 | A1 | 5/2015 | Nagasaki | |
| 2015/0141200 | A1 | 5/2015 | Murray et al. | |
| 2015/0142142 | A1 | 5/2015 | Aguilera et al. | |
| 2015/0149217 | A1 | 5/2015 | Kaburagi | |
| 2015/0151162 | A1 | 6/2015 | Dugan | |
| 2015/0157938 | A1 | 6/2015 | Domansky et al. | |
| 2015/0161331 | A1 | 6/2015 | Oleynik | |
| 2015/0161876 | A1 | 6/2015 | Castillo | |
| 2015/0174446 | A1 | 6/2015 | Chiang | |
| 2015/0196804 | A1 | 7/2015 | Koduri | |
| 2015/0196805 | A1 | 7/2015 | Koduri | |
| 2015/0199494 | A1 | 7/2015 | Koduri | |
| 2015/0217056 | A1 | 8/2015 | Kadavy et al. | |
| 2015/0251074 | A1 | 9/2015 | Ahmed et al. | |
| 2015/0257679 | A1 | 9/2015 | Ross | |
| 2015/0265209 | A1 | 9/2015 | Zhang | |
| 2015/0290061 | A1 | 10/2015 | Stafford et al. | |
| 2015/0331997 | A1* | 11/2015 | Joao | G16H 10/60 705/3 |
| 2015/0335950 | A1 | 11/2015 | Eder | |
| 2015/0335951 | A1 | 11/2015 | Eder | |
| 2015/0339442 | A1 | 11/2015 | Oleynik | |
| 2015/0341812 | A1 | 11/2015 | Dion et al. | |
| 2015/0351664 | A1 | 12/2015 | Ross | |
| 2015/0351665 | A1 | 12/2015 | Ross | |
| 2015/0360069 | A1 | 12/2015 | Marti et al. | |
| 2015/0379232 | A1 | 12/2015 | Mainwaring et al. | |
| 2015/0379430 | A1 | 12/2015 | Dirac et al. | |
| 2016/0004820 | A1 | 1/2016 | Moore | |
| 2016/0007885 | A1 | 1/2016 | Basta | |
| 2016/0015995 | A1 | 1/2016 | Leung et al. | |
| 2016/0023081 | A1 | 1/2016 | Popa-Simil et al. | |
| 2016/0045170 | A1 | 2/2016 | Migita | |
| 2016/0081594 | A1 | 3/2016 | Gaddipati | |
| 2016/0086500 | A1 | 3/2016 | Kaleal, III | |
| 2016/0096073 | A1 | 4/2016 | Rahman et al. | |
| 2016/0098808 | A1* | 4/2016 | Ziobro | G16H 20/30 705/2 |
| 2016/0117471 | A1 | 4/2016 | Belt et al. | |
| 2016/0132643 | A1 | 5/2016 | Radhakrishna et al. | |
| 2016/0140319 | A1 | 5/2016 | Stark | |
| 2016/0143593 | A1 | 5/2016 | Fu et al. | |
| 2016/0151670 | A1 | 6/2016 | Dugan | |
| 2016/0158534 | A1 | 6/2016 | Guarraia et al. | |
| 2016/0166833 | A1 | 6/2016 | Bum | |
| 2016/0166881 | A1 | 6/2016 | Ridgel et al. | |
| 2016/0193306 | A1 | 7/2016 | Rabovsky et al. | |
| 2016/0197918 | A1 | 7/2016 | Turgeman et al. | |
| 2016/0213924 | A1 | 7/2016 | Coleman | |
| 2016/0250519 | A1 | 9/2016 | Watterson | |
| 2016/0275259 | A1 | 9/2016 | Nolan et al. | |
| 2016/0287166 | A1 | 10/2016 | Tran | |
| 2016/0294837 | A1 | 10/2016 | Turgeman | |
| 2016/0302666 | A1 | 10/2016 | Shaya | |
| 2016/0302721 | A1 | 10/2016 | Wiedenhoefer et al. | |
| 2016/0317869 | A1 | 11/2016 | Dugan | |
| 2016/0322078 | A1 | 11/2016 | Bose et al. | |
| 2016/0325140 | A1 | 11/2016 | Wu | |
| 2016/0332028 | A1 | 11/2016 | Melnik | |
| 2016/0345841 | A1 | 12/2016 | Jang et al. | |
| 2016/0354636 | A1 | 12/2016 | Jang | |
| 2016/0361025 | A1 | 12/2016 | Reicher et al. | |
| 2016/0361597 | A1 | 12/2016 | Cole et al. | |
| 2016/0373477 | A1 | 12/2016 | Moyle | |
| 2017/0000422 | A1 | 1/2017 | Moturu et al. | |
| 2017/0004260 | A1 | 1/2017 | Moturu et al. | |
| 2017/0011179 | A1 | 1/2017 | Arshad et al. | |
| 2017/0017760 | A1 | 1/2017 | Freese et al. | |
| 2017/0032092 | A1 | 2/2017 | Mink et al. | |
| 2017/0033375 | A1 | 2/2017 | Ohmori et al. | |
| 2017/0042467 | A1 | 2/2017 | Herr et al. | |
| 2017/0043160 | A1 | 2/2017 | Goodall et al. | |
| 2017/0046488 | A1 | 2/2017 | Pereira | |
| 2017/0065851 | A1 | 3/2017 | Deluca et al. | |
| 2017/0069223 | A1 | 3/2017 | Cramer et al. | |
| 2017/0080320 | A1 | 3/2017 | Smith | |
| 2017/0091422 | A1 | 3/2017 | Kumar et al. | |
| 2017/0095670 | A1 | 4/2017 | Ghaffari et al. | |
| 2017/0095692 | A1 | 4/2017 | Chang et al. | |
| 2017/0095693 | A1 | 4/2017 | Chang et al. | |
| 2017/0100637 | A1 | 4/2017 | Princen et al. | |
| 2017/0106242 | A1 | 4/2017 | Dugan | |
| 2017/0113092 | A1 | 4/2017 | Johnson | |
| 2017/0128769 | A1 | 5/2017 | Long et al. | |
| 2017/0132947 | A1 | 5/2017 | Maeda et al. | |
| 2017/0136296 | A1 | 5/2017 | Barrera et al. | |
| 2017/0136298 | A1 | 5/2017 | Bae | |
| 2017/0143261 | A1 | 5/2017 | Wiedenhoefer et al. | |
| 2017/0147752 | A1 | 5/2017 | Toru | |
| 2017/0147789 | A1 | 5/2017 | Wiedenhoefer et al. | |
| 2017/0148297 | A1 | 5/2017 | Ross | |
| 2017/0168555 | A1 | 6/2017 | Munoz et al. | |

(56) References Cited

U.S. PATENT DOCUMENTS

2017/0169177 A1 6/2017 Beale
2017/0173391 A1 6/2017 Wiebe
2017/0181698 A1 6/2017 Wiedenhoefer et al.
2017/0190052 A1 7/2017 Jaekel et al.
2017/0202724 A1 7/2017 De Rossi
2017/0209766 A1 7/2017 Riley et al.
2017/0220751 A1 8/2017 Davis
2017/0228517 A1 8/2017 Saliman et al.
2017/0235882 A1 8/2017 Orlov et al.
2017/0235906 A1 8/2017 Dorris et al.
2017/0243028 A1 8/2017 LaFever et al.
2017/0258370 A1 9/2017 Plotnik-Peleg et al.
2017/0262604 A1 9/2017 Francois
2017/0265800 A1 9/2017 Auchinleck et al.
2017/0266501 A1 9/2017 Sanders et al.
2017/0270260 A1 9/2017 Shetty
2017/0277841 A1 9/2017 Shankar et al.
2017/0278209 A1 9/2017 Olsen et al.
2017/0282015 A1 10/2017 Wicks et al.
2017/0283508 A1 10/2017 Demopulos et al.
2017/0286621 A1 10/2017 Cox
2017/0291067 A1 10/2017 Jang et al.
2017/0296861 A1 10/2017 Burkinshaw
2017/0300654 A1 10/2017 Stein et al.
2017/0304024 A1 10/2017 Nobrega
2017/0312614 A1 11/2017 Tran et al.
2017/0323481 A1 11/2017 Tran et al.
2017/0329917 A1 11/2017 McRaith et al.
2017/0329933 A1 11/2017 Brust
2017/0333755 A1 11/2017 Rider
2017/0337033 A1 11/2017 Duyan et al.
2017/0337334 A1 11/2017 Stanczak
2017/0344726 A1 11/2017 Duffy et al.
2017/0347923 A1 12/2017 Roh
2017/0352157 A1 12/2017 Madabhushi
2017/0360586 A1 12/2017 Dempers et al.
2017/0361165 A1 12/2017 Miller et al.
2017/0367606 A1 12/2017 Lee
2017/0368413 A1 12/2017 Shavit
2018/0017806 A1 1/2018 Wang et al.
2018/0028896 A1 2/2018 Ray
2018/0036591 A1 2/2018 King et al.
2018/0036593 A1 2/2018 Ridgel et al.
2018/0052962 A1 2/2018 Van Der Koijk et al.
2018/0052968 A1 2/2018 Hickle et al.
2018/0056104 A1 3/2018 Cromie et al.
2018/0056130 A1 3/2018 Bitran et al.
2018/0060494 A1 3/2018 Dias et al.
2018/0070864 A1 3/2018 Schuster
2018/0071565 A1 3/2018 Gomberg et al.
2018/0071566 A1 3/2018 Gomberg et al.
2018/0071569 A1 3/2018 Gomberg et al.
2018/0071570 A1 3/2018 Gomberg et al.
2018/0071571 A1 3/2018 Gomberg et al.
2018/0071572 A1 3/2018 Gomberg et al.
2018/0071583 A1 3/2018 Paiz
2018/0075205 A1 3/2018 Moturu et al.
2018/0078149 A1 3/2018 Fonte et al.
2018/0078182 A1 3/2018 Chen
2018/0078843 A1 3/2018 Tran et al.
2018/0085615 A1 3/2018 Astolfi et al.
2018/0085630 A1 3/2018 Capell
2018/0089385 A1 3/2018 Gupta
2018/0096111 A1 4/2018 Wells et al.
2018/0099178 A1 4/2018 Schaefer et al.
2018/0102190 A1 4/2018 Hogue et al.
2018/0103859 A1 4/2018 Provenzano
2018/0113985 A1 4/2018 Gandy et al.
2018/0116741 A1 5/2018 Garcia Kilroy et al.
2018/0117417 A1 5/2018 Davis
2018/0130555 A1 5/2018 Chronis et al.
2018/0133551 A1 5/2018 Chang
2018/0140927 A1 5/2018 Kito
2018/0146870 A1 5/2018 Shemesh
2018/0177612 A1 6/2018 Trabish et al.
2018/0178061 A1 6/2018 O'Larte et al.
2018/0199855 A1 7/2018 Odame et al.
2018/0200577 A1 7/2018 Dugan
2018/0214729 A1 8/2018 Rubin
2018/0220935 A1 8/2018 Tadano et al.
2018/0228682 A1 8/2018 Bayerlein et al.
2018/0232492 A1 8/2018 Al-Alul et al.
2018/0236307 A1 8/2018 Hyde et al.
2018/0240552 A1 8/2018 Tuyl et al.
2018/0253991 A1 9/2018 Tang et al.
2018/0255110 A1 9/2018 Dowlatkhah et al.
2018/0256079 A1 9/2018 Yang et al.
2018/0256939 A1 9/2018 Malcolm
2018/0263530 A1 9/2018 Jung
2018/0263535 A1 9/2018 Cramer
2018/0263552 A1 9/2018 Graman et al.
2018/0264312 A1 9/2018 Pompile et al.
2018/0271432 A1 9/2018 Auchinleck et al.
2018/0272184 A1 9/2018 Vassilaros et al.
2018/0280784 A1 10/2018 Romeo et al.
2018/0285463 A1 10/2018 Choi et al.
2018/0290017 A1 10/2018 Fung
2018/0296143 A1 10/2018 Anderson et al.
2018/0296157 A1 10/2018 Bleich et al.
2018/0318122 A1 11/2018 LeCursi et al.
2018/0326243 A1 11/2018 Badi et al.
2018/0330058 A1 11/2018 Bates
2018/0330810 A1 11/2018 Gamarnik
2018/0330824 A1 11/2018 Athey et al.
2018/0353812 A1 12/2018 Lannon et al.
2018/0360340 A1 12/2018 Rehse et al.
2018/0361203 A1 12/2018 Wang
2018/0366225 A1 12/2018 Mansi et al.
2018/0373844 A1 12/2018 Ferrandez-Escamez et al.
2019/0005195 A1 1/2019 Peterson
2019/0009135 A1 1/2019 Wu
2019/0019163 A1 1/2019 Batey et al.
2019/0019573 A1 1/2019 Lake et al.
2019/0019578 A1 1/2019 Vaccaro
2019/0021929 A1* 1/2019 Einav ............... A63B 21/00181
2019/0030415 A1 1/2019 Volpe, Jr.
2019/0031284 A1 1/2019 Fuchs
2019/0046794 A1 2/2019 Goodall et al.
2019/0060708 A1 2/2019 Fung
2019/0065970 A1 2/2019 Bonutti et al.
2019/0066832 A1 2/2019 Kang et al.
2019/0076701 A1 3/2019 Dugan
2019/0080802 A1 3/2019 Ziobro et al.
2019/0083846 A1 3/2019 Eder
2019/0088356 A1 3/2019 Oliver et al.
2019/0090744 A1 3/2019 Mahfouz
2019/0096534 A1 3/2019 Joao
2019/0105551 A1 4/2019 Ray
2019/0108912 A1 4/2019 Spurlock, III
2019/0111299 A1 4/2019 Radcliffe et al.
2019/0115097 A1 4/2019 Macoviak et al.
2019/0117156 A1 4/2019 Howard et al.
2019/0118038 A1 4/2019 Tana et al.
2019/0118066 A1* 4/2019 Cardona ............ A63B 24/0062
2019/0126099 A1 5/2019 Hoang
2019/0132948 A1 5/2019 Longinotti-Buitoni et al.
2019/0134454 A1 5/2019 Mahoney et al.
2019/0137988 A1 5/2019 Cella et al.
2019/0143191 A1 5/2019 Ran et al.
2019/0143193 A1 5/2019 Kim
2019/0145774 A1 5/2019 Ellis
2019/0163876 A1 5/2019 Remme et al.
2019/0167988 A1 6/2019 Shahriari et al.
2019/0172587 A1 6/2019 Park et al.
2019/0175988 A1 6/2019 Volterrani et al.
2019/0183715 A1 6/2019 Kapure et al.
2019/0200920 A1 7/2019 Tien et al.
2019/0209891 A1 7/2019 Fung
2019/0214119 A1 7/2019 Wachira et al.
2019/0223797 A1 7/2019 Tran
2019/0224528 A1 7/2019 Omid-Zohoor et al.
2019/0228856 A1 7/2019 Leifer
2019/0232108 A1 8/2019 Kovach et al.
2019/0240103 A1 8/2019 Hepler et al.

(56) References Cited

U.S. PATENT DOCUMENTS

2019/0240541 A1 8/2019 Denton et al.
2019/0244540 A1 8/2019 Errante et al.
2019/0247718 A1* 8/2019 Blevins .................... G06N 5/02
2019/0251456 A1 8/2019 Constantin
2019/0251723 A1 8/2019 Coppersmith
2019/0261959 A1 8/2019 Frankel
2019/0262084 A1 8/2019 Roh
2019/0269343 A1 9/2019 Ramos Murguialday et al.
2019/0274523 A1 9/2019 Bates et al.
2019/0275368 A1 9/2019 Maroldi
2019/0283247 A1 9/2019 Chang
2019/0290191 A1 9/2019 Leppäluoto et al.
2019/0304584 A1 10/2019 Savolainen
2019/0307983 A1 10/2019 Goldman
2019/0314681 A1 10/2019 Yang
2019/0344123 A1 11/2019 Rubin et al.
2019/0354632 A1 11/2019 Mital et al.
2019/0362242 A1 11/2019 Pillai et al.
2019/0366146 A1 12/2019 Tong et al.
2019/0371472 A1 12/2019 Blanchard
2019/0385199 A1 12/2019 Bender et al.
2019/0388728 A1 12/2019 Wang et al.
2019/0392936 A1 12/2019 Arric et al.
2019/0392939 A1 12/2019 Basta et al.
2020/0005928 A1* 1/2020 Daniel .................. G16H 15/00
2020/0015736 A1 1/2020 Alhathal
2020/0034665 A1 1/2020 Ghanta
2020/0034707 A1 1/2020 Kivatinos et al.
2020/0038703 A1 2/2020 Cleary et al.
2020/0051446 A1 2/2020 Rubinstein
2020/0054922 A1 2/2020 Azaria
2020/0066390 A1 2/2020 Svendrys et al.
2020/0085300 A1 3/2020 Kwatra et al.
2020/0090802 A1 3/2020 Maron
2020/0093418 A1 3/2020 Kluger et al.
2020/0098463 A1 3/2020 Arunachalam et al.
2020/0121987 A1 4/2020 Loh
2020/0129237 A1 4/2020 Erdem
2020/0129808 A1 4/2020 Fomin
2020/0139194 A1 5/2020 Min
2020/0143922 A1 5/2020 Chekroud et al.
2020/0151595 A1* 5/2020 Jayalath ............. A63B 21/0442
2020/0151646 A1 5/2020 De La Fuente Sanchez
2020/0152339 A1 5/2020 Pulitzer et al.
2020/0160198 A1 5/2020 Reeves et al.
2020/0170876 A1 6/2020 Kapure et al.
2020/0176098 A1 6/2020 Lucas et al.
2020/0188774 A1 6/2020 Fung
2020/0197744 A1 6/2020 Schweighofer
2020/0221975 A1 7/2020 Basta et al.
2020/0237291 A1 7/2020 Raja
2020/0237452 A1 7/2020 Wolf et al.
2020/0261763 A1 8/2020 Park
2020/0267487 A1 8/2020 Siva
2020/0275886 A1 9/2020 Mason
2020/0289045 A1 9/2020 Hacking et al.
2020/0289046 A1 9/2020 Hacking et al.
2020/0289879 A1 9/2020 Hacking et al.
2020/0289880 A1 9/2020 Hacking et al.
2020/0289881 A1 9/2020 Hacking et al.
2020/0289889 A1 9/2020 Hacking et al.
2020/0293712 A1 9/2020 Potts et al.
2020/0303063 A1 9/2020 Sharma et al.
2020/0312447 A1 10/2020 Bohn et al.
2020/0320454 A1 10/2020 Almashor
2020/0334972 A1 10/2020 Gopalakrishnan
2020/0338394 A1 10/2020 Neumann
2020/0346072 A1 11/2020 Shah
2020/0353314 A1 11/2020 Messinger
2020/0357299 A1 11/2020 Patel et al.
2020/0365256 A1 11/2020 Hayashitani et al.
2020/0376327 A1 12/2020 Bissonnette
2020/0391080 A1 12/2020 Powers
2020/0395112 A1 12/2020 Ronner
2020/0398083 A1 12/2020 Adelsheim
2020/0401224 A1 12/2020 Cotton
2020/0402638 A1 12/2020 Song et al.
2020/0402662 A1 12/2020 Esmailian et al.
2020/0410374 A1 12/2020 White
2020/0410385 A1 12/2020 Otsuki
2020/0410893 A1 12/2020 Ridington
2020/0411162 A1 12/2020 Lien et al.
2020/0411170 A1 12/2020 Brown
2021/0005224 A1 1/2021 Rothschild et al.
2021/0005319 A1 1/2021 Otsuki et al.
2021/0008413 A1 1/2021 Asikainen et al.
2021/0015560 A1 1/2021 Boddington et al.
2021/0027889 A1 1/2021 Neil et al.
2021/0035674 A1 2/2021 Volosin et al.
2021/0050086 A1 2/2021 Rose et al.
2021/0065855 A1 3/2021 Pepin et al.
2021/0074178 A1 3/2021 Ilan et al.
2021/0076981 A1 3/2021 Hacking et al.
2021/0077860 A1 3/2021 Posnack et al.
2021/0077884 A1 3/2021 De Las Casas Zolezzi et al.
2021/0082554 A1 3/2021 Kalia et al.
2021/0093891 A1 4/2021 Sheng
2021/0098099 A1 4/2021 Neumann
2021/0098129 A1 4/2021 Neumann
2021/0101051 A1 4/2021 Posnack et al.
2021/0106899 A1 4/2021 Willardson
2021/0113890 A1 4/2021 Posnack et al.
2021/0125696 A1 4/2021 Liu et al.
2021/0127974 A1 5/2021 Mason et al.
2021/0128080 A1 5/2021 Mason et al.
2021/0128255 A1 5/2021 Mason et al.
2021/0128978 A1 5/2021 Gilstrom et al.
2021/0134412 A1 5/2021 Guaneri et al.
2021/0134425 A1 5/2021 Mason et al.
2021/0134427 A1 5/2021 Mason et al.
2021/0134428 A1 5/2021 Mason
2021/0134429 A1 5/2021 Mason
2021/0134430 A1 5/2021 Mason et al.
2021/0134432 A1 5/2021 Mason et al.
2021/0134456 A1 5/2021 Posnack et al.
2021/0134457 A1 5/2021 Mason et al.
2021/0134458 A1 5/2021 Mason et al.
2021/0134463 A1 5/2021 Mason et al.
2021/0138304 A1 5/2021 Mason et al.
2021/0142875 A1 5/2021 Mason et al.
2021/0142893 A1 5/2021 Guaneri et al.
2021/0142898 A1 5/2021 Mason et al.
2021/0142903 A1 5/2021 Mason et al.
2021/0144074 A1 5/2021 Guaneri et al.
2021/0186419 A1 6/2021 Van Ee et al.
2021/0187348 A1 6/2021 Phillips et al.
2021/0202090 A1 7/2021 ODonovan et al.
2021/0202103 A1 7/2021 Bostic et al.
2021/0205660 A1 7/2021 Shavit
2021/0217516 A1 7/2021 Nash
2021/0236020 A1 8/2021 Matijevich et al.
2021/0240853 A1 8/2021 Carlson
2021/0241137 A1* 8/2021 Jain ........................ G16H 20/30
2021/0244998 A1 8/2021 Hacking et al.
2021/0245003 A1 8/2021 Turner
2021/0251562 A1 8/2021 Jain
2021/0272677 A1 9/2021 Barbee
2021/0291010 A1 9/2021 Miller
2021/0338469 A1 11/2021 Dempers
2021/0343384 A1 11/2021 Purushothaman et al.
2021/0345879 A1 11/2021 Mason et al.
2021/0345975 A1 11/2021 Mason et al.
2021/0350888 A1 11/2021 Guaneri et al.
2021/0350898 A1 11/2021 Mason et al.
2021/0350899 A1 11/2021 Mason et al.
2021/0350901 A1 11/2021 Mason et al.
2021/0350902 A1 11/2021 Mason et al.
2021/0350914 A1 11/2021 Guaneri et al.
2021/0350926 A1 11/2021 Mason et al.
2021/0354002 A1 11/2021 Schaefer
2021/0361514 A1 11/2021 Choi et al.
2021/0366587 A1 11/2021 Mason et al.
2021/0375425 A1 12/2021 Zhang
2021/0383909 A1 12/2021 Mason et al.

(56) References Cited

U.S. PATENT DOCUMENTS

2021/0391091 A1 12/2021 Mason
2021/0394011 A1 12/2021 Neuhaus et al.
2021/0398668 A1 12/2021 Chock et al.
2021/0406738 A1 12/2021 O'Donncha et al.
2021/0407670 A1 12/2021 Mason et al.
2021/0407681 A1 12/2021 Mason et al.
2022/0000556 A1 1/2022 Casey et al.
2022/0015838 A1 1/2022 Posnack
2022/0016480 A1 1/2022 Bissonnette et al.
2022/0016482 A1 1/2022 Bissonnette
2022/0016484 A1 1/2022 Bissonnett et al.
2022/0016485 A1 1/2022 Bissonnette
2022/0016486 A1 1/2022 Bissonnette et al.
2022/0020469 A1 1/2022 Tanner
2022/0044806 A1 2/2022 Sanders et al.
2022/0047921 A1 2/2022 Bissonnette
2022/0066548 A1 3/2022 Helot
2022/0079690 A1 3/2022 Mason et al.
2022/0080256 A1 3/2022 Arn et al.
2022/0080265 A1 3/2022 Watterson
2022/0096006 A1 3/2022 Wu et al.
2022/0105384 A1 4/2022 Hacking et al.
2022/0105385 A1 4/2022 Hacking et al.
2022/0105390 A1 4/2022 Yuasa
2022/0115133 A1 4/2022 Mason et al.
2022/0117514 A1 4/2022 Kuhn et al.
2022/0118218 A1 4/2022 Bense et al.
2022/0122724 A1 4/2022 Durlach et al.
2022/0126169 A1 4/2022 Mason
2022/0133576 A1 5/2022 Choi et al.
2022/0148725 A1 5/2022 Mason et al.
2022/0158916 A1 5/2022 Mason et al.
2022/0165398 A1 5/2022 Avila-Hernandez et al.
2022/0176039 A1 6/2022 Lintereur et al.
2022/0181004 A1 6/2022 Zilca et al.
2022/0193491 A1 6/2022 Mason
2022/0230729 A1 7/2022 Mason
2022/0238222 A1 7/2022 Neuberg
2022/0238223 A1 7/2022 Mason
2022/0258935 A1 8/2022 Kraft
2022/0262483 A1 8/2022 Rosenberg et al.
2022/0262504 A1 8/2022 Bratty et al.
2022/0266094 A1 8/2022 Mason et al.
2022/0270738 A1 8/2022 Mason et al.
2022/0273985 A1 9/2022 Jeong et al.
2022/0273986 A1 9/2022 Mason
2022/0288460 A1 9/2022 Mason
2022/0288461 A1 9/2022 Ashley et al.
2022/0288462 A1 9/2022 Ashley et al.
2022/0293257 A1 9/2022 Guaneri et al.
2022/0300787 A1 9/2022 Wall et al.
2022/0304881 A1 9/2022 Choi et al.
2022/0304882 A1 9/2022 Choi
2022/0305291 A1 9/2022 Hibbard
2022/0305328 A1 9/2022 Choi et al.
2022/0314072 A1 10/2022 Bissonnette et al.
2022/0314075 A1 10/2022 Mason et al.
2022/0323826 A1 10/2022 Khurana
2022/0327714 A1 10/2022 Cook et al.
2022/0327807 A1 10/2022 Cook et al.
2022/0328181 A1 10/2022 Mason et al.
2022/0330823 A1 10/2022 Janssen
2022/0331663 A1 10/2022 Mason
2022/0336077 A1 10/2022 Chen et al.
2022/0338761 A1 10/2022 Maddahi et al.
2022/0339052 A1 10/2022 Kim
2022/0339501 A1 10/2022 Mason et al.
2022/0342969 A1 10/2022 Watterson et al.
2022/0346703 A1 11/2022 Abdo et al.
2022/0370851 A1 11/2022 Guidarelli et al.
2022/0384010 A1 12/2022 Kanayama
2022/0384012 A1 12/2022 Mason
2022/0392591 A1 12/2022 Guaneri et al.
2022/0395232 A1 12/2022 Locke
2022/0401783 A1 12/2022 Choi
2022/0415469 A1 12/2022 Mason
2022/0415471 A1 12/2022 Mason
2023/0001268 A1 1/2023 Bissonnette et al.
2023/0013530 A1 1/2023 Mason
2023/0014598 A1 1/2023 Mason et al.
2023/0029639 A1 2/2023 Roy
2023/0047253 A1 2/2023 Gnanasambandam et al.
2023/0048040 A1 2/2023 Hacking et al.
2023/0051751 A1 2/2023 Hacking et al.
2023/0055078 A1 2/2023 Malcolm
2023/0058605 A1 2/2023 Mason
2023/0060039 A1 2/2023 Mason
2023/0072368 A1 3/2023 Mason
2023/0078793 A1 3/2023 Mason
2023/0119461 A1 4/2023 Mason
2023/0190100 A1 6/2023 Stump
2023/0197240 A1 6/2023 Rosenberg
2023/0201656 A1 6/2023 Hacking et al.
2023/0207097 A1 6/2023 Mason
2023/0207124 A1 6/2023 Walsh et al.
2023/0215539 A1 7/2023 Rosenberg et al.
2023/0215552 A1 7/2023 Khotilovich et al.
2023/0218950 A1 7/2023 Belson et al.
2023/0245747 A1 8/2023 Rosenberg et al.
2023/0245748 A1 8/2023 Rosenberg et al.
2023/0245750 A1 8/2023 Rosenberg et al.
2023/0245751 A1 8/2023 Rosenberg et al.
2023/0249599 A1 8/2023 Nicola
2023/0253089 A1 8/2023 Rosenberg et al.
2023/0255555 A1 8/2023 Sundaram et al.
2023/0263428 A1 8/2023 Hull et al.
2023/0274813 A1 8/2023 Rosenberg et al.
2023/0282329 A1 9/2023 Mason et al.
2023/0364471 A1 11/2023 Choi et al.
2023/0364472 A1 11/2023 Posnack
2023/0368886 A1 11/2023 Rosenberg
2023/0377710 A1 11/2023 Chen et al.
2023/0377711 A1 11/2023 Rosenberg
2023/0377712 A1 11/2023 Rosenberg
2023/0386639 A1 11/2023 Rosenberg
2023/0390627 A1 12/2023 Bolton
2023/0395231 A1 12/2023 Rosenberg
2023/0395232 A1 12/2023 Rosenberg
2024/0029856 A1 1/2024 Rosenberg
2024/0058651 A1 2/2024 Bissonnette
2024/0177846 A1 5/2024 Gnanasambandam
2024/0203580 A1 6/2024 Mason

FOREIGN PATENT DOCUMENTS

CN 101964151 A 2/2011
CN 201889024 U 7/2011
CN 202220794 U 5/2012
CN 102670381 A 9/2012
CN 103263336 A 8/2013
CN 103390357 A 11/2013
CN 103473631 A 12/2013
CN 103488880 A 1/2014
CN 103501328 A 1/2014
CN 103721343 A 4/2014
CN 203677851 U 7/2014
CN 104335211 A 2/2015
CN 105263448 A 1/2016
CN 105620643 A 6/2016
CN 105683977 A 6/2016
CN 103136447 B 8/2016
CN 105894088 A 8/2016
CN 105930668 A 9/2016
CN 205626871 U 10/2016
CN 106127646 A 11/2016
CN 106236502 A 12/2016
CN 106510985 A 3/2017
CN 106621195 A 5/2017
CN 107066819 A 8/2017
CN 107430641 A 12/2017
CN 107551475 A 1/2018
CN 107736982 A 2/2018
CN 107930021 A 4/2018
CN 108078737 A 5/2018

(56) References Cited

FOREIGN PATENT DOCUMENTS

| | | | |
|---|---|---|---|
| CN | 208224811 | A | 12/2018 |
| CN | 109191954 | A | 1/2019 |
| CN | 109363887 | A | 2/2019 |
| CN | 208573971 | U | 3/2019 |
| CN | 110148472 | A | 8/2019 |
| CN | 110201358 | A | 9/2019 |
| CN | 110215188 | A | 9/2019 |
| CN | 110322957 | A | 10/2019 |
| CN | 110808092 | A | 2/2020 |
| CN | 110931103 | A | 3/2020 |
| CN | 110993057 | A | 4/2020 |
| CN | 111105859 | A | 5/2020 |
| CN | 111111110 | A | 5/2020 |
| CN | 111370088 | A | 7/2020 |
| CN | 111460305 | A | 7/2020 |
| CN | 111790111 | A | 10/2020 |
| CN | 112071393 | A | 12/2020 |
| CN | 212141371 | U | 12/2020 |
| CN | 112289425 | A | 1/2021 |
| CN | 212624809 | U | 2/2021 |
| CN | 112603295 | A | 4/2021 |
| CN | 213190965 | U | 5/2021 |
| CN | 113384850 | A | 9/2021 |
| CN | 113499572 | A | 10/2021 |
| CN | 215136488 | U | 12/2021 |
| CN | 113885361 | A | 1/2022 |
| CN | 114049961 | A | 2/2022 |
| CN | 114203274 | A | 3/2022 |
| CN | 216258145 | U | 4/2022 |
| CN | 114632302 | A | 6/2022 |
| CN | 114694824 | A | 7/2022 |
| CN | 114898832 | A | 8/2022 |
| CN | 114983760 | A | 9/2022 |
| CN | 217472652 | U | 9/2022 |
| CN | 110270062 | B | 10/2022 |
| CN | 218420859 | U | 2/2023 |
| CN | 115954081 | A | 4/2023 |
| DE | 95019 | C | 1/1897 |
| DE | 7628633 | U1 | 12/1977 |
| DE | 8519150 | U1 | 10/1985 |
| DE | 3732905 | A1 | 7/1988 |
| DE | 19619820 | A1 | 12/1996 |
| DE | 29620008 | U1 | 2/1997 |
| DE | 19947926 | A1 | 4/2001 |
| DE | 102018202497 | A1 | 8/2018 |
| DE | 102018211212 | A1 | 1/2019 |
| DE | 102019108425 | B3 | 8/2020 |
| EP | 199600 | A2 | 10/1986 |
| EP | 0383137 | A2 | 8/1990 |
| EP | 634319 | A2 | 1/1995 |
| EP | 0919259 | A1 | 6/1999 |
| EP | 1034817 | A1 | 9/2000 |
| EP | 1159989 | A1 | 12/2001 |
| EP | 1391179 | A1 | 2/2004 |
| EP | 1968028 | | 9/2008 |
| EP | 2564904 | A1 | 3/2013 |
| EP | 2575064 | A1 | 4/2013 |
| EP | 1909730 | B1 | 4/2014 |
| EP | 2815242 | A4 | 12/2014 |
| EP | 2869805 | A | 5/2015 |
| EP | 2997951 | A1 | 3/2016 |
| EP | 2688472 | B1 | 4/2016 |
| EP | 3264303 | A1 | 1/2018 |
| EP | 3323473 | A1 | 5/2018 |
| EP | 3547322 | A1 | 10/2019 |
| EP | 3627514 | A1 | 3/2020 |
| EP | 3671700 | A1 | 6/2020 |
| EP | 3688537 | A1 | 8/2020 |
| EP | 3731733 | A1 | 11/2020 |
| EP | 3984508 | A1 | 4/2022 |
| EP | 3984509 | A1 | 4/2022 |
| EP | 3984510 | A1 | 4/2022 |
| EP | 3984511 | A1 | 4/2022 |
| EP | 3984512 | A1 | 4/2022 |
| EP | 3984513 | A1 | 4/2022 |
| EP | 4054699 | A1 | 9/2022 |
| EP | 4112033 | A1 | 1/2023 |
| FR | 2527541 | A2 | 12/1983 |
| FR | 3127393 | A1 | 3/2023 |
| GB | 141664 | A | 11/1920 |
| GB | 2336140 | A | 10/1999 |
| GB | 2372459 | A | 8/2002 |
| GB | 2512431 | A | 10/2014 |
| GB | 2591542 | B | 3/2022 |
| IN | 201811043670 | A | 7/2018 |
| JP | 2000005339 | A | 1/2000 |
| JP | 2003225875 | A | 8/2003 |
| JP | 2005227928 | A | 8/2005 |
| JP | 2005227928 | A1 | 8/2005 |
| JP | 2009112336 | A | 5/2009 |
| JP | 2013515995 | A | 5/2013 |
| JP | 2014104139 | A | 6/2014 |
| JP | 3193662 | U | 10/2014 |
| JP | 3198173 | U | 6/2015 |
| JP | 5804063 | B2 | 11/2015 |
| JP | 2018102842 | A | 7/2018 |
| JP | 2019028647 | A | 2/2019 |
| JP | 2019134909 | A | 8/2019 |
| JP | 6573739 | B1 | 9/2019 |
| JP | 6659831 | B2 | 3/2020 |
| JP | 2020057082 | A | 4/2020 |
| JP | 6710357 | B1 | 6/2020 |
| JP | 6775757 | B1 | 10/2020 |
| JP | 2021027917 | A | 2/2021 |
| JP | 6871379 | B2 | 5/2021 |
| JP | 2022521378 | A | 4/2022 |
| JP | 3238491 | U | 7/2022 |
| JP | 7198364 | B2 | 12/2022 |
| JP | 7202474 | B2 | 1/2023 |
| JP | 7231750 | B2 | 3/2023 |
| JP | 7231751 | B2 | 3/2023 |
| JP | 7231752 | B2 | 3/2023 |
| KR | 20020009724 | A | 2/2002 |
| KR | 200276919 | Y1 | 5/2002 |
| KR | 20020065253 | A | 8/2002 |
| KR | 100582596 | B1 | 5/2006 |
| KR | 101042258 | B1 | 6/2011 |
| KR | 101258250 | B1 | 4/2013 |
| KR | 101325581 | B1 | 11/2013 |
| KR | 20140128630 | A | 11/2014 |
| KR | 20150017693 | A | 2/2015 |
| KR | 20150078191 | A | 7/2015 |
| KR | 101580071 | B1 | 12/2015 |
| KR | 101647620 | B1 | 8/2016 |
| KR | 20160093990 | A | 8/2016 |
| KR | 20170038837 | A | 4/2017 |
| KR | 20180004928 | A | 1/2018 |
| KR | 20190029175 | A | 3/2019 |
| KR | 20190056116 | A | 5/2019 |
| KR | 101988167 | B1 | 6/2019 |
| KR | 101969392 | B1 | 8/2019 |
| KR | 102055279 | B1 | 12/2019 |
| KR | 20200019548 | A | 2/2020 |
| KR | 102088333 | B1 | 3/2020 |
| KR | 20200025290 | A | 3/2020 |
| KR | 20200029180 | A | 3/2020 |
| KR | 102097190 | B1 | 4/2020 |
| KR | 102116664 | B1 | 5/2020 |
| KR | 102116968 | B1 | 5/2020 |
| KR | 20200056233 | A | 5/2020 |
| KR | 102120828 | B1 | 6/2020 |
| KR | 102121586 | B1 | 6/2020 |
| KR | 102142713 | B1 | 8/2020 |
| KR | 102162522 | B1 | 10/2020 |
| KR | 20200119665 | A | 10/2020 |
| KR | 102173553 | B1 | 11/2020 |
| KR | 102180079 | B1 | 11/2020 |
| KR | 102188766 | B1 | 12/2020 |
| KR | 102196793 | B1 | 12/2020 |
| KR | 20210006212 | A | 1/2021 |
| KR | 102224188 | B1 | 3/2021 |
| KR | 102224618 | B1 | 3/2021 |
| KR | 102246049 | B1 | 4/2021 |
| KR | 102246050 | B1 | 4/2021 |

(56) References Cited

FOREIGN PATENT DOCUMENTS

| | | | |
|---|---|---|---|
| KR | 102246051 | B1 | 4/2021 |
| KR | 102246052 | B1 | 4/2021 |
| KR | 20210052028 | A | 5/2021 |
| KR | 102264498 | B1 | 6/2021 |
| KR | 102352602 | B1 | 1/2022 |
| KR | 102352603 | B1 | 1/2022 |
| KR | 102352604 | B1 | 1/2022 |
| KR | 20220004639 | A | 1/2022 |
| KR | 102387577 | B1 | 4/2022 |
| KR | 102421437 | B1 | 7/2022 |
| KR | 20220102207 | A | 7/2022 |
| KR | 102427545 | B1 | 8/2022 |
| KR | 102467495 | B1 | 11/2022 |
| KR | 102467496 | B1 | 11/2022 |
| KR | 102469723 | B1 | 11/2022 |
| KR | 102471990 | B1 | 11/2022 |
| KR | 20220145989 | A | 11/2022 |
| KR | 20220156134 | A | 11/2022 |
| KR | 102502744 | B1 | 2/2023 |
| KR | 20230019349 | A | 2/2023 |
| KR | 20230019350 | A | 2/2023 |
| KR | 20230026556 | A | 2/2023 |
| KR | 20230026668 | A | 2/2023 |
| KR | 20230040526 | | 3/2023 |
| KR | 20230050506 | A | 4/2023 |
| KR | 20230056118 | A | 4/2023 |
| KR | 102528503 | B1 | 5/2023 |
| KR | 102531930 | B1 | 5/2023 |
| KR | 102532766 | B1 | 5/2023 |
| KR | 102539190 | B1 | 6/2023 |
| NO | 2022212921 | A1 | 10/2022 |
| RU | 2014131288 | A | 2/2016 |
| RU | 2607953 | C2 | 1/2017 |
| TW | M474545 | U | 3/2014 |
| TW | I442956 | B | 7/2014 |
| TW | M638437 | U | 3/2023 |
| WO | 1998009687 | A1 | 3/1998 |
| WO | 0149235 | A2 | 7/2001 |
| WO | 0151083 | A2 | 7/2001 |
| WO | 2001050387 | A1 | 7/2001 |
| WO | 2001056465 | A1 | 8/2001 |
| WO | 02062211 | A2 | 8/2002 |
| WO | 02093312 | A2 | 11/2002 |
| WO | 2003043494 | A1 | 5/2003 |
| WO | 2005018453 | A1 | 3/2005 |
| WO | 2005074369 | A2 | 8/2005 |
| WO | 2006004430 | A2 | 1/2006 |
| WO | 2006012694 | A1 | 2/2006 |
| WO | 2007102709 | A1 | 9/2007 |
| WO | 2008114291 | A1 | 9/2008 |
| WO | 2008140780 | A1 | 11/2008 |
| WO | 2009003170 | A1 | 12/2008 |
| WO | 2009008968 | A1 | 1/2009 |
| WO | 2011025322 | A2 | 3/2011 |
| WO | 2012128801 | A1 | 9/2012 |
| WO | 2013002568 | A2 | 1/2013 |
| WO | 2023164292 | A1 | 3/2013 |
| WO | 2013122839 | A1 | 8/2013 |
| WO | 2014011447 | A1 | 1/2014 |
| WO | 2014163976 | A1 | 10/2014 |
| WO | 2015026744 | A1 | 2/2015 |
| WO | 2015065298 | A1 | 5/2015 |
| WO | 2015082555 | A1 | 6/2015 |
| WO | 2016151364 | A1 | 9/2016 |
| WO | 2016154318 | A1 | 9/2016 |
| WO | 2017030781 | A1 | 2/2017 |
| WO | 2017166074 | A1 | 5/2017 |
| WO | 2017091691 | A1 | 6/2017 |
| WO | 2017165238 | A1 | 9/2017 |
| WO | 2018027080 | A1 | 2/2018 |
| WO | 2018081795 | A1 | 5/2018 |
| WO | 2018171853 | A1 | 9/2018 |
| WO | 2019022706 | A1 | 1/2019 |
| WO | 2019106003 | A1 | 6/2019 |
| WO | 2019143940 | A1 | 7/2019 |
| WO | 2020014710 | A2 | 1/2020 |
| WO | 2020075190 | A1 | 4/2020 |
| WO | 2020130979 | A1 | 6/2020 |
| WO | 2020149815 | A2 | 7/2020 |
| WO | 2020229705 | A1 | 11/2020 |
| WO | 2020245727 | A1 | 12/2020 |
| WO | 2020249855 | A1 | 12/2020 |
| WO | 2020252599 | A1 | 12/2020 |
| WO | 2020256577 | A1 | 12/2020 |
| WO | 2021021447 | A1 | 2/2021 |
| WO | 2021022003 | A1 | 2/2021 |
| WO | 2021038980 | A1 | 3/2021 |
| WO | 2021055427 | A1 | 3/2021 |
| WO | 2021061061 | A1 | 4/2021 |
| WO | 2021090267 | A1 | 5/2021 |
| WO | 2021138620 | A1 | 7/2021 |
| WO | 2021216881 | A1 | 10/2021 |
| WO | 2021236961 | A1 | 11/2021 |
| WO | 2022047006 | A1 | 3/2022 |
| WO | 2022092493 | A1 | 5/2022 |
| WO | 2022092494 | A1 | 5/2022 |
| WO | 2022212883 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |
| WO | 2024013267 | A1 | 1/2024 |
| WO | 2024107807 | A1 | 5/2024 |

OTHER PUBLICATIONS

Alex Bellec, “Part-of-Speech tagging tutorial with the Keras Deep Learning library,” pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https://towardsdatascience.com/all-you-need-to-know-about-text-preprocessing-for-nlp-and-machine-learning-bcl c5765ff67.

Badreesh Shetty, “Natural Language Processing (NPL) for Machine Learning,” pp. 1-13, published Nov. 24, 2018, retrieved on Feb. 1, 2022 from https://towardsdatascience. com/natural-language-processing-nlp-for-machine-learning-d44498845d5b.

Website for “Pedal Exerciser”, p. 1, retrieved on Sep. 9, 2022 from https://www.vivehealth.com/collections/physical-therapy-equipment/products/pedalexerciser.

Website for “Functional Knee Brace with ROM”, p. 1, retrieved on Sep. 9, 2022 from http://medicalbrace.gr/en/product/functional-knee-brace-with-goniometer-mbtelescopicknee/.

Website for “ComfySplints Goniometer Knee”, pp. 1-5, retrieved on Sep. 9, 2022 from https://www.comfysplints.com/product/knee-splints/.

Website for “BMI FlexEze Knee Corrective Orthosis (KCO)”, pp. 1-4, retrieved on Sep. 9, 2022 from https://orthobmi.com/products/bmi-flexeze%C2%AE-knee-corrective-orthosis-kco.

Website for “Neoprene Knee Brace with goniometer—Patella Rom MB.4070”, pp. 1-4, retrieved on Sep. 9, 2022 from https://www.fortuna.com.gr/en/product/neoprene-knee-brace-with-goniometer-patella-rom-mb-4070/.

Kuiken et al., “Computerized Biofeedback Knee Goniometer: Acceptance and Effect on Exercise Behavior in Post-total Knee Arthroplasty Rehabilitation,” Biomedical Engineering Faculty Research and Publications, 2004, pp. 1-10.

Ahmed et al., “Artificial intelligence with multi-functional machine learning platform development for better healthcare and precision medicine,” Database, 2020, pp. 1-35.

Davenport et al., “The potential for artificial intelligence in healthcare,” Digital Technology, Future Healthcare Journal, 2019, pp. 1-5, vol. 6, No. 2.

(56) References Cited

OTHER PUBLICATIONS

Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.
International Preliminary Report on Patentability of International Application No. PCT/US2017/50895, Date of Mailing Dec. 11, 2018, 52 pages.
International Searching Authority, Search Report and Written Opinion for International Application No. PCT/US2017/50895, Date of Mailing Jan. 12, 2018, 6 pages.
International Searching Authority, Search Report and Written Opinion for International Application No. PCT/US2020/021876, Date of Mailing May 28, 2020, 8 pages.
International Searching Authority, Search Report and Written Opinion for International Application No. PCT/US2020/051008, Date of Mailing Dec. 10, 2020, 9 pages.
International Searching Authority, Search Report and Written Opinion for International Application No. PCT/US2020/056661, Date of Mailing Feb. 12, 2021, 12 pages.
International Searching Authority, Search Report and Written Opinion for International Application No. PCT/US2021/032807, Date of Mailing Sep. 6, 2021, 11 pages.
Matrix, R3xm Recumbent Cycle, retrieved on Aug. 4, 2020, 7 pages, https://www.matrixfitness.com/en/cardio/cycles/r3xm-recumbent.
ROM3 Rehab, ROM3 Rehab System, Apr. 20, 2015, retrieved on Aug. 31, 2018, 12 pages, https://vimeo.com/125438463.
Ahmed et al., "Artificial Intelligence With Multi-Functional Machine Learning Platform Development For Better Healthcare And Precision Medicine," Database (Oxford), 2020, pp. 1-35, vol. 2020.
Davenport et al., "The Potential For Artificial Intelligence in Healthcare," Future Healthcare Journal, 2019, pp. 94-98, vol. 6, No. 2.
Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health Networking, Applications and Services, Columbia, MO, USA, 2011, 6 pages.
Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.
Ishraque et al., "Artificial Intelligence-Based Rehabilitation Therapy Exercise Recommendation System," 2018 IEEE Mit Undergraduate Research Technology Conference (URTC), Cambridge, Ma, USA, 2018, 5 pages.
Zakari et al., "Are There Limitations to Exercise Benefits in Peripheral Arterial Disease?," Frontiers in Cardiovascular Medicine, Nov. 2018, vol. 5, Article 173, 12 pages.
You et al., "Including Blood Vasculature into a Game-Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE EMBS, 5 pages.
Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.
Chrif et al., "Control design for a lower-limb paediatric therapy device using linear motor technology," Article, 2017, pp. 119-127, Science Direct, Switzerland.
Robben et al., "Delta Features From Ambient Sensor Data are Good Predictors of Change in Functional Health," Article, 2016, pp. 2168-2194, vol. 21, No. 4, IEEE Journal of Biomedical and Health Informatics.
Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.
Warburton et al., "International Launch of the Par-•Q+ And ePARmed-•X+ Validation of the PAR-•Q+ and ePARmed••X+," Health & Fitness Journal of Canada, 2011, 9 pages, vol. 4, No. 2.
Barrett et al., "Artificial intelligence supported patient self-care in chronic heart failure: a paradigm shift from reactive to predictive, preventive and personalised care," EPMA Journal (2019), pp. 445-464.
Derkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.
Thomas et al., "Home-Based Cardiac Rehabilitation," Circulation, 2019, pp. e69-e89, vol. 140.
Thomas et al., "Home-Based Cardiac Rehabilitation," Journal of the American College of Cardiology, Nov. 1, 2019, pp. 133-153, vol. 74.
Thomas et al., "Home-Based Cardiac Rehabilitation," HHS Public Access, Oct. 2, 2020, pp. 1-39.
Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.
Chen et al., "Home-based cardiac rehabilitation improves quality of life, aerobic capacity, and readmission rates in patients with chronic heart failure," Medicine, 2018, pp. 1-5 vol. 97:4.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.
Beene et al., "AI and Care Delivery: Emerging Opportunities For Artificial Intelligence To Transform How Care Is Delivered," Nov. 2019, American Hospital Association, pp. 1-12.
Amiya et al., "Is Exercise Training Appropriate for Patients With Advanced Heart Failure Receiving Continuous Inotropic Infusion? A Review," 2018, pp. 1-9, vol. 12, Japan.
Chu Hin Yee, "Physical Activity, Sedentary Behaviour and Health: From Measurements to Recommendations," 2018, 255 pages.
Jeong et al., "Remotely controlled biking is associated with improved adherence to prescribed cycling speed," Technology and Health Care 23, 2015, 7 pages.

(56) References Cited

OTHER PUBLICATIONS

Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.
Blasiak et al., "CURATE.AI: Optimizing Personalized Medicine with Artificial Intelligence, "Slas Technology: Translating Life Sciences Innovation, 2020, 11 pages.
Davenport et al., "The Potential For Artificial Intelligence In Healthcare", 2019, Future Healthcare Journal 2019, vol. 6, No. 2: Year: 2019, pp. 1-5.
Ahmed et al., "Artificial Intelligence With Multi-Functional Machine Learning Platform Development For Better Healthcare And Precision Medicine", 2020, Database (Oxford), 2020:baaa010. doi: 10.1093/database/baaa010 (Year: 2020), pp. 1-35.
Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.
De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.
Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.
Yin Chieh et al., "A Virtual Reality-Cycling Training System for Lower Limb Balance Improvement", BioMed Research International, vol. 2016, pp. 1-10.
Gerbild et al., "Physical Activity to Improve Erectile Dysfunction: A Systematic Review of Intervention Studies," Sexual Medicine, 2018, 15 pages.
International Search Report and Written Opinion for PCT/US2023/014137, dated Jun. 9, 2023, 13 pages.
Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform For Personalized Predictive Analytics", ProQuest LLC, Jul. 2017, 185 pages.
Jeong et al., "Computer-assisted upper extremity training using interactive biking exercise (iBikE) platform," Sep. 2012, pp. 1-5, 34th Annual International Conference of the IEEE EMBS.
"Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12: 1-19. Springer Nature B.V. (Dec. 2017) (Year: 2017)".
Fuller, Carole G.; Diagnosis and treatment considerations with comorbid developmentally disabled populations; Journal of Clinical Psychology 54.1: 1-10. John VWey and Sons Inc. (Jan. 1998) (Year: 1998).
He, Jianxing et al. The practical implementation of artificial intelligence technologies in medicine. Nature Medicine; New York vol. 25, Iss. 1. Jan. 2019. (Year: 2019).
cG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC.2013.2262913. (Year: 2013).
H. Demirkan, "A Smart Healthcare Systems Framework," in IT Professional, vol. 15, No. 5, pp. 38-45, Sep.-Oct. 2013, doi: 10.1109/MITP.2013.35. (Year: 2013).
W. Rashwan, J. Fowler and A. Arisha, "A Multi-Method Scheduling Framework for Medical Staff," 2018 Winter Simulation Conference (WSC), Gothenburg, Sweden, 2018, pp. 1464-1475, doi: 10.1109/WSC.2018.8632247. (Year: 2018)
Marios et al., "The effect of tele-monitoring on exercise training adherence, functional capacity, quality of life and glycemic control in patients with type II diabetes," Journal of Sports Science and Medicine, Mar. 2012, vol. 11, 6 pages.
Shen et al, "Intelligent inverse treatment planning via deep reinforcement learning, a proof-of-principle study in high dose-rate brachytherapy for cervical cancer," pp. 1-17, May 29, 2019, Phys. Med. Biol. vol. 64, No. 115013.
Fraass et al, "The impact of treatment complexity and computer-control delivery technology on treatment delivery errors," pp. 651-659, Oct. 1, 1998, International Journal of Radiation Oncology Biology Physics, vol. 42, Issue 3, https://doi.org/:10.1016/s0360-3016(98)00244-2. PMID: 9806527.
Marchal-Crespo et al, "Review of control strategies for robotic movement training after neurologic injury," pp. 1-15, Jun. 16, 2009, Journal of NeuroEngineering and Rehabilitation, vol. 6, No. 20, https://doi.org/10.1186/1743-0003-6-20.
Karboub et al, "A Machine Learning Based Discharge Prediction of Cardiovascular Diseases Patients in Intensive Care Units.," pp. 1-23, May 24, 2022, Healthcare (Basel, Switzerland) MDPI, vol. 10(6), No. 966, https://doi.org/10.3390/healthcare10060966.
Chrif et al, "Control design for a lower-limb paediatric therapy device using linear motor technology," pp. 119-127, Jun. 9, 2017, Biomedical Usignal Processing and Control, vol. 38, https://www.sciencedirect.com/science/article/pii/S1746809417301027.
International Preliminary Report on Patentability of International Application No. PCT/2024/022550, Date of Mailing Sep. 20, 2025, 7 pages.
Joudaki et al., "Using Data Mining to Detect Health Care Fraud and Abuse: A Review of Literature", Global Journal of Health Science, vol. 7, No. 1, 2015 (Year: 2015).

* cited by examiner

SYSTEM AND METHOD FOR GENERATING TREATMENT PLANS TO ENHANCE PATIENT RECOVERY BASED ON SPECIFIC OCCUPATIONS

CROSS-REFERENCES TO RELATED APPLICATIONS

This application is a continuation-in-part of U.S. patent application Ser. No. 17/739,906 filed May 9, 2022, titled "Systems and Methods for Using Machine Learning to Control an Electromechanical Device Used for Prehabilitation, Rehabilitation, and/or Exercise", which is a continuation of U.S. patent application Ser. No. 17/150,938, filed Jan. 15, 2021, titled "Systems and Methods for Using Machine Learning to Control an Electromechanical Device Used for Prehabilitation, Rehabilitation, and/or Exercise", which is a continuation-in-part of U.S. patent application Ser. No. 17/021,895, filed Sep. 15, 2020, titled "Telemedicine for Orthopedic Treatment", which claims priority to and the benefit of U.S. Provisional Patent Application Ser. No. 62/910,232, filed Oct. 3, 2019, titled "Telemedicine for Orthopedic Treatment", the entire disclosures of which are hereby incorporated by reference for all purposes. U.S. patent application Ser. No. 17/150,938, also claims priority to and the benefit of U.S. Provisional Patent Application Ser. No. 63/066,488, filed Aug. 17, 2020, titled "Systems and Methods for Using Machine Learning to Control an Electromechanical Device Used for Prehabilitation and/or Exercise", the entire disclosure of which is hereby incorporated by reference for all purposes.

This application also claims priority to and the benefit of U.S. Provisional Patent Application Ser. No. 63/194,684, filed May 28, 2021, titled "System and Method for Generating Treatment Plans to Enhance Patient Recovery Based on Specific Occupations", the entire disclosure of which is hereby incorporated by reference for all purposes.

This application is also a continuation of International Application No. PCT/US22/31023, filed May 26, 2022, titled "System and Method for Generating Treatment Plans to Enhance Patient Recovery Based on Specific Occupations", the entire disclosure of which is hereby incorporated by reference for all purposes.

BACKGROUND

Remote medical assistance, or telemedicine, may aid a patient in performing various aspects of a rehabilitation regimen for a body part. The patient may use a patient interface in communication with a healthcare professional interface for receiving the remote medical assistance via audio and/or audiovisual communications.

SUMMARY

In one embodiment, a computer-implemented system is disclosed. The system includes a treatment apparatus configured to be manipulated by a user while the user performs a treatment plan. The system includes a patient interface associated with the user. The system includes a server computing device configured to generate the treatment plan that includes at least one modified attribute of the user. The at least one modified attribute of the user is associated with at least one attribute of an occupational task. The server computing device is configured to receive data associated with the user. The data includes the at least one modified attribute of the user and the at least one attribute of the occupational task. The server computing device is configured to access a database including data associated with one or more exercises associated with the at least one modified attribute of the user and the at least one attribute of the occupational task. The server computing device is configured to generate, via an artificial intelligence engine, the treatment plan, wherein the treatment plan includes at least one exercise of the one or more exercises associated with the at least one modified attribute of the first user and the at least one attribute of the occupational task. The artificial intelligence engine generates the treatment plan, wherein the treatment plan includes the at least one exercise based on the data associated with the user and the data associated with the one or more exercises.

In one embodiment, a computer-implemented method is disclosed. The method includes generating a treatment plan to modify at least one attribute of a user. The at least one attribute of the user is associated with at least one attribute of an occupational task. The method includes receiving data associated with the user. The data includes the at least one modified attribute of the user and the at least one attribute of the occupational task. The method includes accessing a database including data associated with one or more exercises associated with the at least one modified attribute of the user and the at least one attribute of the occupational task. The method includes generating, via an artificial intelligence engine, the treatment plan, wherein the treatment plan includes at least one exercise of the one or more exercises associated with the at least one modified attribute of the first user and the at least one attribute of the occupational task. The artificial intelligence engine generates the treatment plan, wherein the treatment plan includes the at least one exercise based on the data associated with the user and the data associated with the one or more exercises.

In one embodiment, a tangible, non-transitory computer-readable medium stores instructions that, when executed, cause a processing device to perform any of the methods, operations, or steps described herein.

BRIEF DESCRIPTION OF THE DRAWINGS

For a detailed description of example embodiments, reference will now be made to the accompanying drawings in which.

NOTATION AND NOMENCLATURE

Figure 1:
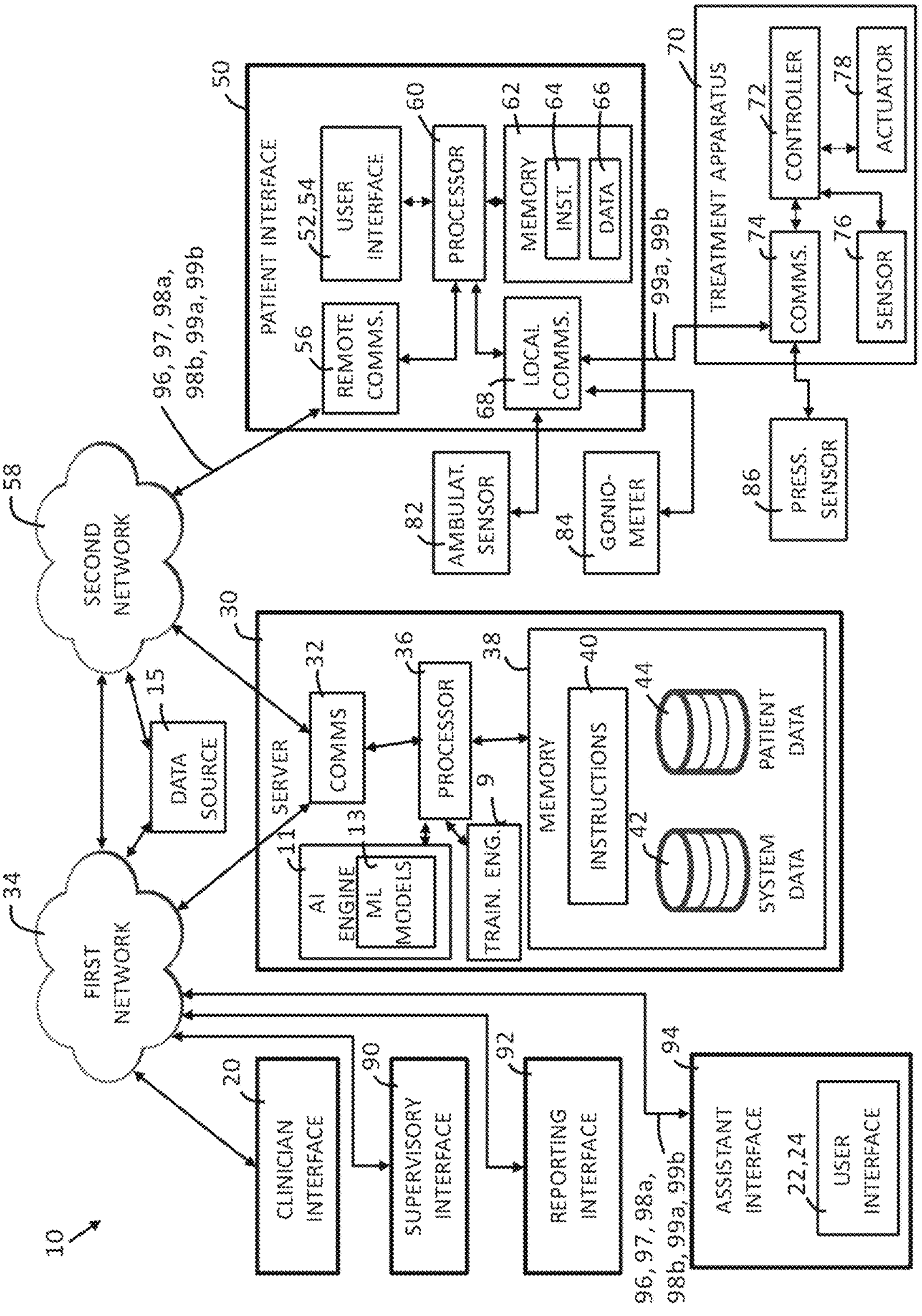
FIG. 1 shows a block diagram of an embodiment of a computer implemented system for managing a treatment plan according to the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or a direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment apparatus, a diet regimen for the patient, a medication regimen for the patient, a sleep regimen for the patient, additional regimens, or some combination thereof.

The terms telemedicine, telehealth, telemed, teletherapeutic, etc. may be used interchangeably herein.

The term "attribute of a user" may include a quality or feature regarded as a characteristic or inherent part of someone.

The term "attribute of an occupational task" may include that which is regarded as required of and/or desired in any person to perform an occupational task, such as a physical, cognitive, attentional, or communication capability. One or more attributes may be associated with an occupational task.

Some embodiments are described in connection with thresholds. As used herein, an indication that a threshold condition may be or has been satisfied may refer to a value being greater than a threshold condition, greater than or the same as a threshold condition, the same as a threshold condition, smaller than or the same as a threshold condition, smaller than a threshold condition, above a threshold condition, above or at a threshold condition, at a threshold condition, below or at a threshold condition, below a threshold condition, or the like. In some embodiments, the threshold condition may be configurable by the patient and/or a healthcare professional.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining a treatment plan for a patient having certain attributes (e.g., vital-sign or other measurements; performance; demographic; geographic; diagnostic; measurement- or test-based; medically historic; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include attributes of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, or some combination thereof. The measurement information may include, e.g., a vital sign, a respiration rate, a heartrate, a temperature, a blood pressure, or some combination thereof. It may be desirable to process the attributes of a multitude of patients, the treatment plans performed for those patients, and the results of the treatment plans for those patients.

Further, another technical problem may involve distally treating, via a computing device during a telemedicine or telehealth session, a patient from a location different from a location at which the patient is located. An additional technical problem is controlling or enabling the control of, from the different location, a treatment apparatus used by the patient at the location at which the patient is located. Oftentimes, when a patient undergoes rehabilitative surgery (e.g., knee surgery), a physical therapist or other healthcare professional may prescribe a treatment apparatus to the patient to use to perform a treatment protocol at their residence or any mobile location or temporary domicile. A healthcare professional may refer to a doctor, physician assistant, nurse, chiropractor, dentist, physical therapist, acupuncturist, physical trainer, or the like. A healthcare professional may refer to any person with a credential, license, degree, or the like in the field of medicine, physical therapy, rehabilitation, or the like.

Since the physical therapist or other healthcare professional is located in a different location from the patient and the treatment apparatus, it may be technically challenging for the physical therapist or other healthcare professional to monitor the patient's actual progress (as opposed to relying on the patient's word about their progress) using the treatment apparatus, modify the treatment plan according to the patient's progress, adapt the treatment apparatus to the personal attributes of the patient as the patient performs the treatment plan, and the like.

Accordingly, embodiments of the present disclosure pertain to using artificial intelligence and/or machine learning to assign patients to cohorts and to dynamically control a treatment apparatus based on the assignment during an adaptive telemedical session. In some embodiments, numerous treatment apparatuses may be provided to patients. The treatment apparatuses may be used by the patients to perform treatment plans in their residences, at a gym, at a rehabilitative center, at a hospital, or any suitable location, including permanent or temporary domiciles. In some embodiments, the treatment apparatuses may be communicatively coupled to a server. Attributes of the patients may be collected before, during, and/or after the patients perform the treatment plans. For example, the personal information, the performance information, and the measurement information may be collected before, during, and/or after the person performs the treatment plans. The results (e.g., improved performance or decreased performance) of performing each exercise may be collected from the treatment apparatus throughout the treatment plan and after the treatment plan is performed. The parameters, settings, configurations, etc. (e.g., position of pedal, amount of resistance, etc.) of the treatment apparatus may be collected before, during, and/or after the treatment plan is performed.

Each attribute of the patient, each result, and each parameter, setting, configuration, etc. may be timestamped and may be correlated with a particular step in the treatment plan. Such a technique may enable determining which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment apparatuses and/or any suitable computing device (e.g., computing devices where personal information is entered, such as a clinician interface or patient interface) over time as the patients use the treatment apparatuses to perform the various treatment plans. The data that may be collected may include the attributes of the patients, the treatment plans performed by the patients, and the results of the treatment plans.

In some embodiments, the data may be processed to group certain people into cohorts. The people may be grouped by people having certain or selected similar attributes, treatment plans, and results of performing the treatment plans. For example, athletic people having no medical conditions who perform a treatment plan (e.g., use the treatment apparatus for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. For example, the one or more machine learning models may be trained to receive an input of attributes of a new patient and to output a treatment plan for the patient that results in a desired result. The machine learning models may match a pattern between the attributes of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment apparatus while the new patient uses the treatment apparatus to perform the treatment plan.

As may be appreciated, the attributes of the new patient may change as the new patient uses the treatment apparatus to perform the treatment plan. For example, the performance of the patient may improve quicker than expected for people in the cohort to which the new patient is currently assigned. Accordingly, the machine learning models may be trained to dynamically reassign, based on the changed attributes, the new patient to a different cohort that includes people having attributes similar to the now-changed attributes as the new patient. For example, a clinically obese patient may lose weight and no longer meet the weight criterion for the initial cohort, result in the patient being reassigned to a different cohort with a different weight criterion. A different treatment plan may be selected for the new patient, and the treatment apparatus may be controlled, distally and based on the different treatment plan, the treatment apparatus while the new patient uses the treatment apparatus to perform the treatment plan. Such techniques may provide the technical solution of distally controlling a treatment apparatus. Further, the techniques may lead to faster recovery times and/or better results for the patients because the treatment plan that most accurately fits their attributes is selected and implemented, in real-time, at any given moment. "Real-time" may also refer to near real-time, which may be less than 10 seconds. As described herein, the term "results" may refer to medical results or medical outcomes. Results and outcomes may refer to responses to medical actions.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with attributes similar to the patient's, and that a second treatment plan provides the second result for people with attributes similar to the patient.

Further, the artificial intelligence engine may also be trained to output treatment plans that are not optimal or sub-optimal or even inappropriate (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient.

In some embodiments, the treatment plans and/or excluded treatment plans may be presented, during a telemedicine or telehealth session, to a healthcare professional. The healthcare professional may select a particular treatment plan for the patient to cause that treatment plan to be transmitted to the patient and/or to control, based on the treatment plan, the treatment apparatus. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment apparatus. In such cases, the recommended treatment plans and/or excluded treatment plans may be presented simultaneously with a video of the patient in real-time or near real-time during a telemedicine or telehealth session on a user interface of a computing device of a healthcare professional. The video may also be accompanied by audio, text and other multimedia information. Real-time may refer to less than or equal to 2 seconds. Near real-time may refer to any interaction of a sufficiently short time to enable two individuals to engage in a dialogue via such user interface, and will generally be less than 10 seconds but greater than 2 seconds.

Presenting the treatment plans generated by the artificial intelligence engine concurrently with a presentation of the patient video may provide an enhanced user interface because the healthcare professional may continue to visually and/or otherwise communicate with the patient while also reviewing the treatment plans on the same user interface. The enhanced user interface may improve the healthcare professional's experience using the computing device and may encourage the healthcare professional to reuse the user interface. Such a technique may also reduce computing resources (e.g., processing, memory, network) because the healthcare professional does not have to switch to another user interface screen to enter a query for a treatment plan to recommend based on the attributes of the patient. The artificial intelligence engine provides, dynamically on the fly, the treatment plans and excluded treatment plans.

In some embodiments, the treatment apparatus may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare professional may adapt, remotely during a telemedicine session, the treatment apparatus to the needs of the patient by causing a control instruction to be transmitted from a server to treatment apparatus. Such adaptive nature may improve the results of recovery for a patient, furthering the goals of personalized medicine, and enabling personalization of the treatment plan on a per-individual basis.

FIG. 1 shows a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

In addition, the attributes (e.g., personal, performance, measurement, etc.) of the people, the treatment plans followed by the people, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, a first occupational task or tasks, and a first result of the treatment plan may be stored in a first patient database. The data for a second cohort of second patients having a second similar injury, a second similar medical condition, a second similar medical procedure performed, a second treatment plan followed by the second patient, a second occupational task or tasks, and a second result of the treatment plan may be stored in a second patient database. Any single attribute or any combination of attributes may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This attribute data, occupational task attribute data, treatment plan data, and results data may be obtained from numerous treatment apparatuses and/or computing devices over time and stored in the database 44. The attribute data, occupational task attribute data, treatment plan data, and results data may be correlated in the patient-cohort databases in the patient data store 44. The attributes of the people may include personal information, performance information, and/or measurement information.

In addition to the historical information about other people stored in the patient cohort-equivalent databases, real-time or near-real-time information based on the current patient's attributes about a current patient being treated may be stored in an appropriate patient cohort-equivalent database. The attributes of the patient may be determined to match with or be regarded as similar to the attributes of another person in a particular cohort (e.g., cohort A), and the attributes of occupational tasks associated with the patient may be determined to match with or regarded as similar to the attributes of the occupational tasks associated with another person in the particular cohort, and the patient may be assigned to that cohort.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their attributes, attributes of occupational tasks associated with the people, select treatment plans using real-time and historical data correlations involving patient cohort-equivalents, and control a treatment apparatus 70, among other things. The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based or a real-time software platform, and it may include privacy software or protocols, and/or security software or protocols.

To train the one or more machine learning models 13, the training engine 9 may use a training data set of a corpus of the attributes of the people that used the treatment apparatus 70 to perform treatment plans, the attributes of the occupational tasks of the people, the details (e.g., treatment protocol including exercises, amount of time to perform the exercises, how often to perform the exercises, a schedule of exercises, parameters/configurations/settings of the treatment apparatus 70 throughout each step of the treatment plan, etc.) of the treatment plans performed by the people using the treatment apparatus 70, and the results of the treatment plans performed by the people. The one or more machine learning models 13 may be trained to match patterns of attributes of a patient with attributes of other people assigned to a particular cohort and to match patterns of attributes of occupational tasks of the patient with attributes of occupational tasks of other people assigned to the particular cohort.

As used throughout this disclosure, the terms "match", "match with", "matches with" may refer to an exact match, a correlative match, a substantial match, etc.

The one or more machine learning models 13 may be trained to receive the attributes of a patient and attributes of occupational tasks associated with the patient as input, map the attributes to attributes of people assigned to a cohort and to attributes of occupational tasks of the people assigned to the cohort, and select a treatment plan from that cohort. The one or more machine learning models 13 may also be trained to control, based on the treatment plan, the machine learning apparatus 70.

Different machine learning models 13 may be trained to recommend different treatment plans for different desired results. For example, one machine learning model may be trained to recommend treatment plans for most effective recovery, while another machine learning model may be trained to recommend treatment plans based on speed of recovery.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., healthcare professional interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment apparatus 70 may be any suitable medical, rehabilitative, therapeutic, etc. apparatus configured to be controlled distally via another computing device to treat a patient and/or exercise the patient. The treatment apparatus 70 may be an electromechanical machine including one or more weights, an electromechanical bicycle, an electromechanical spin-wheel, a smart-mirror, a treadmill, or the like. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating attributes of the treatment apparatus 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes a healthcare professional interface 94 for a healthcare professional, such as a doctor, a nurse, a physical therapist, or a technician, to remotely communicate with the patient interface 50 and/or the treatment apparatus 70. Such remote communications may enable the healthcare professional to provide assistance or guidance to a patient using the system 10. More specifically, the healthcare professional interface 94 is configured to communicate a telemedicine signal 96, 97, 98*a*, 98*b*, 99*a*, 99*b* with the patient interface 50 via a network connection such as, for example, via the first network 34 and/or the second network 58. The telemedicine signal 96, 97, 98*a*, 98*b*, 99*a*, 99*b* comprises one of an audio signal 96, an audiovisual signal 97, an interface control signal 98*a* for controlling a function of the patient interface 50, an interface monitor signal 98*b* for monitoring a status of the patient interface 50, an apparatus control signal 99*a* for changing an operating parameter of the treatment apparatus 70, and/or an apparatus monitor signal 99*b* for monitoring a status of the treatment apparatus 70. In some embodiments, each of the control signals 98*a*, 99*a* may be unidirectional, conveying commands from the healthcare professional interface 94 to the patient interface 50. In some embodiments, in response to successfully receiving a control signal 98*a*, 99*a* and/or to communicate successful and/or unsuccessful implementation of the requested control action, an acknowledgement message may be sent from the patient interface 50 to the healthcare professional interface 94. In some embodiments, each of the monitor signals 98*b*, 99*b* may be unidirectional, status-information commands from the patient interface 50 to the healthcare professional interface 94. In some embodiments, an acknowledgement message may be sent from the healthcare professional interface 94 to the patient interface 50 in response to successfully receiving one of the monitor signals 98*b*, 99*b*.

In some embodiments, the patient interface 50 may be configured as a pass-through for the apparatus control signals 99*a* and the apparatus monitor signals 99*b* between the treatment apparatus 70 and one or more other devices, such as the healthcare professional interface 94 and/or the server 30. For example, the patient interface 50 may be configured to transmit an apparatus control signal 99*a* in response to an apparatus control signal 99*a* within the telemedicine signal 96, 97, 98*a*, 98*b*, 99*a*, 99*b* from the healthcare professional interface 94.

In some embodiments, the healthcare professional interface 94 may be presented on a shared physical device as the clinician interface 20. For example, the clinician interface 20 may include one or more screens that implement the healthcare professional interface 94. Alternatively or additionally, the clinician interface 20 may include additional hardware components, such as a video camera, a speaker, and/or a microphone, to implement aspects of the healthcare professional interface 94.

In some embodiments, one or more portions of the telemedicine signal 96, 97, 98*a*, 98*b*, 99*a*, 99*b* may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the healthcare professional interface 94, the healthcare professional may cause content from the prerecorded source to be played on the patient interface 50.

The healthcare professional interface 94 includes a healthcare professional input device 22 and a healthcare professional display 24, which may be collectively called a healthcare professional user interface 22, 24. The healthcare professional input device 22 may include one or more of a telephone, a keyboard, a mouse, a trackpad, or a touch screen, for example. Alternatively or additionally, the healthcare professional input device 22 may include one or more microphones. In some embodiments, the one or more microphones may take the form of a telephone handset, headset, or wide-area microphone or microphones configured for the healthcare professional to speak to a patient via the patient interface 50. In some embodiments, healthcare professional input device 22 may be configured to provide voice-based functionalities, with hardware and/or software configured to interpret spoken instructions by the healthcare professional by using the one or more microphones. The healthcare professional input device 22 may include functionality provided by or similar to existing voice-based assistants such as Siri by Apple, Alexa by Amazon, Google Assistant, or Bixby by Samsung. The healthcare professional input device 22 may include other hardware and/or software components. The healthcare professional input device 22 may include one or more general-purpose devices and/or special-purpose devices.

The healthcare professional display 24 may take one or more different forms including, for example, a computer monitor or display screen on a tablet, a smartphone, or a smart watch. The healthcare professional display 24 may include other hardware and/or software components such as projectors, virtual reality capabilities, or augmented reality capabilities, etc. The healthcare professional display 24 may incorporate various different visual, audio, or other presentation technologies. For example, the healthcare professional display 24 may include a non-visual display, such as an audio signal, which may include spoken language and/or other sounds such as tones, chimes, melodies, and/or compositions, which may signal different conditions and/or directions. The healthcare professional display 24 may comprise one or more different display screens presenting various data and/or interfaces or controls for use by the healthcare professional. The healthcare professional display 24 may include graphics, which may be presented by a web-based interface and/or by a computer program or application (App.).

In some embodiments, the system 10 may provide computer translation of language from the healthcare professional interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the healthcare professional. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the healthcare professional display 24 for presentation by the healthcare professional interface 94. For example, the server 30 may include a web server configured to generate the display screens for presentation upon the healthcare professional display 24. For example, the artificial intelligence engine 11 may generate recommended treatment plans and/or excluded treatment plans for patients and generate the display screens including those recommended treatment plans and/or external treatment plans for presentation on the healthcare professional display 24 of the healthcare professional interface 94. In some embodiments, the healthcare professional display 24 may be configured to present a virtualized desktop hosted by the server 30. In some embodiments, the server 30 may be configured to communicate with the healthcare professional interface 94 via the first network 34. In some embodiments, the first network 34 may include a local area network (LAN), such as an Ethernet network. In some embodiments, the first network 34 may include the Internet, and communications between the server 30 and the healthcare professional interface 94 may be secured via privacy enhancing technologies, such as, for example, by using encryption over a virtual private network (VPN). Alternatively or additionally, the server 30 may be configured to communicate with the healthcare professional interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the healthcare professional interface 94. For example, the patient interface 50 and the treatment apparatus 70 may be used as part of an in-home rehabilitation system, which may be aided remotely by using the healthcare professional interface 94 at a centralized location, such as a clinic or a call center.

In some embodiments, the healthcare professional interface 94 may be one of several different terminals (e.g., computing devices) that may be grouped together, for example, in one or more call centers or at one or more clinicians' offices. In some embodiments, a plurality of healthcare professional interfaces 94 may be distributed geographically. In some embodiments, a person may work as a healthcare professional remotely from any conventional office infrastructure. Such remote work may be performed, for example, where the healthcare professional interface 94 takes the form of a computer and/or telephone. This remote work functionality may allow for work-from-home arrangements that may include part time and/or flexible work hours for a healthcare professional.

Figure 2:
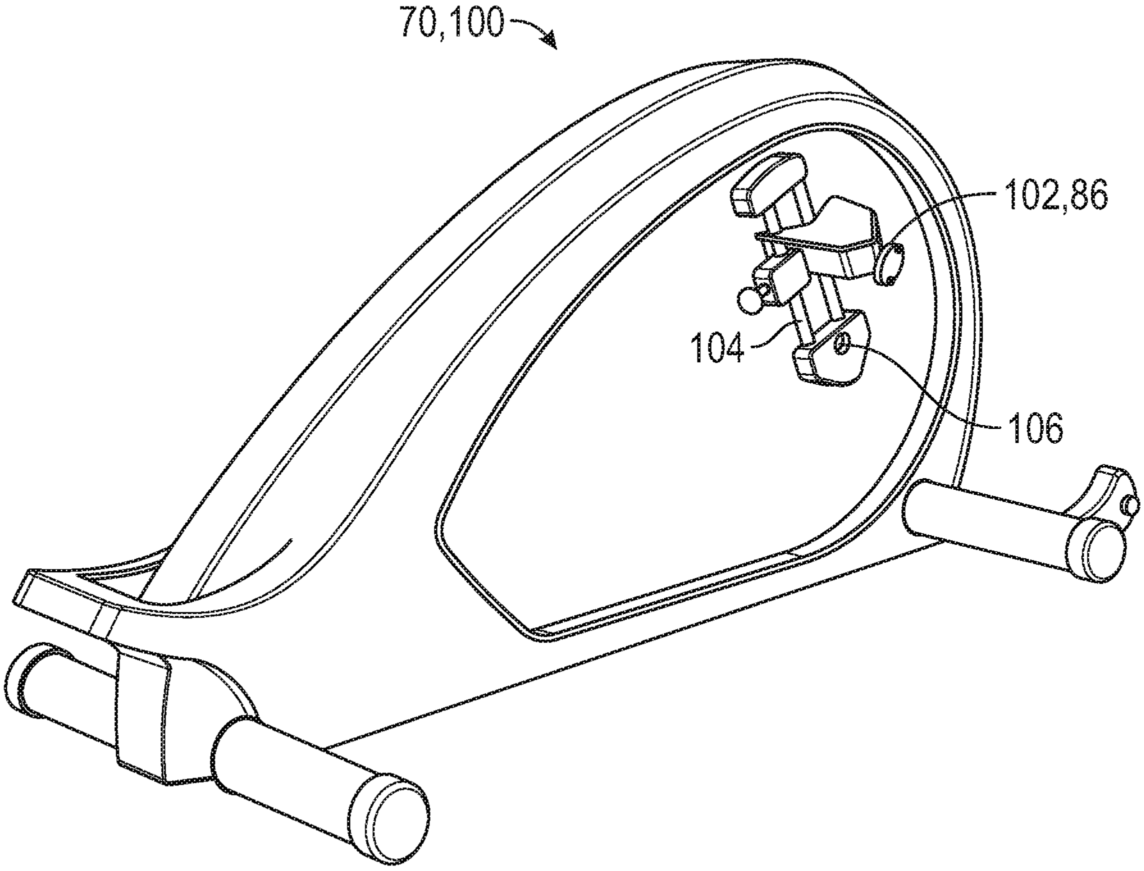
FIG. 2 shows a perspective view of an embodiment of a treatment apparatus according to the present disclosure.
Figure 3:
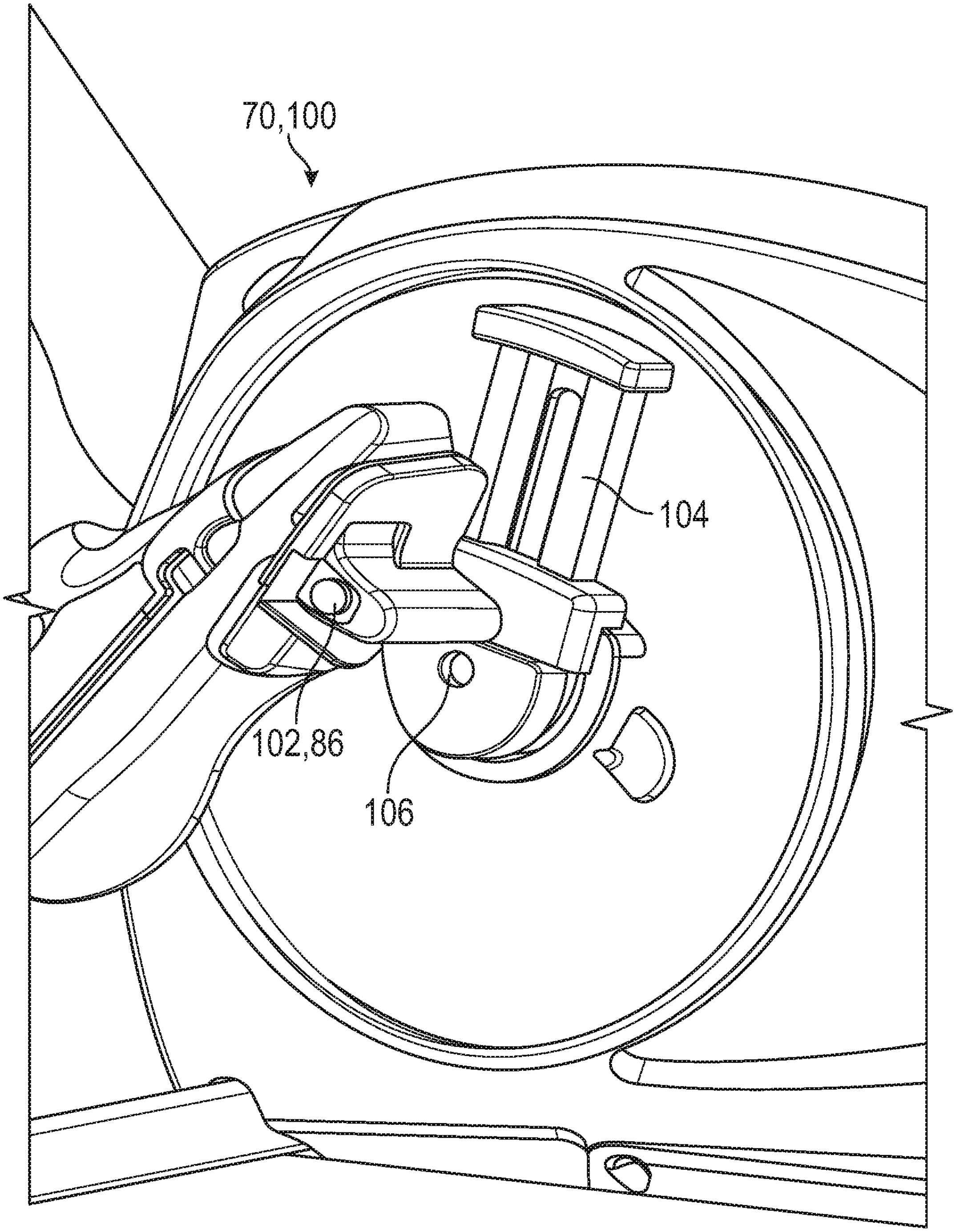
FIG. 3 shows a perspective view of a pedal of the treatment apparatus of FIG. 2 according to the present disclosure.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
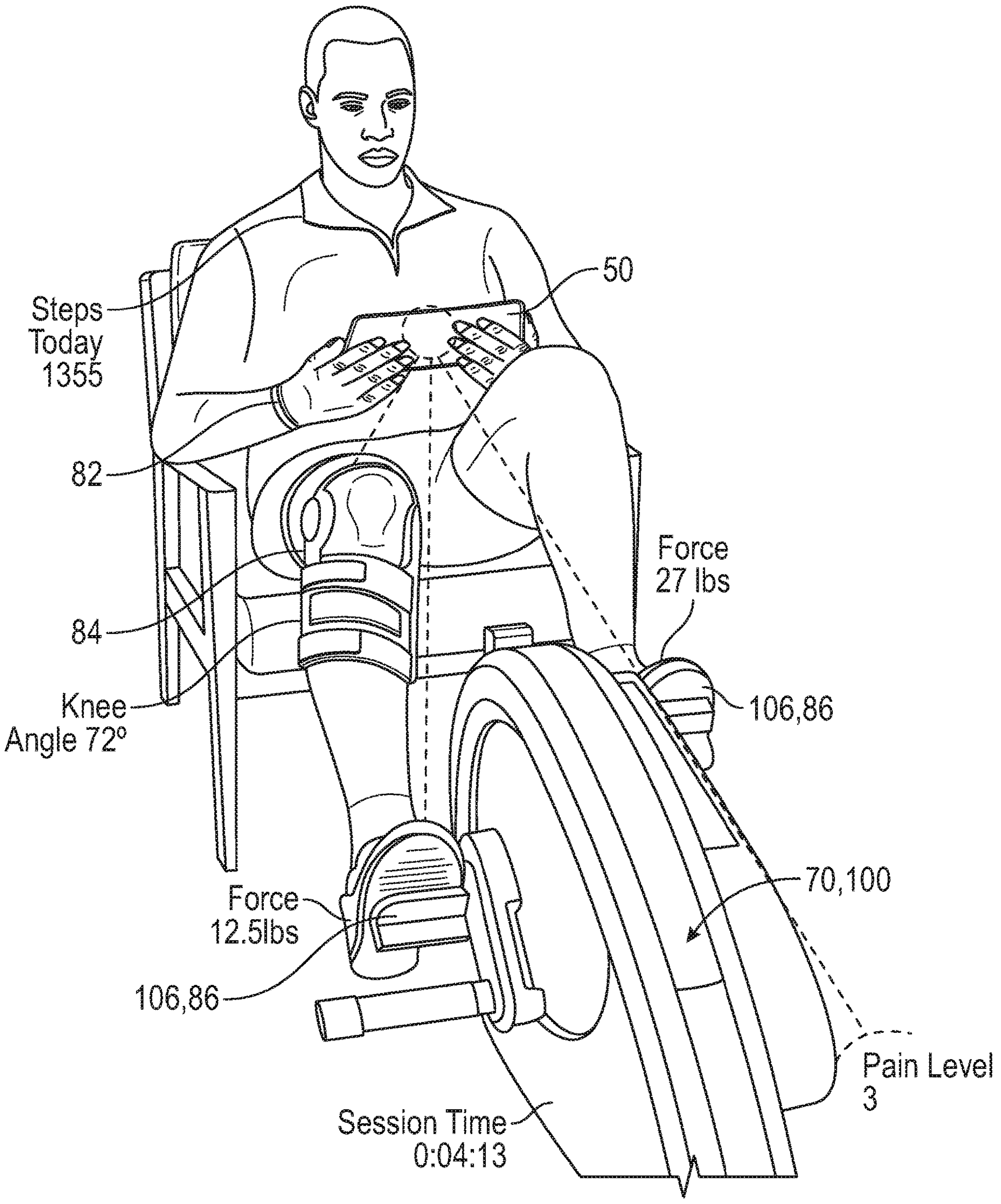
FIG. 4 shows a perspective view of a person using the treatment apparatus of FIG. 2 according to the present disclosure.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

Figure 5:
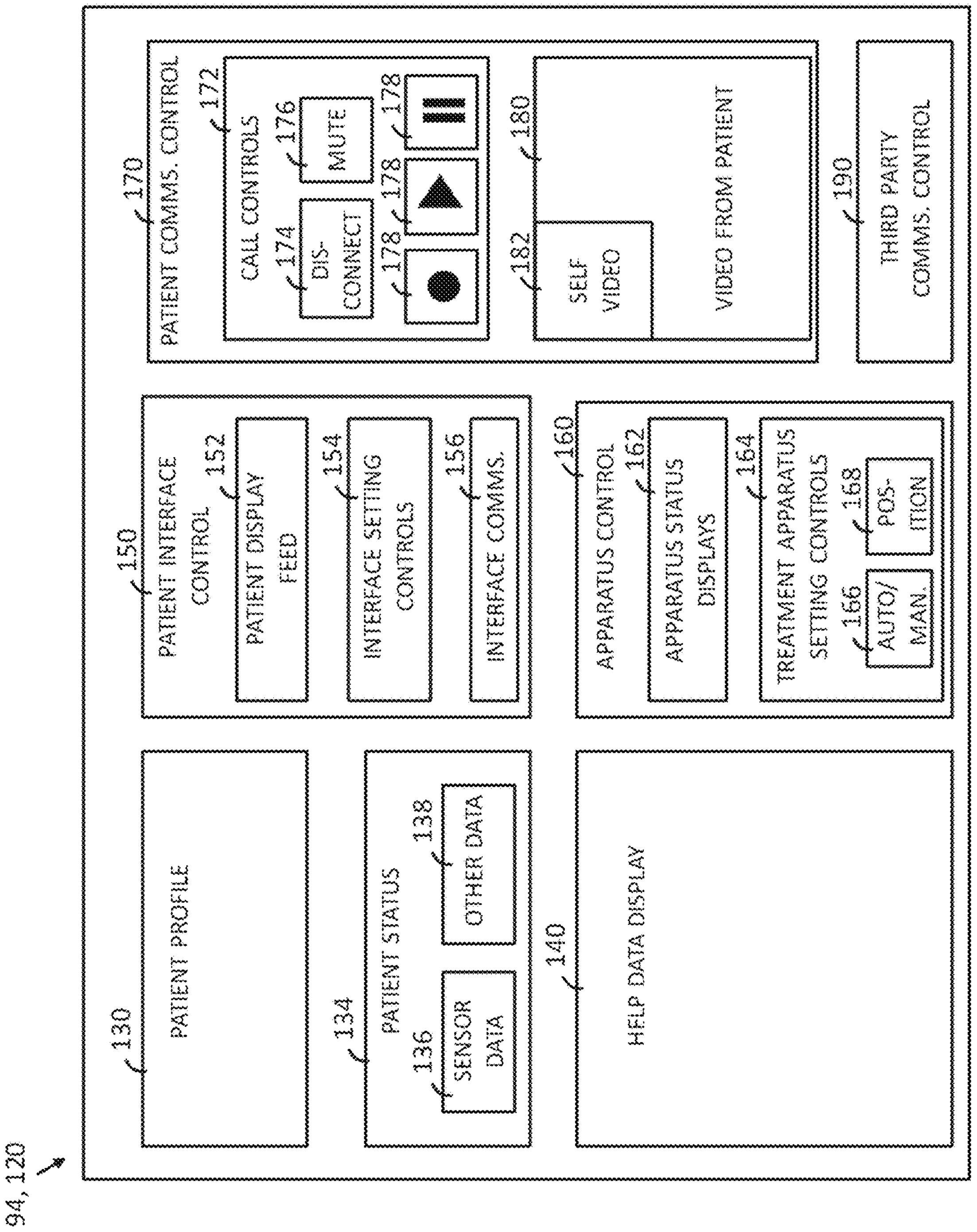
FIG. 5 shows an example embodiment of an overview display of a healthcare professional interface according to the present disclosure.

FIG. 5 is an example embodiment of an overview display 120 of the healthcare professional interface 94. Specifically, the overview display 120 presents several different controls and interfaces for the healthcare professional to remotely assist a patient with using the patient interface 50 and/or the treatment apparatus 70. This remote assistance functionality may also be called telemedicine or telehealth.

Specifically, the overview display 120 includes a patient profile display 130 presenting biographical information regarding a patient using the treatment apparatus 70. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information. More specifically, the data presented upon the patient profile display 130 may depend upon the healthcare professional's need for that information. For example, a healthcare professional that is assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment apparatus 70. Such treatment plan information may be limited to a healthcare professional who has a certain level of authority, such as a doctor or physical therapist. For example, a healthcare professional who is a doctor assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended treatment plans with corresponding predicted estimates of when the patient would be capable of performing the occupational task(s) associated with the patient and/or excluded treatment plans may be presented in the patient profile display 130 to the healthcare professional. The one or more recommended treatment plans with predicted estimates and/or excluded treatment plans may be generated by the artificial intelligence engine 11 of the server 30 and received from the server 30 in real-time during, inter alia, a telemedicine or telehealth session. An example of presenting the one or more recommended treatment plans and predicted estimates and/or excluded treatment plans is described below with reference to FIG. 7.

The example overview display 120 shown in FIG. 5 also includes a patient status display 134 presenting status information regarding a patient using the treatment apparatus 70. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the healthcare professional interface 94 may be controlled by user access controls, with permissions set depending on the healthcare professional/user's need for and/or qualifications to view that information.

The example overview display 120 shown in FIG. 5 also includes a help data display 140 presenting information for the healthcare professional to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the healthcare professional to use in determining a root cause and/or solution to a patient's problem. In some embodiments, the healthcare professional interface 94 may present two or more help data displays 140, which may be the same or different, for simultaneous presentation of help data for use by the healthcare professional. for example, a first help data display may be used to present a troubleshooting flowchart to determine the source of a patient's problem, and a second help data display may present script information for the healthcare professional to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or to modify one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the healthcare professional interface 94 via one or more of the interface monitor signals 98*b*. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the healthcare professional to adjust or to control one or more settings or aspects of the patient interface 50. In some embodiments, the patient interface setting control 154 may cause the healthcare professional interface 94 to generate and/or to transmit an interface control signal 98 for controlling a function or a setting of the patient interface 50.

In some embodiments, the patient interface setting control 154 may include collaborative browsing or co-browsing capability for the healthcare professional to remotely view and/or control the patient interface 50. For example, the patient interface setting control 154 may enable the healthcare professional to remotely enter text to one or more text entry fields on the patient interface 50 and/or to remotely control a cursor on the patient interface 50 using a mouse or touchscreen of the healthcare professional interface 94.

In some embodiments, using the patient interface 50, the patient interface setting control 154 may allow the healthcare professional to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the healthcare professional to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the healthcare professional to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the healthcare professional to remotely modify communications with one or more of the other devices 70, 82, 84. For example, the healthcare professional may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the healthcare professional to view and/or to control information regarding the treatment apparatus 70. The apparatus control 160 may take the form of a portion or region of the overview display 120, as shown in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the healthcare professional interface 94 via one or more of the apparatus monitor signals 99*b*. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the healthcare professional to adjust or control one or more aspects of the treatment apparatus 70. The apparatus setting control 164 may cause the healthcare professional interface 94 to generate and/or to transmit an apparatus control signal 99 for changing an operating parameter of the treatment apparatus 70, (e.g., a pedal radius setting, a resistance setting, a target RPM, etc.). The apparatus setting control 164 may include a mode button 166 and a position control 168, which may be used in conjunction for the healthcare professional to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, and without having an associated auto/manual mode. In some embodiments, the healthcare professional may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the healthcare professional to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the healthcare professional to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a live feed from the healthcare professional interface 94 for presentation by the output device of the patient interface 50. The live feed may take the form of an audio feed and/or a video feed. In some embodiments, the patient interface 50 may be configured to provide two-way audio or audiovisual communications with a person using the healthcare professional interface 94. Specifically, the communications session with the patient interface 50 may include bidirectional (two-way) video or audiovisual feeds, with each of the patient interface 50 and the healthcare professional interface 94 presenting video of the other one. In some embodiments, the patient interface 50 may present video from the healthcare professional interface 94, while the healthcare professional interface 94 presents only audio or the healthcare professional interface 94 presents no live audio or visual signal from the patient interface 50. In some embodiments, the healthcare professional interface 94 may present video from the patient interface 50, while the patient interface 50 presents only audio or the patient interface 50 presents no live audio or visual signal from the healthcare professional interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as a separate screen or a popup window. The audio and/or audiovisual communications may be processed and/or directed by the healthcare professional interface 94 and/or by another device or devices, such as a telephone system, or a videoconferencing system used by the healthcare professional while the healthcare professional uses the healthcare professional interface 94. Alternatively or additionally, the audio and/or audiovisual communications may include communications with a third party. For example, the system 10 may enable the healthcare professional to initiate a 3-way conversation regarding use of a particular piece of hardware or software, with the patient and a subject matter expert, such as a healthcare professional or a specialist. The example patient communications control 170 shown in FIG. 5 includes call controls 172 for the healthcare professional to use in managing various aspects of the audio or audiovisual communications with the patient. The call controls 172 include a disconnect button 174 for the healthcare professional to end the audio or audiovisual communications session. The call controls 172 also include a mute button 176 to temporarily silence an audio or audiovisual signal from the healthcare professional interface 94. In some embodiments, the call controls 172 may include other features, such as a hold button (not shown). The call controls 172 also include one or more record/playback controls 178, such as record, play, and pause buttons to control, with the patient interface 50, recording and/or playback of audio and/or video from the teleconference session. The call controls 172 also include a video feed display 180 for presenting still and/or video images from the patient interface 50, and a self-video display 182 showing the current image of the healthcare professional using the healthcare professional interface. The self-video display 182 may be presented as a picture-in-picture format, within a section of the video feed display 180, as shown in FIG. 5. Alternatively or additionally, the self-video display 182 may be presented separately and/or independently from the video feed display 180.

The example overview display 120 shown in FIG. 5 also includes a third party communications control 190 for use in conducting audio and/or audiovisual communications with a third party. The third party communications control 190 may take the form of a portion or region of the overview display 120, as shown in FIG. 5. The third party communications control 190 may take other forms, such as a display on a separate screen or a popup window. The third party communications control 190 may include one or more controls, such as a contact list and/or buttons or controls to contact a third party regarding use of a particular piece of hardware or software, e.g., a subject matter expert, such as a healthcare professional or a specialist. The third party communications control 190 may include conference calling capability for the third party to simultaneously communicate with both the healthcare professional via the healthcare professional interface 94, and with the patient via the patient interface 50. For example, the system 10 may provide for the healthcare professional to initiate a 3-way conversation with the patient and the third party.

Figure 6:
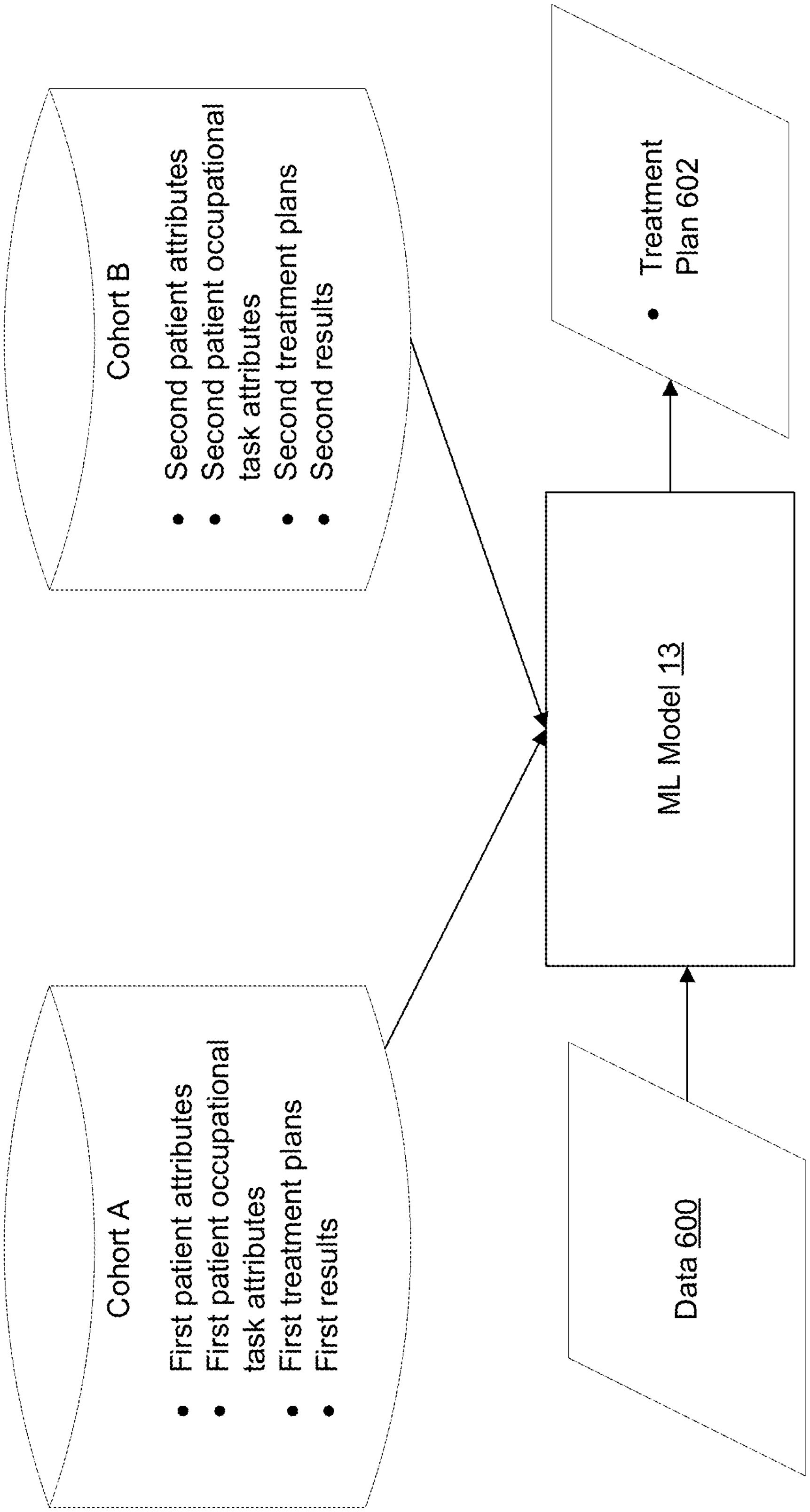
FIG. 6 shows an example block diagram of training the machine learning model to output, based on data pertaining to the user and data pertaining to an occupational task associated with the patient, a treatment plan including exercises associated with a modified attribute of the user.

FIG. 6 shows an example block diagram of training a machine learning model 13 to output, based on data 600 pertaining to the patient and to the occupational task(s) associated with the patient, a treatment plan 602 for the patient and a predicted estimate 603 of when the patient performing treatment plan 602 would be capable of performing the occupational task(s) associated with the patient, according to the present disclosure. Data pertaining to other patients may be received by the server 30. The other patients may have used various treatment apparatuses to perform treatment plans. The data may include attributes of the other patients, attributes of occupational tasks of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first attributes, first attributes of occupational tasks, first treatment plans, and first results. Cohort B includes data for patients having similar second attributes, second attributes of occupational tasks, second treatment plans, and second results. For example, cohort A may include first attributes of patients in their twenties without any medical conditions who tore a leg ligament while lifting boxes from trucks in a warehouse; their treatment plans may include a certain treatment protocol (e.g., use the treatment apparatus 70 for 30 minutes 5 times a week for a predicted estimate of time, wherein values for the properties, configurations, and/or settings of the treatment apparatus 70 are set to X (where X is a numerical value) for a first portion of the predicted estimate of time and to Y (where Y is a numerical value) for a second portion of the predicted estimate of time).

In some embodiments, the attributes of occupational tasks (e.g., lifting boxes, moving boxes, operating a machine, etc.) in cohort A and cohort B may include attributes not associated with an injury. For example, the attributes of a warehouse employee may specify that the employee has a certain strength level, a certain endurance, etc. The database may store exercises associated with achieving the certain strength level, endurance level, etc. and a treatment plan generated by the artificial intelligence engine 11 may include those exercises.

Cohort A and cohort B may be included in a training dataset used to train the machine learning model 13. The machine learning model 13 may be trained to match a pattern between attributes for each cohort and output the treatment plan that provides the result, and/or the corresponding predicted estimate. Accordingly, when the data 600 for a new patient is input into the trained machine learning model 13, the trained machine learning model 13 may match the attributes included in the data 600 with attributes in either cohort A or cohort B and output the appropriate treatment plan 602 and the corresponding predicted estimate 603. In some embodiments, the machine learning model 13 may be trained to output one or more excluded treatment plans that should not be performed by the new patient.

Figure 7:
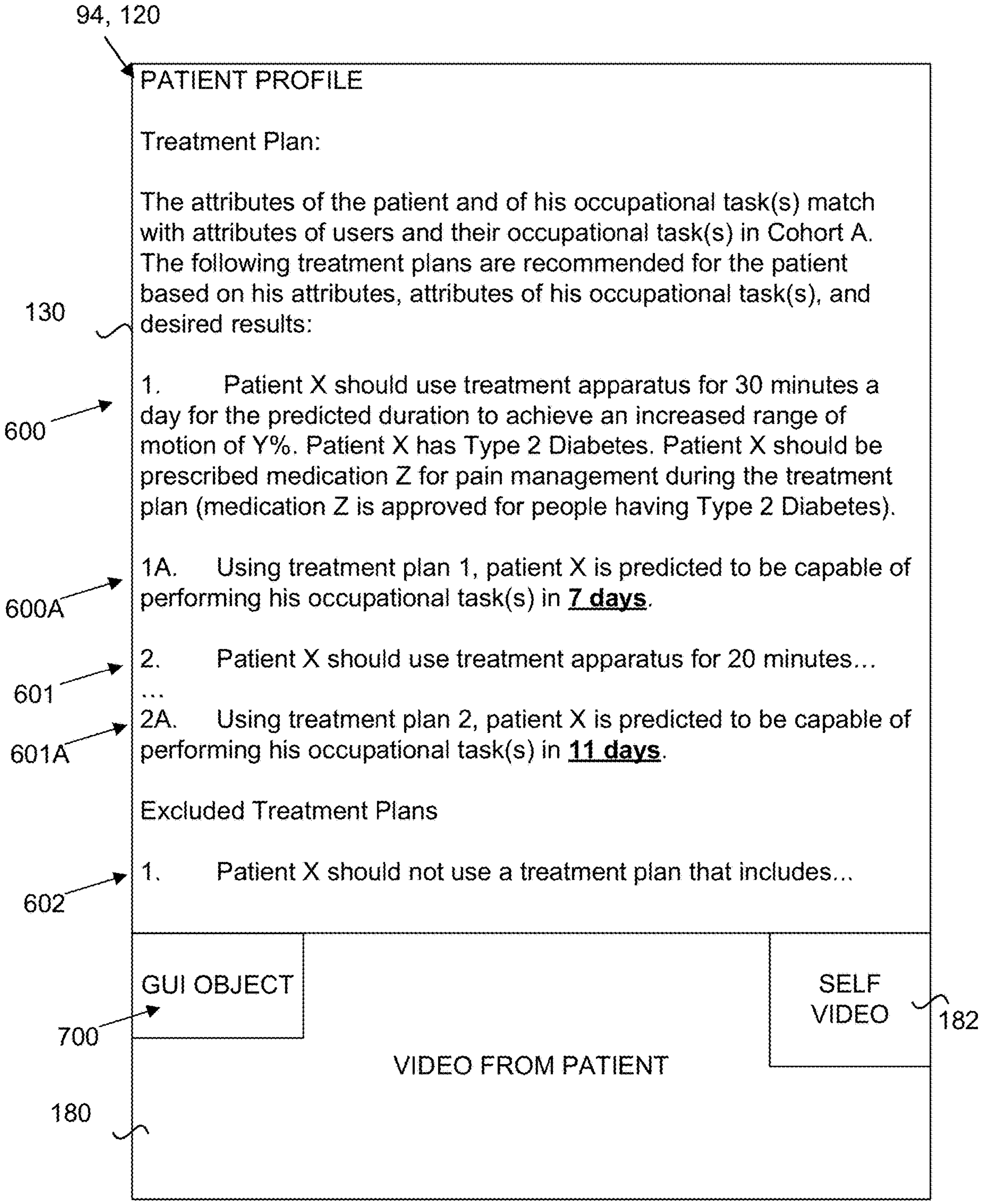
FIG. 7 shows an embodiment of an overview display of the healthcare professional interface presenting recommended treatment plans and excluded treatment plans in real-time during a telemedicine session according to the present disclosure.

FIG. 7 shows an embodiment of an overview display 120 of the healthcare professional interface 94 presenting recommended treatment plans and any excluded treatment plans in real-time during a telemedicine session, as well as predictions of estimates of when a patient, upon following a respective treatment plan, would be capable of performing his occupational tasks, according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

The healthcare professional using the healthcare professional interface 94 (e.g., computing device) during the telemedicine session may be presented in the self-video 182 in a portion of the overview display 120 (e.g., user interface presented on a display screen 24 of the healthcare professional interface 94) that also presents a video from the patient in the video feed display 180. Further, the video feed display 180 may also include a graphical user interface (GUI) object 700 (e.g., a button) that enables the healthcare professional to share, in real-time or near real-time during the telemedicine session, the recommended treatment plans and/or the predicted estimates and/or the excluded treatment plans with the patient on the patient interface 50. The healthcare professional may select the GUI object 700 to share the recommended treatment plans and/or the excluded treatment plans. The healthcare professional may select the GUI object 700 to share the predicted estimates for the recommended treatment plans. As depicted, another portion of the overview display 120 includes the patient profile display 130.

The patient profile display 130 is presenting two example recommended treatment plans 600, 601 (in part) each with example predicted estimates 600A, 601A of when the patient performing a respective recommended treatment plan 600, 601 would be capable of performing his occupational tasks. Also, the patient profile display 130 is presenting one example excluded treatment plan 602 (in part). As described herein, the treatment plans may be recommended in view of attributes of the patient being treated and in view of at least one attribute of an occupational task associated with the patient. The occupational task may be one of multiple occupational tasks for an occupation of the patient. To generate the recommended treatment plans 600, 601 the patient should follow in order for the patient to achieve a desired result, a pattern between the attributes of the patient being treated, the attributes of the occupational tasks associated with the patient, and a cohort of other people and their occupational tasks who have used the treatment apparatus 70 to perform a treatment plan may be matched by one or more machine learning models 13 of the artificial intelligence engine 11. Each of the recommended treatment plans may be generated based on different desired results. A desired result may be to first achieve a patient's capability of performing one particular occupational task of a set of occupational tasks. For example, a desired result may be for the patient to first achieve a flexibility requirement, and for the patient to later achieve a strength requirement. A different desired result may be to improve a patient's capabilities of performing some or all occupational tasks at about the same rate. For example, a desired result may be for the patient to achieve both a flexibility requirement and a strength requirement at about the same time.

For example, as depicted, the patient profile display 130 presents "The attributes of the patient and of his occupational task(s) match with attributes of users and their occupational task(s) in Cohort A. The following treatment plans are recommended for the patient based on his attributes and attributes of his occupational task(s)." Then, the patient profile display 130 presents recommended treatment plans from cohort A, and each treatment plan provides different results.

As depicted, treatment plan 600 indicates "Patient X should use treatment apparatus for 30 minutes a day for the predicted duration to achieve an increased range of motion of Y %; Patient X has Type 2 Diabetes. Patient X should be prescribed medication Z for pain management during the treatment plan (medication Z is approved for people having Type 2 Diabetes)." Accordingly, treatment plan 600 is for achieving an increasing the range of motion of Y %. As may be appreciated, treatment plan 600 also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome. This specific example and all such examples elsewhere herein are not intended to limit in any way the generated treatment plan from recommending multiple medications, or from handling the acknowledgement, view, diagnosis and/or treatment of comorbid conditions or diseases.

As depicted, a predicted estimate 600A corresponding to treatment plan 600 indicates a time at which the patient performing treatment plan 600 would be capable of performing the occupational task(s) associated with the patient: "Using treatment plan 1, patient X is predicted to be capable of performing his occupational task(s) in 7 days."

Recommended treatment plan 601 may specify, based on a different desired result of the treatment plan, a different treatment plan including a different treatment protocol for a treatment apparatus, a different medication regimen, etc. Furthermore, predicted estimate 601A corresponding to treatment plan 601 may indicate a respective time at which the patient performing treatment plan 601 would be capable of performing the occupational task(s) associated with the patient.

It will be appreciated that an estimate of when a patient performing a respective treatment plan would be capable of performing a particular occupational task or particular occupational tasks may be depicted in the form of time units such as days, weeks and/or months, half-days, half-weeks, half-months, or combinations thereof. An estimate may alternatively be depicted in the form of a particular date, such as "Jul. 31, 2022", calculated on the basis of a starting date and a particular time unit predicted via the artificial intelligence engine. Alternative forms of depiction of a predicted estimate may be available. Furthermore, a user may be provided with the option to toggle between different alternative forms of depiction of a predicted estimate, such as via selection through GUI OBJECT 700.

As depicted, the patient profile display 130 may also present the excluded treatment plans 602. These types of treatment plans are shown to the healthcare professional using the healthcare professional interface 94 to alert the healthcare professional not to recommend certain portions of a treatment plan to the patient. For example, an excluded treatment plan 602 could specify the following: "Patient X should not use treatment apparatus for longer than 30 minutes a day due to a heart condition; Patient X has Type 2 Diabetes; and Patient X should not be prescribed medication M for pain management during the treatment plan (in this scenario, medication M can cause complications for people having Type 2 Diabetes). Specifically, the excluded treatment plan 602 points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

The healthcare professional may select the treatment plan for the patient on the overview display 120. For example, the healthcare professional may use an input peripheral (e.g., mouse, touchscreen, microphone, keyboard, etc.) to select from the treatment plans 600, 601 for the patient. In some embodiments, during the telemedicine session, the healthcare professional may discuss the pros and cons of the recommended treatment plans 600, 601 with the patient. In some embodiments, during the telemedicine session, the healthcare professional may discuss the predicted estimates 600A, 601A with the patient.

In any event, the healthcare professional may select the treatment plan for the patient to follow to achieve the desired result. The selected treatment plan may be transmitted to the patient interface 50 for presentation. The patient may view the selected treatment plan on the patient interface 50. The patient may view the predicted estimate corresponding to the selected treatment plan on the patient interface 50. In some embodiments, the healthcare professional and the patient may discuss during the telemedicine session the details (e.g., treatment protocol using treatment apparatus 70, diet regimen, medication regimen, etc.) in real-time or in near real-time. In some embodiments, the server 30 may control, based on the selected treatment plan and during the telemedicine session, the treatment apparatus 70 as the user uses the treatment apparatus 70.

It may be useful and encouraging to provide a patient with information about an incentive such as an awardable product, object, activity, accolade, title, discount, coupon or some combination of these, and to communicate that the patient could earn the incentive by adhering to the selected treatment plan. The patient may be provided with this information via patient interface 50. If the form of the incentive itself is such that it may be provided via the patient interface 50, the patient may be provided with the incentive once it has been confirmed that the patient has adhered to the treatment plan. For example, if the incentive is an awardable pack of movie tickets, the patient may be provided with electronic codes or links via the patient interface 50 to redeem the movie tickets.

All patients may be offered the same incentive. However, different patients or the same patients at different times may be offered different incentives. A particular incentive for a particular patient may be selected based on the predicted estimate of time. For example, a higher-value incentive may be offered to patients whose treatment plan requires more or prolonged effort, than to those patients whose treatment plan requires less or less prolonged effort. Offering of an incentive may be intended to ensure the patient remains diligent about the treatment plan. It may be determined that there is no utility in offering a particular patient an incentive.

A particular incentive offered to a particular patient may be selected from a set of alternative incentives based on the attributes of the patient, subject to laws and regulations governing inappropriate discrimination. A set of multiple selectable incentives may be offered to a particular patient, from which the patient can select their choice of one or a subset. For example, a particular patient being offered one of two alternative incentives such as movie tickets and opera tickets may be enabled to choose one or the other based on their own differential preferences for different kinds of entertainment. Alternatively, all incentives available for offering may be presented to the patient so that the patient is not being offered any one or subset of kinds of incentives, thereby to enable the patient to self-select their incentive.

An incentive or set of incentives offered for selection by a patient may be selected using the artificial intelligence engine based on the cohort in which the patient has been included. For example, it may be determined using the artificial intelligence engine that individuals in a first cohort tend to be successful in adhering to their treatment plans when offered one kind or instance of an incentive, whereas individuals in a second cohort tend to be successful in adhering to their treatment plans when offered a different kind or instance of an incentive. A patient that is determined to be in the first cohort may not be offered any of the kinds or instances of incentives that would be offered to a patient who was determined to be in the second cohort. Alternatively, a patient that is determined to be in the first cohort may be offered the kinds or instances of incentives for their cohort first, while being provided with an option to receive offers of kinds or instances of incentives for another cohort in the event the patient was not interested in the kinds or instances of incentives that were first offered. As such, selections using the artificial intelligence engine of incentives or sets of incentives or kinds of incentives for offering to a patient may be done not to exclude certain incentives or sets of incentives or kinds of incentives from being offered to a patient, but to establish an order or format in which they could be presented to the patient for browsing and selection.

The patient interface 50 may display information about the incentive after it has been selected by a patient, for example during performance of the treatment plan. The patient interface 50, during treatment, may display a message stating "Congratulations! You have gotten through 75% of the predicted time for your treatment and all indications are that you have adhered nicely to your treatment plan. You should therefore soon be ready to return to work, and you will be able to celebrate your return after with the movie tickets! We're excited for you!"

Figure 8:
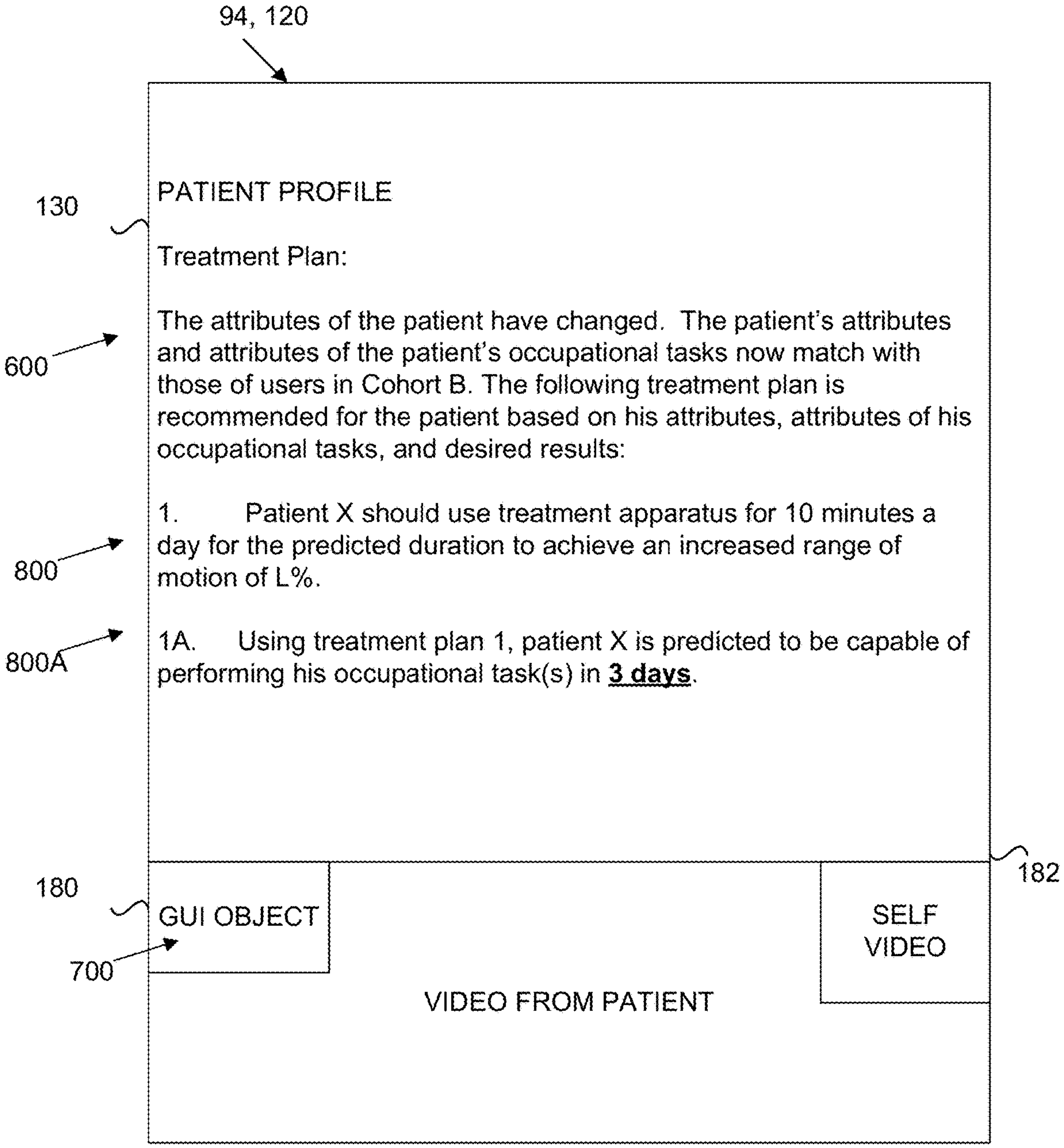
FIG. 8 shows an embodiment of the overview display of the healthcare professional interface presenting, in real-time during a telemedicine session, recommended treatment plans that have changed as a result of patient data changing according to the present disclosure.

FIG. 8 shows an embodiment of the overview display 120 of the healthcare professional interface 94 presenting, in real-time during a telemedicine session, recommended treatment plans that have changed as a result of patient data changing according to the present disclosure. As may be appreciated, the treatment apparatus 70 and/or any computing device (e.g., patient interface 50) may transmit data while the patient uses the treatment apparatus 70 to perform a treatment plan. The data may include updated attributes of the patient. For example, the updated attributes may include new performance information and/or measurement information. The performance information may include a speed of a portion of the treatment apparatus 70, a range of motion achieved by the patient, a force exerted on a portion of the treatment apparatus 70, a heartrate of the patient, a blood pressure of the patient, a respiratory rate of the patient, and so forth.

In one embodiment, the data received at the server 30 may be input into the trained machine learning model 13, which may determine that the attributes indicate the patient is on track for the current treatment plan. Determining the patient is on track for the current treatment plan may cause the trained machine learning model 13 to adjust a parameter of the treatment apparatus 70. The adjustment may be based on a next step of the treatment plan to further improve the performance of the patient.

In one embodiment, the data received at the server 30 may be input into the trained machine learning model 13, which may determine that the attributes indicate the patient is not on track (e.g., behind schedule, not able to maintain a speed, not able to achieve a certain range of motion, is in too much pain, etc.) for the current treatment plan or is ahead of schedule (e.g., exceeding a certain speed, exercising longer than specified with no pain, exerting more than a specified force, etc.) for the current treatment plan. The trained machine learning model 13 may determine that the attributes of the patient no longer match with the attributes of the patients in the cohort to which the patient is assigned. Accordingly, the trained machine learning model 13 may reassign the patient to another cohort that includes qualifying the patient's attributes. As such, the trained machine learning model 13 may select a new treatment plan, and may predict a second estimate of when the patient performing the new treatment plan would be capable of performing the occupational task(s) associated with the patient. Control of the treatment apparatus 70 would thereafter be based on the new treatment plan.

In some embodiments, prior to controlling the treatment apparatus 70, the server 30 may provide the new treatment plan 800, along with a new estimate 800A, to the healthcare professional interface 94 for presentation in the patient profile 130. As depicted, the patient profile 130 indicates "The attributes of the patient have changed. The patient's attributes and attributes of the patient's occupational tasks now match with those of users in Cohort B. The following treatment plan is recommended for the patient based on his attributes, attributes of his occupational tasks, and desired results." Then, the patient profile 130 presents the new treatment plan 800 ("Patient X should use treatment apparatus for 10 minutes a day for the predicted duration to achieve an increased range of motion of L %") and the new estimate 800A ("Using treatment plan 1, patient X is predicted to be capable of performing his occupational task(s) in 3 days."). The healthcare professional (healthcare professional) may select the new treatment plan 800, and the server 30 may receive the selection. The server 30 may control the treatment apparatus 70 based on the new treatment plan 800. In some embodiments, the new treatment plan 800 may be transmitted to the patient interface 50 such that the patient may view the details of the new treatment plan 800.

Figure 9:
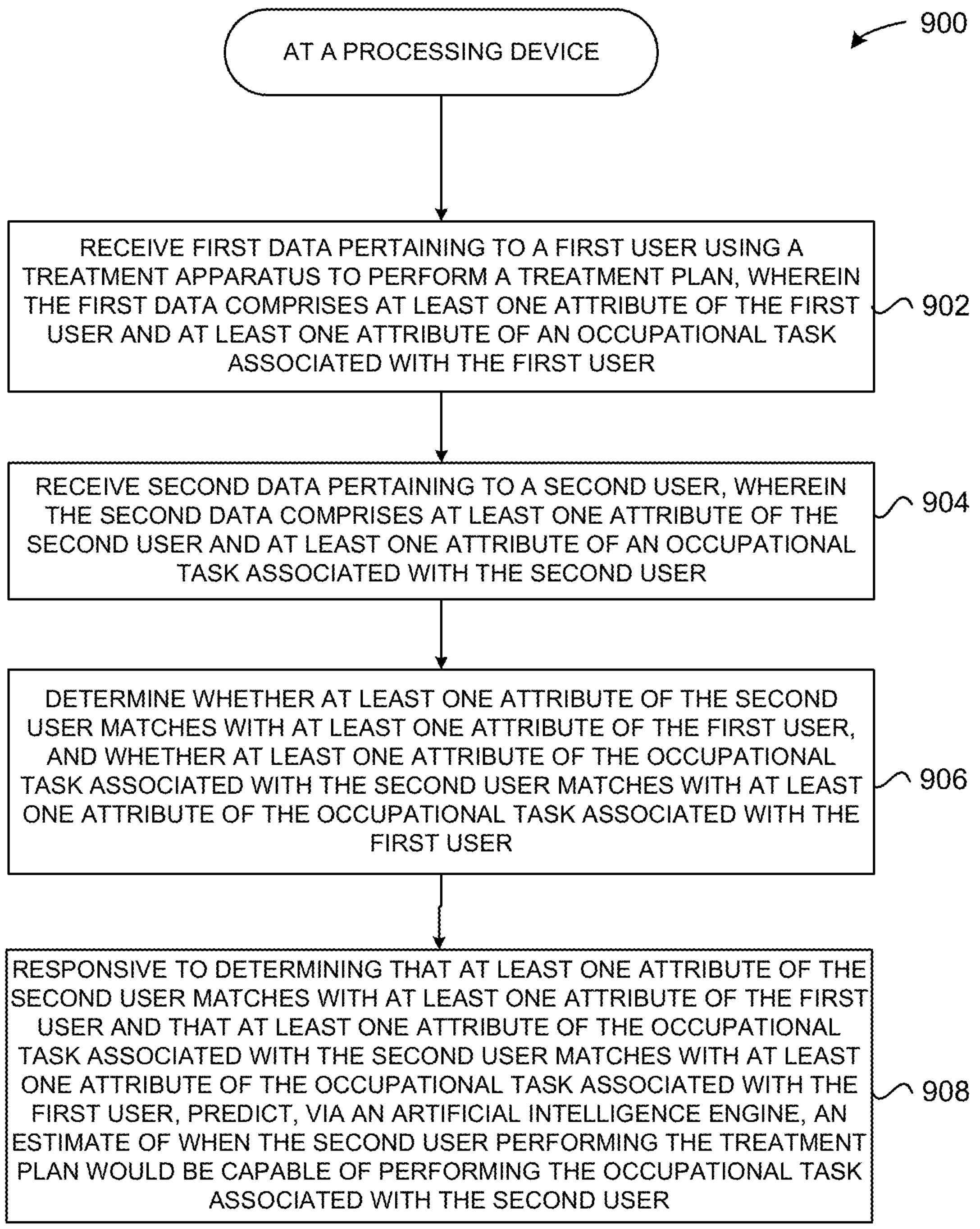
FIG. 9 shows an example embodiment of a method for selecting, based on assigning a patient to a cohort, a treatment plan for the patient and controlling, based on the treatment plan, a treatment apparatus according to the present disclosure.

FIG. 9 shows an example embodiment of a method 900 for predicting an estimate of when patient would be capable of performing an occupational task. The method 900 is performed by processing logic that may include hardware (circuitry, dedicated logic, etc.), software (such as is run on a general-purpose computer system or a dedicated machine), or a combination of both. The method 900 and/or each of its individual functions, routines, subroutines, or operations may be performed by one or more processors of a computing device (e.g., any component of FIG. 1, such as server 30 executing the artificial intelligence engine 11). In certain implementations, the method 900 may be performed by a single processing thread. Alternatively, the method 900 may be performed by two or more processing threads, each thread implementing one or more individual functions, routines, subroutines, object oriented method, or operations of the methods.

For simplicity of explanation, the method 900 is depicted and described as a series of operations. However, operations in accordance with this disclosure can occur in various orders and/or concurrently, and/or with other operations not presented and described herein. For example, the operations depicted in the method 900 may occur in combination with any other operation of any other method disclosed herein. Furthermore, not all illustrated operations may be required to implement the method 900 in accordance with the disclosed subject matter. In addition, those skilled in the art will understand and appreciate that the method 900 could alternatively be represented as a series of interrelated states via a state diagram or events.

At 902, the processing device may receive first data pertaining to a first user using a treatment apparatus 70 to perform a treatment plan. The first data may include at least one attribute of the first user and at least one attribute of an occupational task associated with the first user.

At 904, the processing device may receive second data pertaining to a second user. The second data may include at least one attribute of the second user and at least one attribute of an occupational task associated with the second user.

The attributes of the first user and the second user may include personal information, performance information, measurement information, or some combination thereof. In some embodiments, the personal information may include an age, a weight, a gender, a height, a body mass index, a medical condition, a familial medication history, an injury, or a medical procedure. In some embodiments, the performance information may include an elapsed time of using the treatment apparatus, an amount of force exerted on a portion of the treatment apparatus, a range of motion achieved on the treatment apparatus, a movement speed of a portion of the treatment apparatus, an indication of a set of pain levels using the treatment apparatus, or some combination thereof. In some embodiments, the measurement information may include a vital sign, a respiration rate, a heartrate, a temperature, or some combination thereof.

The attributes of an occupational task of the first user and the second user may include a stamina requirement, a strength requirement, a flexibility requirement, a pliability requirement, a range of motion requirement, a sustained attention requirement, a speech requirement, a height requirement, a weight requirement, a limb use requirement, or some combination thereof.

At 906, the processing device may determine whether at least one attribute of the second user matches with at least one attribute of the first user, and whether at least one attribute of the occupational task associated with the second user matches with at least one attribute of the occupational task associated with the first user.

At 908, responsive to determining that at least one attribute of the second user matches with at least one attribute of the first user and that at least one attribute of the occupational task associated with the second user matches with at least one attribute of the occupational task associated with the first user, the processing device may predict, via an artificial intelligence engine, an estimate of when the second user performing the treatment plan would be capable of performing the occupational task associated with the second user.

The predicting may include predicting an estimate of when a readiness score of the second user performing the treatment plan would satisfy a readiness score threshold for the occupational task associated with the second user. A readiness score for the second user may be based on at least one capability score of the second user in a capability required for the occupational task. A capability score may be a stamina score, a strength score, a flexibility score, a pliability score, a range of motion score, a sustained attention score, a speech score, a height score, a weight score, a limb use score, or some combination thereof. Similarly, a readiness score threshold may be based on at least one capability score threshold. A capability score threshold may be a stamina score threshold, a strength score threshold, a flexibility score threshold, a pliability score threshold, a range of motion score threshold, a sustained attention score threshold, a speech score threshold, a height score threshold, a weight score threshold, a limb use score threshold, or some combination thereof. It will be appreciated that, while a number of capability scores for a person may be available, a particular occupational task may not require all of the capabilities that a person may possess such that only a subset of the capability scores of a person may be required to determine whether the person's readiness score satisfies a readiness score threshold for the occupational task.

A readiness score threshold may include multiple components, and a readiness score may include multiple corresponding components. Determining whether the readiness score of a person satisfies the readiness score threshold of the occupational task may include determining whether each capability score threshold of which the readiness score threshold is comprised is satisfied by the person's respective capability score. For example, a readiness score threshold for a particular occupational task of lifting boxes off a truck in a warehouse may be composed of multiple individual capability score thresholds including a strength score threshold, a stamina score threshold, and a flexibility score threshold. In this example, the person's readiness score may be composed of multiple corresponding individual capability scores including a strength score, a stamina score, and a flexibility score. Therefore, in order for the person's readiness score to satisfy the readiness score threshold for this particular occupational task, each of the capability scores must satisfy the corresponding capability score thresholds. In this occupational task example, therefore, the person's strength score must satisfy the strength score threshold, the person's stamina score must satisfy the stamina score threshold, and the person's flexibility score must satisfy the flexibility score threshold. If the person's stamina score satisfies the stamina score threshold, the person's strength score satisfies the strength score threshold, and the person's flexibility score satisfies the flexibility score threshold, then the readiness score of the person is considered to satisfy the readiness score threshold of the occupational task, and the person is determined to be capable of performing the occupational task. In this example, if any of the capability scores does not satisfy its respective capability score threshold, the readiness score does not satisfy the respective readiness score threshold.

Table 1 sets out an example set of capability score thresholds for a given occupational task.

TABLE 1

| | Capability Score Threshold |
|---|---|
| Strength | 5 |
| Stamina | 8 |
| Flexibility | 6 |

In this example, a person's scores in strength, stamina and flexibility are required to determine whether the person is capable of performing the occupational task. A person's other capability scores may not be used to determine whether the person is capable of performing the occupational task. In this example, the strength score threshold (out of, for example, 10) is 5, the stamina score threshold is 8, and the flexibility score threshold is 6. The readiness score threshold may be expressed as 5-8-6. If the readiness score of a person—also expressed in a similar manner—satisfies the readiness score threshold, then the person is determined to be capable of performing the occupational task. In this example, the readiness score of a person satisfies the readiness score threshold for the occupational task if each of the capability scores satisfy respective capability score thresholds. Table 2 sets out an example set of capability scores for a person at a Time A, such as a time at which the person is first assessed for capabilities.

TABLE 2

| | Capability Score |
|---|---|
| Strength | 4 |
| Stamina | 8 |
| Flexibility | 4 |

In Table 2, the person's strength score is 4, his stamina score is 8, and his flexibility score is 4, for a multiple-component readiness score that may be expressed as 4-8-4. In this example, since the strength score of 4 is less than, and thus does not satisfy, the strength score threshold of 5, this is a sufficient condition for the readiness score threshold to be determined not to have been satisfied, such that the person would accordingly be determined to not be capable of performing the occupational task. It will be noted that another sufficient condition for the readiness score threshold to be determined not to have been satisfied in this example is that the flexibility score of 4 is less than, and thus does not satisfy, the flexibility score threshold of 6.

Table 3 sets out an example set of capability scores for the person at a Time B, such as a time after the person has been performing a treatment plan.

TABLE 3

| | Capability Score |
|---|---|
| Strength | 5 |
| Stamina | 9 |
| Flexibility | 6 |

In Table 3, the person's strength score is 5, his stamina score is 9, and his flexibility score is 6, for a readiness score that may be expressed as 5-9-6. In this example, since all of the capability scores pertaining to the occupational task are greater than or equal to respective capability score thresholds for the occupational task, the readiness score is considered to have satisfied the readiness score threshold and the person is determined to be capable of performing the occupational task.

It will be appreciated that a readiness score threshold may include only a single component corresponding to a single capability score threshold, and a readiness score may include only a single component corresponding to a single capability score. The single component of a readiness score threshold may be, simply, a single capability score threshold required by a particular occupational task, and the single component of a readiness score of a person with respect to the occupational task may be simply a single corresponding capability score of the person. For example, a particular occupational task may require only one capability such as flexibility, and a certain flexibility score to meet a certain flexibility score threshold, such that the readiness score threshold could be equivalent to, or derived directly from, a flexibility score threshold for the occupational task, and a readiness score for a person corresponding to the occupational task could be equivalent to, or derived directly from, a flexibility score of the person.

Alternatively, a readiness score threshold may include a single component that is determined as a weighted average of multiple capability score thresholds, and a readiness score may include a single component that is determined as a weighted average multiple capability scores of a person. For example, a readiness score threshold for the particular occupational task of lifting boxes off a truck in a warehouse may be composed of a weighted average of individual capability score thresholds including a strength score threshold, a stamina score threshold, and a flexibility score threshold. It may be determined by an employer, a health and safety regulatory body, or some other entity responsible for setting standards for occupational tasks that, for this particular occupational task, while stamina, strength and flexibility are required, stamina is more important than strength and flexibility. A readiness score threshold therefore may be determined as a weighted average that lends to a stamina score threshold a higher weighting in the weighted average calculation than to each of the strength score threshold and flexibility score threshold. For example, a stamina score threshold may be lent a 50% weighting, while each of the strength score threshold and flexibility score thresholds may be lent a 25% weighting, during calculation of the averages of these for determining the readiness score threshold. Similarly, in this example, the readiness score of a person may be determined as a weighted average that lends to a stamina score the higher weight than to each of the strength score and flexibility score. For example, to correspond to the weighted average calculation of the readiness score threshold in this example, for a weighted average calculation of the person's readiness score, his stamina score is lent a 50% weighting, while each of his strength score and flexibility score may be lent a 25% weighting. Then, once the resultant readiness score of the person satisfies the resultant readiness score threshold of the occupational task, the person is determined to be capable of performing the occupational task. It will be noted that, due to the weighted averaging, a readiness score may satisfy a readiness score threshold even if a particular capability score does not satisfy its corresponding particular capability score threshold for the occupational task. For example, a person's strength score may not quite satisfy the corresponding strength score for the occupational task, but due to the person's stamina score and flexibility score and the respective differential weightings applied to each of the strength score, stamina score and flexibility score, the resultant readiness score being calculated as a weighted average may nevertheless satisfy the corresponding readiness score threshold such that the person is determined to be capable of performing the occupational task.

In such an example, the person may have a flexibility score that is lower than the flexibility score threshold of the occupational task, but due to differential weightings and that person's stamina score exceeding the stamina score threshold of the occupational task, the person would be considered ready overall to perform the occupational task.

Table 4 sets out an example set of capability score thresholds for a given occupational task.

TABLE 4

| | Capability Score Threshold | Weight |
|---|---|---|
| Strength | 5 | 0.25 |
| Stamina | 8 | 0.5 |
| Flexibility | 6 | 0.25 |

In this example, a person's capability scores for strength, stamina and flexibility are required in order to determine whether the person is capable of performing the occupational task. A person's other capability scores (such as a height score) may not be needed to determine whether the person is capable of performing the occupational task. In this example, in the readiness score threshold calculation, the strength score threshold of 5 is given a weight of 0.25, the stamina score threshold of 8 is given a weight of 0.5, and the flexibility score threshold of 6 is given a weight of 0.25, for a single component readiness score threshold of 6.75. Similarly, in a readiness score calculation for a person, the person's strength score is given a weight of 0.25, his stamina score is given a weight of 0.5, and his flexibility score is given a weight of 0.25. If the readiness score of a person—calculated as a weighted average of the person's capability scores for each of strength, stamina, and flexibility—satisfy the readiness score threshold, then the person may be deemed to be capable of performing the occupational task. Table 5 sets out an example set of capability scores for a person at a Time A, such as a time at which the person is first assessed for capabilities.

TABLE 5

| | Capability Score | Weight |
|---|---|---|
| Strength | 4 | 0.25 |
| Stamina | 8 | 0.5 |
| Flexibility | 4 | 0.25 |

In Table 5, the person's strength score is 4, his stamina score is 8, and his flexibility score is 4, for a single component readiness score—calculated as a weighted average according to the weights shown in Table 5—of 6.0. In this example, since the readiness score of 6.0 is not equal to or greater than the readiness score threshold of 6.75, the readiness score does not satisfy the readiness score threshold and the person may be deemed to not be yet capable of performing the occupational task.

Table 6 sets out an example set of capability scores for the person at a Time B, such as a time after the person has been performing a treatment plan.

TABLE 6

| | Capability Score | Weight |
|---|---|---|
| Strength | 5 | 0.25 |
| Stamina | 9 | 0.5 |
| Flexibility | 5 | 0.25 |

In Table 6, the person's strength score is 5, his stamina score is 9, and his flexibility score is 5, for a single component readiness score—calculated as a weighted average according to the weights shown in Table 6—of 7.0. In this example, since the single component readiness score of 7.0 is greater than the readiness score threshold of 6.75, the readiness score satisfies the readiness score threshold and the person is determined to be capable of performing the occupational task.

The treatment plan may include a treatment protocol that specifies using the treatment apparatus 70 to perform certain exercises for certain lengths of time and a periodicity for performing the exercises. The treatment protocol may also specify parameters of the treatment apparatus 70 for each of the exercises. For example, a two-week treatment protocol for a person having certain attributes (e.g., respiration, weight, age, injury, current range of motion, heartrate, etc.) may specify the exercises for a first week and a second week. The exercise for the first week may include pedaling a bicycle for a 10-minute time period where the pedals gradually increase or decrease a range of motion every 1 minute throughout the 10-minute time period. The exercise for the second week may include pedaling a bicycle for a 5-minute time period where the pedals aggressively increase or decrease a range of motion every 1 minute throughout the 10-minute time period.

In some embodiments, the processing device may control, based on the treatment plan, the treatment apparatus 70 while the second user uses the treatment apparatus. In some embodiments, the controlling may be performed by the server 30 distal from the treatment apparatus 70 (e.g., during a telemedicine session). Controlling the treatment apparatus 70 distally may include the server 30 transmitting, based on the treatment plan, a control instruction to change a parameter of the treatment apparatus 70 at a particular time to increase a likelihood of a positive effect of continuing to use the treatment apparatus or to decrease a likelihood of a negative effect of continuing to use the treatment apparatus. For example, the treatment plan may include information (based on historical information of people having certain attributes and performing exercises in the treatment plan) indicating there may be diminishing returns after a certain amount of time of performing a certain exercise. Accordingly, the server 30, executing one or more machine learning models 13, may transmit a control signal to the treatment apparatus 70 to cause the treatment apparatus 70 to change a parameter (e.g., slow down, stop, etc.).

In some embodiments, the treatment apparatus used by the first user may be the treatment apparatus used by the second user, or the treatment apparatus used by the first user may not be the treatment apparatus used by the second user. For example, if the first user and the second user are members of a family, then they may both use one treatment apparatus at different times. If the first user and the second user live in different residences, then the first user and the second user may use different treatment apparatuses, either simultaneously or at different times.

The term "same" used in connection with two or more treatment apparatuses may refer to the two or more treatment apparatuses being separate physical objects but having the same specifications.

In some embodiments, the processing device may continue to receive data while the second user uses the treatment apparatus 70 to perform the treatment plan. The data received may include attributes of the second user while the second user uses the treatment apparatus 70 to perform the treatment plan. The attributes may include information pertaining to measurements (e.g., respiration, heartrate, temperature, perspiration) and performance (e.g., range of motion, force exerted on a portion of the treatment apparatus 70, speed of actuating a portion of the treatment apparatus 70, etc.). The data may indicate that the second user is improving (e.g., maintaining a desired speed of the treatment plan, range of motion, and/or force) as expected in view of the treatment plan for a person having similar data. Accordingly, the processing device may adjust, via a trained machine learning model 13, based on the data and the treatment plan, a parameter of the treatment apparatus 70. For example, the data may indicate the second user is pedaling a portion of the treatment apparatus 70 for 3 minutes at a certain speed. Thus, the machine learning model may adjust, based on the data and the treatment plan, an amount of resistance of the pedals to attempt to cause the second user to achieve a certain result (e.g., strengthen one or more muscles). The certain result may have been achieved by other users with similar data (e.g., attributes including performance, measurements, etc.) exhibited by the second user at a particular point in a treatment plan.

In some embodiments, the processing device may receive, from the treatment apparatus 70, data pertaining to second attributes of the second user while the second user uses the treatment apparatus 70 to perform the treatment plan. The second attributes may include information pertaining to measurements (e.g., respiration, heartrate, temperature, perspiration) and performance (e.g., range of motion, force exerted on a portion of the treatment apparatus 70, speed of actuating a portion of the treatment apparatus 70, etc.) of the second user as the second user uses the treatment apparatus 70 to perform the treatment plan. In some embodiments, the processing device may determine, based on the attributes, that the second user is improving faster than expected for the treatment plan or is not improving (e.g., unable to maintain a desired speed of the treatment plan, range of motion, and/or force) as expected for the treatment plan.

The processing device may determine that the second attributes of the second user match with attributes of a third user assigned to a second cohort. The second cohort may include data for people having different attributes than the cohort to which the second user was initially assigned. Responsive to determining the second attributes of the second user match with the attributes of the third user and that attributes of the occupational tasks of the second user match with attributes of the occupational tasks of the third user, the processing device may assign the second user to the second cohort and select, via the trained machine learning model, a second treatment plan for the second user. Accordingly, the treatment plan for a user using the treatment apparatus 70 may be dynamically adjusted, in real-time while the user is using the treatment apparatus 70, to best fit the attributes of the second user and enhance a likelihood the second user achieves a desired result experienced by other people in a particular cohort to which the second user is assigned. The second treatment plan may have been performed by the third user with similar attributes to the second user and occupational tasks similar to those of the second user, and as a result of performing the second treatment plan, the third user may have achieved a desired result. The processing device may control, based on the second treatment plan, the treatment apparatus 70 while the second user uses the treatment apparatus.

The processing device may determine that the second attributes of the second user match with attributes of a third user assigned to a second cohort. The second cohort may include data for people having different attributes than the cohort to which the second user was initially assigned. Responsive to determining the second attributes of the second user match with the attributes of the third user and that attributes of the occupational tasks of the second user match with attributes of the occupational tasks of the third user, the processing device may assign the second user to the second cohort and select, via the trained machine learning model, the same treatment plan for the second user but with a prediction of a second estimate of when the second user performing the treatment plan would be capable of performing the occupational tasks associated with the second user. The same treatment plan may have been performed by the third user with similar attributes to the second user and occupational tasks similar to those of the second user, and as a result of performing the same treatment plan, the third user may have achieved a desired result but in a different time frame that had been originally predicted for the second user thus warranting a second estimate prediction. Data regarding the prediction of the second estimate may be provided to a user such as a healthcare professional via the healthcare professional interface 94, 120. The processing device may continue to control, based on the treatment plan, the treatment apparatus 70 while the second user uses the treatment apparatus.

In some embodiments, responsive to determining the attributes of the second user do not match with the attributes of the first user and/or that attributes of the occupational tasks of the second user do not match with attributes of the occupational tasks of the first user, the processing device may determine whether at least the attributes of the second user match with attributes of a third user and attributes of the occupational tasks associated with the second user match with attributes of the occupational tasks associated with the third user, the third user having been assigned to a second cohort. Responsive to determining the attributes of the second user match with the attributes of the third user and that the attributes of the occupational tasks of the second user match with the attributes of the occupational tasks of the third user, the processing device may assign the second user to the second cohort and select, via the trained machine learning model, a second treatment plan for the second user. The processing device may also predict, via the trained machine learning model, a second estimate of when the patient performing the second treatment plan will be capable of performing the occupational tasks associated with the second user. The second treatment plan may have been performed by the third user with similar attributes to the second user and with attributes of occupational tasks similar to those of the third user, and as a result of performing the second treatment plan, the third user may have achieved a desired result and in a different or the same time frame that had been originally predicted for the second user thus warranting a second estimate prediction. Data regarding the selected second treatment plan and the prediction of the second estimate may be provided to a user such as a healthcare professional via the healthcare professional interface 94, 120, and the healthcare professional may select or decline the second treatment plan. In the event the healthcare professional selects the second treatment plan via the healthcare professional interface 94, 120, the processing device may control, based on the second treatment plan, the treatment apparatus 70 while the second user uses the treatment apparatus. Rather than automatically assigning the second user to the second cohort, assigning the second user to the second cohort may be done only in the event that the healthcare professional selects the second treatment plan, and is not done if the healthcare professional declines the second treatment plan.

Figure 10:
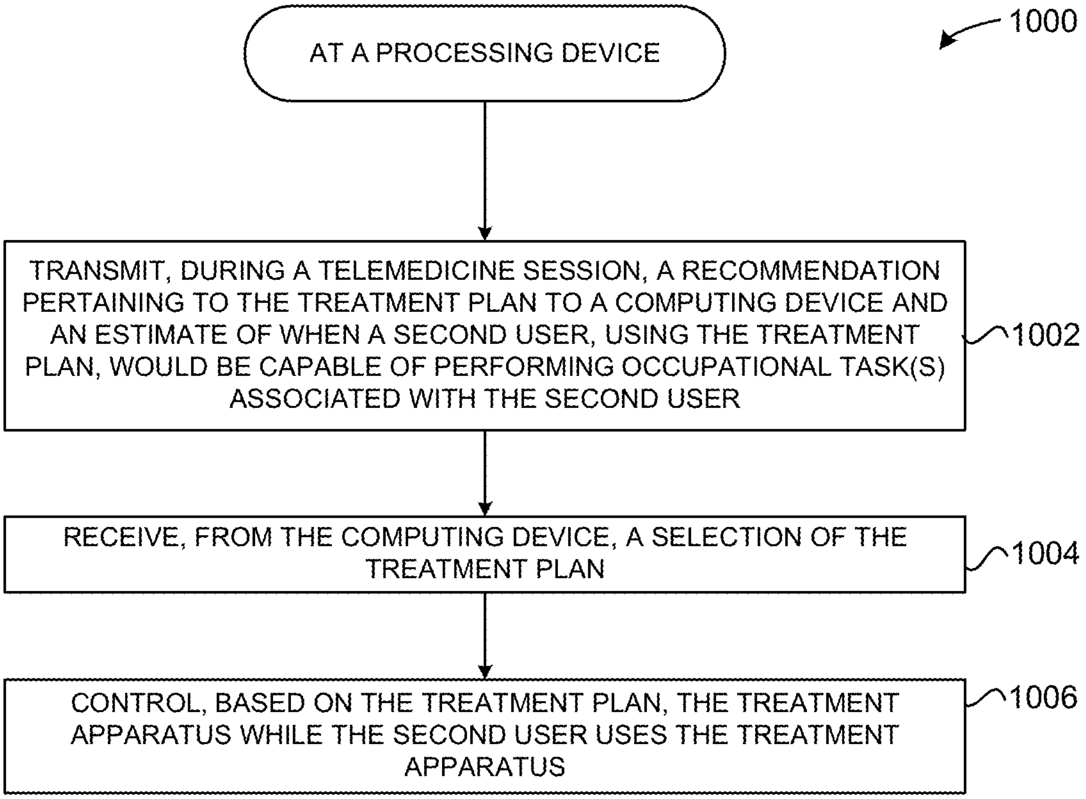
FIG. 10 shows an example embodiment of a method for presenting, during a telemedicine session, the recommended treatment plan to a healthcare professional according to the present disclosure.

FIG. 10 shows an example embodiment of a method 1000 for presenting, during a telemedicine session, the recommended treatment plan to a healthcare professional according to the present disclosure. Method 1000 includes operations performed by processors of a computing device (e.g., any component of FIG. 1, such as server 30 executing the artificial intelligence engine 11). In some embodiments, one or more operations of the method 1000 are implemented in computer instructions stored on a memory device and executed by a processing device. The method 1000 may be performed in the same or a similar manner as described above in regard to method 900. The operations of the method 1000 may be performed in some combination with any of the operations of any of the methods described herein.

In some embodiments, the method 1000 may occur after 908 in the method 900 depicted in FIG. 9 and prior to controlling the treatment apparatus 70. That is, the method 1000 may occur prior to the server 30 executing the one or more machine learning models 13 controlling the treatment apparatus 70.

Regarding the method 1000, at 1002, prior to controlling the treatment apparatus 70 while the second user uses the treatment apparatus 70, the processing device may provide, during a telemedicine or telehealth session, a recommendation pertaining to the treatment plan to a computing device (e.g., healthcare professional interface 94) of a healthcare professional, as well as an estimate of when the second user performing the treatment plan would be capable of performing occupational task(s) associated with the second user. The recommendation and estimate may be presented on a display screen of the computing device in real-time (e.g., less than 2 seconds) in a portion of the display screen while another portion of the display screen presents video of a user (e.g., patient).

At 1004, the processing device may receive, from the computing device of the healthcare professional, a selection of the treatment plan. The healthcare professional may use any suitable input peripheral (e.g., mouse, keyboard, microphone, touchpad, etc.) to select the recommended treatment plan. The computing device may transmit the selection to the processing device of the server 30, which receives the selection. There may any suitable number of treatment plans presented on the display screen. Each of the treatment plans recommended may provide different results and the healthcare professional may consult, during the telemedicine session, with the user to discuss which result the user desires. In some embodiments, the recommended treatment plans and predicted estimates may only be presented on the computing device of the healthcare professional and not on the computing device of the user (patient interface 50). In some embodiments, the healthcare professional may choose an option presented on the healthcare professional interface 94. The option may cause the treatment plans to be transmitted to the patient interface 50 for presentation. The option may cause the corresponding predicted estimates to be transmitted to the patient interface 50 for presentation. In this way, during the telemedicine session, the healthcare professional and the user may view the treatment plans and the predicted estimates at the same time in real-time or in near real-time, which may provide for an enhanced user experience for the user using the computing device. After the selection of the treatment plan is received at the server 30, at 1006, the processing device may control, based on the selected treatment plan, the treatment apparatus while the second user uses the treatment apparatus 70.

Data pertaining to the predicted estimate of when the user performing the selected treatment plan will be capable of performing the occupational task(s) may be made available, via another of the interfaces 20, 90, 92 or 94, to other healthcare professionals or to other personnel. Such other personnel may include administrators of insurance plans or workers' compensation administrators. Such personnel may use the data to plan for upcoming expenditures to be made in respect of the user. The data pertaining to the predicted estimate of time may include data pertaining to a prediction of an estimate of the cost of the user performing the treatment plan to become capable of performing the occupational task(s). The data pertaining to the prediction of an estimate of a cost may be based on a cost-per-day rate for the user, and the predicted estimate of time.

Figure 11:
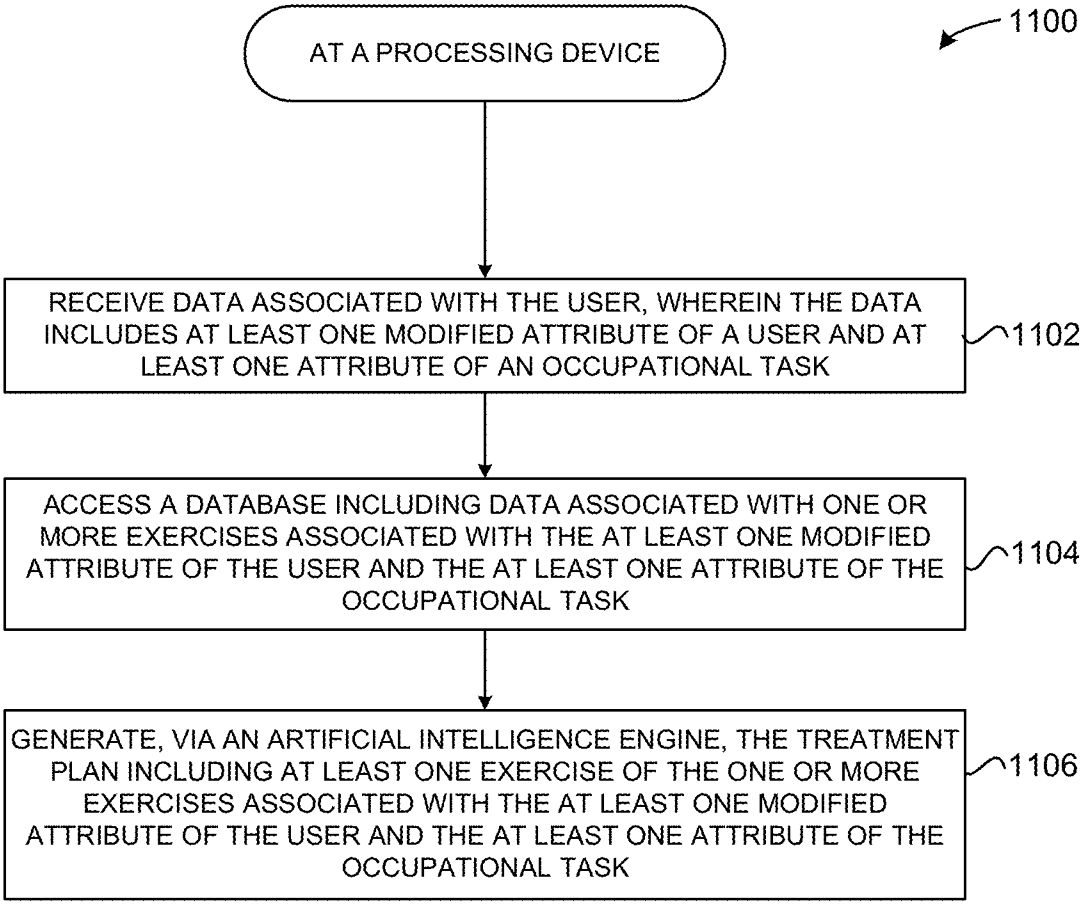
FIG. 11 shows an example embodiment of a method for generating a treatment plan including exercises associated with a modified attribute of a user and an attribute of an occupational task according to the present disclosure.

FIG. 11 shows an example embodiment of a method 1100 for generating a treatment plan, wherein the treatment plan includes exercises associated with a modified attribute of a user and an attribute of an occupational task according to the present disclosure. Method 1100 includes operations performed by processors of a computing device (e.g., any component of FIG. 1, such as server 30 executing the artificial intelligence engine 11). In some embodiments, one or more operations of the method 1100 are implemented in computer instructions stored on a memory device and executed by a processing device. The method 1100 may be performed in the same or a similar manner as described above in regard to method 900. The operations of the method 1100 may be performed in some combination with any of the operations of any of the methods described herein.

The computer-implemented method 1100 may generate a treatment plan to modify at least one attribute of a user. The at least one attribute of the user may be associated with at least one attribute of an occupational task. The at least one attribute of the occupational task may include, without limitation, requirements associated with stamina, strength, flexibility, range of motion, pliability, sustained attention, speech, height, weight, limb use, body mass index, blood glucose, intelligence quotient, or some combination thereof.

At 1102, the processing device may receive data associated with the user. The data may include at least one modified attribute of the user and the at least one attribute of the occupational task. In some embodiments, the at least one modified attribute of the user may include, without limitation, recovery information, personal information, performance information, measurement information, incentive information, cost information, user satisfaction level information, insurance information, employment information, or some combination thereof.

The recovery information may include, without limitation, a target rate of recovery, a target state of recovery, a target recovery outcome, a target recovery satisfaction level, or some combination thereof.

The personal information may include, without limitation an age, a weight, a gender, a race, an ethnicity, a marital status, an income, an education level, a height, a body mass index, a medical condition, a familial medical history, an injury, a medical procedure, a drug prescription, a nutritional supplement, and an illicit drug history, or some combination thereof.

The performance information may include, without limitation, an elapsed time for using the treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, a description of the treatment plan associated with the treatment apparatus, or some combination thereof.

The measurement information may include, without limitation, a vital sign, a respiration rate, a heartrate, a temperature, blood glucose, or some combination thereof.

The incentive information may include, without limitation, information about an awardable product, an object, an activity, an accolade, a title, a discount, a coupon, a unit or amount of money, an amount of cryptocurrency, or some combination thereof.

At 1104, the processing device may access a database including data associated with one or more exercises associated with the at least one modified attribute of the user and the at least one attribute of the occupational task. In some embodiments, the database may include a set of cohorts of data associated with exercises associated with modified attributes of users and attributes of occupational tasks. By at least matching the data associated with the one or more exercises with the data pertaining to the exercises, the processing device may select a cohort form the set of cohorts of data.

At 1106, the processing device may generate, via an artificial intelligence engine 11, the treatment plan, wherein the treatment plan includes at least one exercise of the one or more exercises associated with the at least one modified attribute of the user and the at least one attribute of the occupational task. The artificial intelligence engine 11 may generate the treatment plan, wherein the treatment plan includes the at least one exercise based on the data associated with the user and the data associated with the one or more exercises. In some embodiments, the treatment plan may include various operating parameters that are transmitted as control instructions to the treatment apparatus 70. The control instructions may cause the treatment apparatus 70 to use the operating parameters to adjust a portion of the treatment apparatus 70 in real-time or near real-time. Accordingly, the processing device may be configured to, based on the treatment plan and while the user uses the treatment apparatus 70, control the treatment apparatus 70.

In some embodiments, the processing device may estimate, via the artificial intelligence engine 11, when the user performing the treatment plan would be capable of performing the occupational task to a targeted performance level (e.g., 10%, 15%, 30%, 50%, 75%, 100%, etc.). The targeted performance level may be a percentage and/or an absolute value. The estimate may be a determined period of time or a date range (e.g., hours, days, weeks, months, years, etc.).

Figure 12:
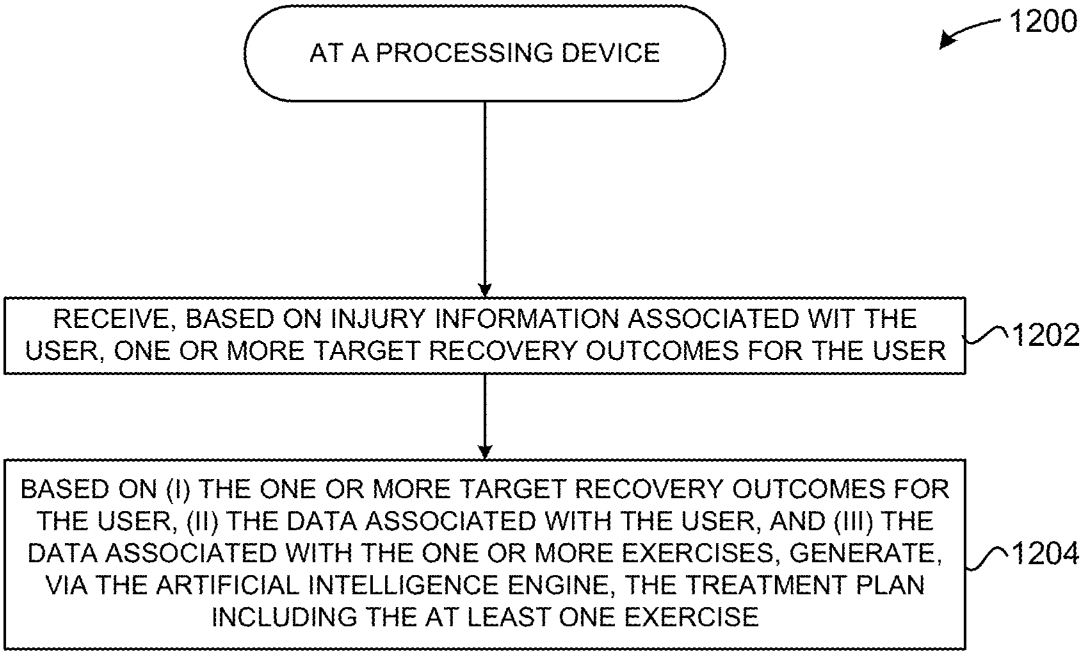
FIG. 12 shows an example embodiment of a method for using target recovery outcomes for the user to generate the treatment plan according to the present disclosure.

FIG. 12 shows an example embodiment of a method 1200 for using target recover outcomes for the user to generate the treatment plan according to the present disclosure. Method 1200 includes operations performed by processors of a computing device (e.g., any component of FIG. 1, such as server 30 executing the artificial intelligence engine 11). In some embodiments, one or more operations of the method 1200 may be implemented in computer instructions stored on a memory device and executed by a processing device. The method 1200 may be performed in the same or a similar manner as described above in regard to method 900. The operations of the method 1200 may be performed in some combination with any of the operations of any of the methods described herein.

At 1202, the processing device may receive, based on injury information associated with the user, one or more target recovery outcomes for the user. In some embodiments, the injury information may be received from an electronic medical record (EMR) system to which the artificial intelligence engine 11 is connected. For example, the interface of the EMR system may be exposed as an application programming interface (API) to which the artificial intelligence engine 11 connects, and/or the EMR system may host a website that the artificial intelligence engine 11 queries for the injury information. In other embodiments, the injury information may be received from an insurance provider system. For example, the interface of the insurance provider system may be exposed as an application programming interface (API) to which the artificial intelligence engine 11 connects, and/or the insurance provider system may host a website that the artificial intelligence engine 11 queries for the injury information.

In some embodiments, the one or more target recovery outcomes may be provided by an insurance provider associated with the user. The insurance provider may provide a desired recovery time to minimize an amount of money they will pay for workers' compensation. For example, the desired recovery time may include a period of time (e.g., days, weeks, months, years) in which the insurance provider desires the user to recover in order to minimize an amount of money the insurance provider has to pay the user as part of the user's benefits under an insurance plan.

The target recovery outcomes may include a recovery time (e.g., days, weeks, months, years), an improvement to a range of motion for the recovery, a state of recovery (e.g., fully recovered, partial recovery, etc.), a metric of recovery (e.g., 10%, 40%, 60%; good, bad; initial, middle, complete; 30, measurement 50, level 75, etc.), a physiological improvement, a user assessment of their pain level, a user assessment of their satisfaction, etc.).

At 1204, based on (i) the one or more recovery outcomes for the user, (ii) the data associated with the user, and (iii) the data associated with the one or more exercises, the processing device may generate, via the artificial intelligence engine 11, the treatment plan, wherein the treatment plan includes the at least one exercise. In some embodiments, the treatment plan may include various operating parameters that are transmitted as control instructions to the treatment apparatus 70. The control instructions may cause the treatment apparatus 70 to use the operating parameters to adjust a portion of the treatment apparatus 70 in real-time or near real-time.

Figure 13:
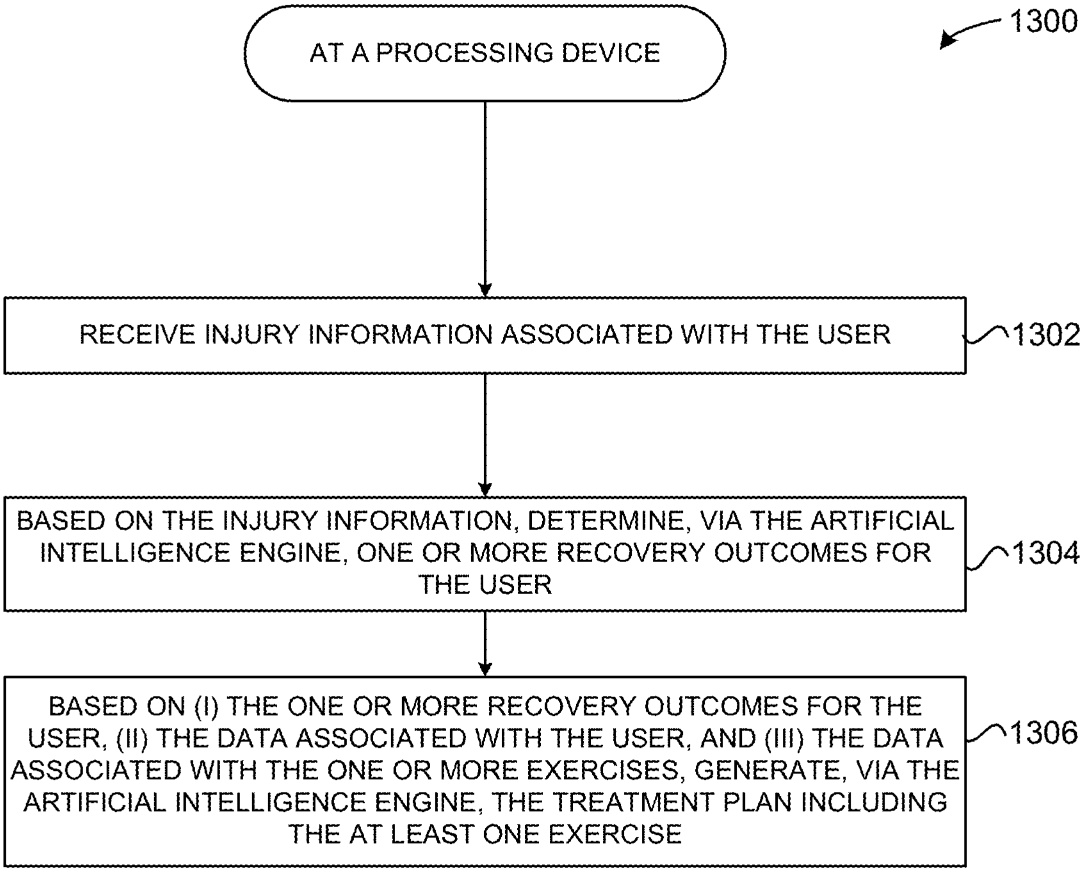
FIG. 13 shows an example embodiment of a method for using injury information associated with the user to generate the treatment plan according to the present disclosure.

FIG. 13 shows an example embodiment of a method 1300 for using injury information associated with the user to generate the treatment plan according to the present disclosure; Method 1300 includes operations performed by processors of a computing device (e.g., any component of FIG. 1, such as server 30 executing the artificial intelligence engine 11). In some embodiments, one or more operations of the method 1300 may be implemented in computer instructions stored on a memory device and executed by a processing device. The method 1300 may be performed in the same or a similar manner as described above in regard to method 900. The operations of the method 1300 may be performed in some combination with any of the operations of any of the methods described herein.

At 1302, the processing device may receive injury information associated with the user. In some embodiments, the injury information may include information about the injury, such as physical state of the user, medical state of the user (e.g., which medications the user is taking, whether user smokes/drinks alcohol, medical history of the user, familial medical history of the user, etc.), psychological state of the user, pain level of the user, neurological state of the user, and the like.

At 1304, based on the injury information, the processing device may determine, via the artificial intelligence engine 11, one or more recovery outcomes for the user. In some embodiments, the one or more recovery outcomes may include, without limitation, a target recovery time for the user, a target recovery time specified by an insurance provider, a target recovery state for the user, a target recovery cost for the user, a target recovery cost for the insurance provider, or some combination thereof.

At 1306, based on (i) the one or more recovery outcomes for the user, (ii) the data associated with the user, and (iii) the data associated with the one or more exercises, the processing device may generate, via the artificial intelligence engine 11, the treatment plan, wherein the treatment plan include the at least one exercise. In some embodiments, the treatment plan may include various operating parameters transmitted as control instructions to the treatment apparatus 70. The control instructions may cause the treatment apparatus 70 to use the operating parameters to adjust a portion of the treatment apparatus 70 in real-time or near real-time.

Figure 14:
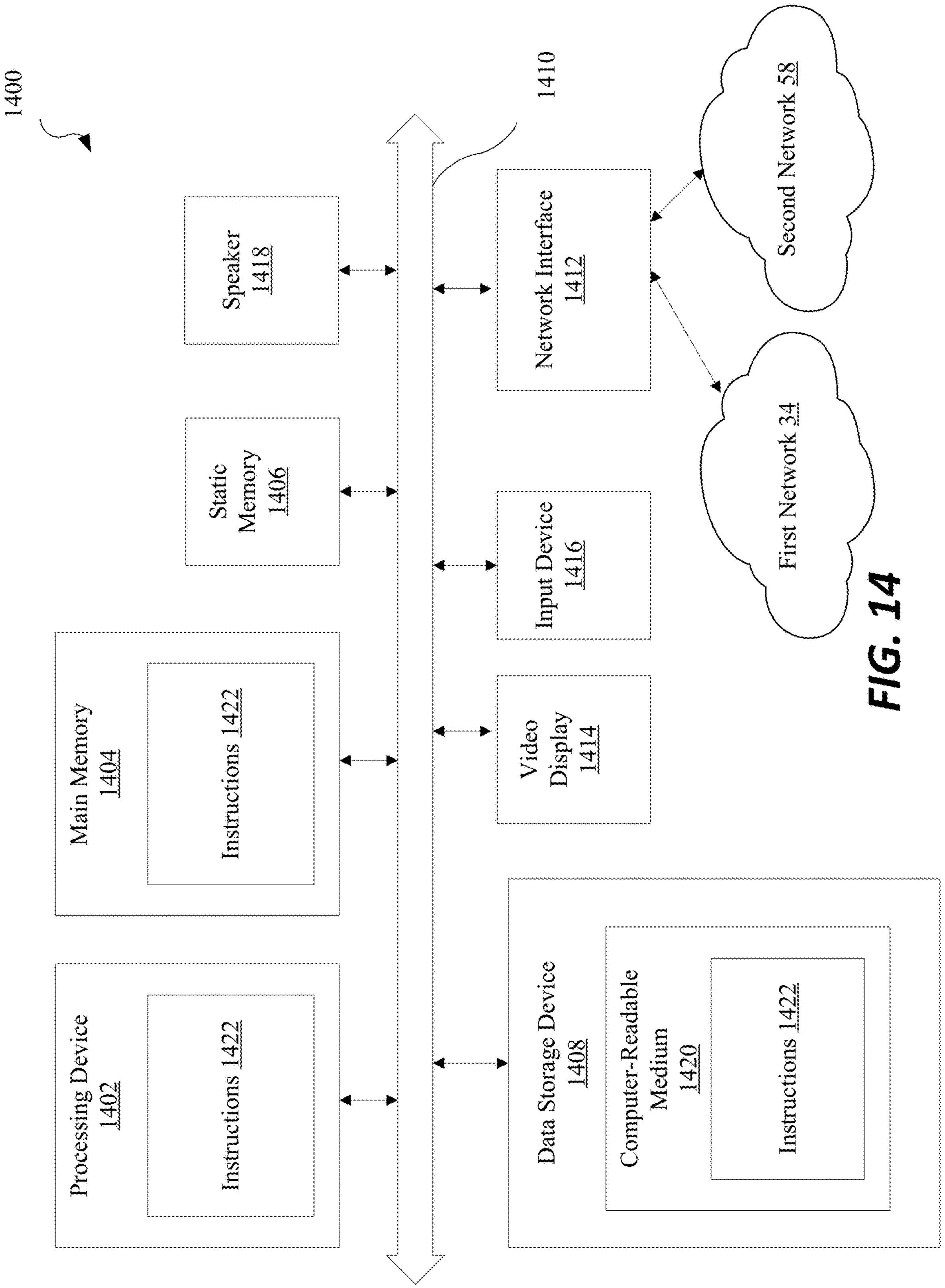
FIG. 14 shows an example computer system according to the present disclosure.

FIG. 14 shows an example computer system 1400 which can perform any one or more of the methods described herein, in accordance with one or more aspects of the present disclosure. In one example, computer system 1400 may include a computing device and correspond to the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1400 may be capable of executing instructions implementing the one or more machine learning models 13 of the artificial intelligence engine 14 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1400 includes a processing device 1402, a main memory 1404 (e.g., read-only memory (ROM), flash memory, solid state drives (SSDs), dynamic random access memory (DRAM) such as synchronous DRAM (SDRAM)), a static memory 1406 (e.g., flash memory, solid state drives (SSDs), static random access memory (SRAM)), and a data storage device 1408, which communicate with each other via a bus 1410.

Processing device 1402 represents one or more general-purpose processing devices such as a microprocessor, central processing unit, or the like. More particularly, the processing device 1402 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1400 may further include a network interface device 1412. The computer system 1400 also may include a video display 1414 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1416 (e.g., a keyboard and/or a mouse or a gaming-like control), and one or more speakers 1418 (e.g., a speaker). In one illustrative example, the video display 1414 and the input device(s) 1416 may be combined into a single component or device (e.g., an LCD touch screen).

The data storage device 1416 may include a computer-readable medium 1420 on which the instructions 1422 embodying any one or more of the methods, operations, or functions described herein is stored. The instructions 1422 may also reside, completely or at least partially, within the main memory 1404 and/or within the processing device 1402 during execution thereof by the computer system 1400. As such, the main memory 1404 and the processing device 1402 also constitute computer-readable media. The instructions 1422 may further be transmitted or received over a network via the network interface device 1412.

While the computer-readable storage medium 1420 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clauses

Clause 1. A computer-implemented system, comprising:

a treatment apparatus configured to be manipulated by a user while the user performs a treatment plan;

a patient interface associated with the user; and a server computing device configured to generate the treatment plan that includes at least one modified attribute of the user, wherein the at least one modified attribute of the user is associated with at least one attribute of an occupational task, and wherein the server computing device is configured to:

receive data associated with the user, wherein the data comprises the at least one modified attribute of the user and the at least one attribute of the occupational task;

access a database comprising data associated with one or more exercises associated with the at least one modified attribute of the user and the at least one attribute of the occupational task;

generate, via an artificial intelligence engine, the treatment plan comprising at least one exercise of the one or more exercises associated with the at least one modified attribute of the first user and the at least one attribute of the occupational task, wherein the artificial intelligence engine generates the treatment plan comprising the at least one exercise based on the data associated with the user and the data associated with the one or more exercises.

Clause 2. The computer-implemented system of any clause herein, wherein the server computing device is further configured to:

receive, based on injury information associated with the user, one or more target recovery outcomes for the user; and based on (i) the one or more target recovery outcomes for the user, (ii) the data associated with the user, and (iii) the data associated with the one or more exercises, generate, via the artificial intelligence engine, the treatment plan comprising the at least one exercise.

Clause 3. The computer-implemented system of any clause herein, wherein the server computing device is further configured to:

receive injury information associated with the user;

based on the injury information, determine, via the artificial intelligence engine, one or more recovery outcomes for the user; and based on (i) the one or more recovery outcomes for the user, (ii) the data associated with the user, and (iii) the data associated with the one or more exercises, generate, via the artificial intelligence engine, the treatment plan comprising the at least one exercise.

Clause 4. The computer-implemented system of any clause herein, wherein the one or more recovery outcomes comprises a target recovery time, a target recovery cost for the user, a target recovery cost for the insurance provider, or some combination thereof.

Clause 5. The computer-implemented system of any clause herein, wherein the server computing device is further configured to estimate, via the artificial intelligence engine, when the user performing the treatment plan would be capable of performing the occupational task to a targeted performance level.

Clause 6. The computer-implemented system of any clause herein, wherein the at least one modified attribute of the user comprises recovery information, personal information, performance information, measurement information, incentive information, cost information, user satisfaction level information, or some combination thereof.

Clause 7. The computer-implemented system of any clause herein, wherein:

the recovery information comprises a target rate of recovery, a target state of recovery, a target recovery outcome, a target recovery satisfaction level, or some combination thereof, the personal information comprises an age, a weight, a gender, a race, an ethnicity, a marital status, an income, an education level, a height, a body mass index, a medical condition, a familial medical history, an injury, a medical procedure, a drug prescription, nutritional supplement, and illicit drug history, or some combination thereof, the performance information comprises an elapsed time for using the treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, a description of the treatment plan associated with the treatment apparatus, or some combination thereof, the measurement information comprises a vital sign, a respiration rate, a heartrate, a temperature, blood glucose, or some combination thereof, and the incentive information comprises information about an awardable product, object, activity, accolade, title, discount, coupon, money, cryptocurrency, or some combination thereof.

Clause 8. The computer-implemented system of any clause herein, wherein the at least one attribute of the occupational task of the user comprises requirements associated with stamina, strength, flexibility, pliability, range of motion, sustained attention, speech, height, weight, limb use, body mass index, or some combination thereof.

Clause 9. The computer-implemented system of any clause herein, wherein the database comprises a plurality of cohorts of data associated with exercises associated with modified attributes of users and attributes of occupational tasks, and the computing device is further configured to:

by at least matching the data associated with the one or more exercises with the data pertaining the exercises, select a cohort from the plurality of cohorts of data.

Clause 10. The computer-implemented system of any clause herein, wherein the server computing device is further configured to, based on the treatment plan and while the user uses the treatment apparatus, control the treatment apparatus.

Clause 11. A computer-implemented method for generating a treatment plan to modify at least one attribute of a user, wherein the at least one attribute of the user is associated with at least one attribute of an occupational task, wherein method comprises:

receiving data associated with the user, wherein the data comprises at least one modified attribute of the user and the at least one attribute of the occupational task;

accessing a database comprising data associated with one or more exercises associated with the at least one modified attribute of the user and the at least one attribute of the occupational task; and generating, via an artificial intelligence engine, the treatment plan comprising at least one exercise of the one or more exercises associated with the at least one modified attribute of the user and the at least one attribute of the occupational task, wherein the artificial intelligence engine generates the treatment plan comprising the at least one exercise based on the data associated with the user and the data associated with the one or more exercises.

Clause 12. The computer-implemented method of any clause herein, further comprising:

receiving, based on injury information associated with the user, one or more target recovery outcomes for the user; and based on (i) the one or more target recovery outcomes for the user, (ii) the data associated with the user, and (iii) the data associated with the one or more exercises, generating, via the artificial intelligence engine, the treatment plan comprising the at least one exercise.

Clause 13. The computer-implemented method of any clause herein, further comprising:

receiving injury information associated with the user;

based on the injury information, determining, via the artificial intelligence engine, one or more recovery outcomes for the user; and based on (i) the one or more recovery outcomes for the user, (ii) the data associated with the user, and (iii) the data associated with the one or more exercises, generating, via the artificial intelligence engine, the treatment plan comprising the at least one exercise.

Clause 14. The computer-implemented method of any clause herein, wherein the one or more recovery outcomes comprises a target recovery time, a target recovery cost for the user, a target recovery cost for the insurance provider, or some combination thereof.

Clause 15. The computer-implemented method of any clause herein, wherein the computing device is further configured to estimate, via the artificial intelligence engine, when the user performing the treatment plan would be capable of performing the occupational task to a targeted performance level.

Clause 16. The computer-implemented method of any clause herein, wherein the at least one modified attribute of the user comprises recovery information, personal information, performance information, measurement information, incentive information, cost information, user satisfaction level information, or some combination thereof.

Clause 17. The computer-implemented method of any clause herein, wherein:

the recovery information comprises a target rate of recovery, a target state of recovery, a target recovery outcome, a target recovery satisfaction level, or some combination thereof, the personal information comprises an age, a weight, a gender, a race, an ethnicity, a marital status, an income, an education level, a height, a body mass index, a medical condition, a familial medical history, an injury, a medical procedure, a drug prescription, nutritional supplement, and illicit drug history, or some combination thereof, the performance information comprises an elapsed time for using the treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, a description of the treatment plan associated with the treatment apparatus, or some combination thereof, the measurement information comprises a vital sign, a respiration rate, a heartrate, a temperature, blood glucose, or some combination thereof, and the incentive information comprises information about an awardable product, object, activity, accolade, title, discount, coupon, money, cryptocurrency, or some combination thereof.

Clause 18. The computer-implemented method of any clause herein, wherein the at least one attribute of the occupational task of the user comprises requirements associated with stamina, strength, flexibility, pliability, range of motion, sustained attention, speech, height, weight, limb use, body mass index, or some combination thereof.

Clause 19. A tangible, non-transitory computer-readable medium storing instructions for generating a treatment plan to modify at least one attribute of a user, wherein the at least one attribute of the user is associated with at least one attribute of an occupational task, wherein a processing device executes the instructions to:

receive data associated with the user, wherein the data comprises at least one modified attribute of the user and the at least one attribute of the occupational task;

access a database comprising data associated with one or more exercises associated with the at least one modified attribute of the user and the at least one attribute of the occupational task;

generate, via an artificial intelligence engine, the treatment plan comprising at least one exercise of the one or more exercises associated with the at least one modified attribute of the first user and the at least one attribute of the occupational task, wherein the artificial intelligence engine generates the treatment plan comprising the at least one exercise based on the data associated with the user and the data associated with the one or more exercises.

Clause 20. The computer-readable medium of any clause herein, wherein the processing device is further configured to:

receive, based on injury information associated with the user, one or more target recovery outcomes for the user; and based on (i) the one or more target recovery outcomes for the user, (ii) the data associated with the user, and (iii) the data associated with the one or more exercises, generate, via the artificial intelligence engine, the treatment plan comprising the at least one exercise.

The above discussion is meant to be illustrative of the principles and various embodiments of the present disclosure. Numerous variations and modifications will become apparent to those skilled in the art once the above disclosure is fully appreciated. It is intended that the following clauses be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A computer-implemented system, comprising:

a treatment apparatus configured to be manipulated by a user while the user performs a treatment plan;

a patient interface associated with the user; and a server computing device configured to generate the treatment plan that includes at least one modified attribute of the user, wherein the at least one modified attribute of the user is associated with at least one attribute of an occupational task, and wherein the server computing device is configured to:

receive data associated with the user, wherein the data comprises the at least one modified attribute of the user and the at least one attribute of the occupational task;

access a database comprising data associated with one or more exercises associated with the at least one modified attribute of the user and the at least one attribute of the occupational task;

generate, via an artificial intelligence engine, the treatment plan comprising at least one exercise of the one or more exercises associated with the at least one modified attribute of the first user and the at least one attribute of the occupational task, wherein the artificial intelligence engine generates the treatment plan comprising the at least one exercise based on the data associated with the user and the data associated with the one or more exercises; and predict, via the artificial intelligence engine, an estimate of time for how long the user needs to perform the treatment plan to be capable of performing the occupational task to a targeted performance level, wherein the treatment plan includes first operating settings of the treatment apparatus for a first portion of the estimate of time and second operating settings of the treatment apparatus for a second portion of the estimate of time.

2. The computer-implemented system of claim 1, wherein the server computing device is further configured to:

receive, based on injury information associated with the user, one or more target recovery outcomes for the user; and based on (i) the one or more target recovery outcomes for the user, (ii) the data associated with the user, and (iii) the data associated with the one or more exercises, generate, via the artificial intelligence engine, the treatment plan comprising the at least one exercise.

3. The computer-implemented system of claim 1, wherein the server computing device is further configured to:

receive injury information associated with the user;

based on the injury information, determine, via the artificial intelligence engine, one or more recovery outcomes for the user; and based on (i) the one or more recovery outcomes for the user, (ii) the data associated with the user, and (iii) the data associated with the one or more exercises, generate, via the artificial intelligence engine, the treatment plan comprising the at least one exercise.

4. The computer-implemented system of claim 3, wherein the one or more recovery outcomes comprises a target recovery time, a target recovery cost for the user, a target recovery cost for the insurance provider, or some combination thereof.

5. The computer-implemented system of claim 1, wherein the at least one modified attribute of the user comprises recovery information, personal information, performance information, measurement information, incentive information, cost information, user satisfaction level information, or some combination thereof.

6. The computer-implemented system of claim 5, wherein:

the recovery information comprises a target rate of recovery, a target state of recovery, a target recovery outcome, a target recovery satisfaction level, or some combination thereof, the personal information comprises an age, a weight, a gender, a race, an ethnicity, a marital status, an income, an education level, a height, a body mass index, a medical condition, a familial medical history, an injury, a medical procedure, a drug prescription, nutritional supplement, and illicit drug history, or some combination thereof, the performance information comprises an elapsed time for using the treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, a description of the treatment plan associated with the treatment apparatus, or some combination thereof, the measurement information comprises a vital sign, a respiration rate, a heartrate, a temperature, blood glucose, or some combination thereof, and the incentive information comprises information about an awardable product, object, activity, accolade, title, discount, coupon, money, cryptocurrency, or some combination thereof.

7. The computer-implemented system of claim 1, wherein the at least one attribute of the occupational task of the user comprises requirements associated with stamina, strength, flexibility, pliability, range of motion, sustained attention, speech, height, weight, limb use, body mass index, or some combination thereof.

8. The computer-implemented system of claim 1, wherein the database comprises a plurality of cohorts of data associated with exercises associated with modified attributes of users and attributes of occupational tasks, and the computing device is further configured to:

by at least matching the data associated with the one or more exercises with the data pertaining the exercises, select a cohort from the plurality of cohorts of data.

9. The computer-implemented system of claim 1, wherein the server computing device is further configured to, based on the treatment plan and while the user uses the treatment apparatus, control the treatment apparatus.

10. A computer-implemented method for generating a treatment plan to modify at least one attribute of a user, wherein the at least one attribute of the user is associated with at least one attribute of an occupational task, wherein method comprises:

receiving data associated with the user, wherein the data comprises at least one modified attribute of the user and the at least one attribute of the occupational task;

accessing a database comprising data associated with one or more exercises associated with the at least one modified attribute of the user and the at least one attribute of the occupational task;

generating, via an artificial intelligence engine, the treatment plan comprising at least one exercise of the one or more exercises associated with the at least one modified attribute of the user and the at least one attribute of the occupational task, wherein the artificial intelligence engine generates the treatment plan comprising the at least one exercise based on the data associated with the user and the data associated with the one or more exercises; and predicting, via the artificial intelligence engine, an estimate of time for how long the user needs to perform the treatment plan to be capable of performing the occupational task to a targeted performance level, wherein the treatment plan includes first operating settings of the treatment apparatus for a first portion of the estimate of time and second operating settings of the treatment apparatus for a second portion of the estimate of time.

11. The computer-implemented method of claim 10, further comprising:

receiving, based on injury information associated with the user, one or more target recovery outcomes for the user; and based on (i) the one or more target recovery outcomes for the user, (ii) the data associated with the user, and (iii) the data associated with the one or more exercises, generating, via the artificial intelligence engine, the treatment plan comprising the at least one exercise.

12. The computer-implemented method of claim 10, further comprising:

receiving injury information associated with the user;

based on the injury information, determining, via the artificial intelligence engine, one or more recovery outcomes for the user; and based on (i) the one or more recovery outcomes for the user, (ii) the data associated with the user, and (iii) the data associated with the one or more exercises, generating, via the artificial intelligence engine, the treatment plan comprising the at least one exercise.

13. The computer-implemented method of claim 12, wherein the one or more recovery outcomes comprises a target recovery time, a target recovery cost for the user, a target recovery cost for the insurance provider, or some combination thereof.

14. The computer-implemented method of claim 10, wherein the at least one modified attribute of the user comprises recovery information, personal information, performance information, measurement information, incentive information, cost information, user satisfaction level information, or some combination thereof.

15. The computer-implemented method of claim 14, wherein:

the recovery information comprises a target rate of recovery, a target state of recovery, a target recovery outcome, a target recovery satisfaction level, or some combination thereof, the personal information comprises an age, a weight, a gender, a race, an ethnicity, a marital status, an income, an education level, a height, a body mass index, a medical condition, a familial medical history, an injury, a medical procedure, a drug prescription, nutritional supplement, and illicit drug history, or some combination thereof, the performance information comprises an elapsed time for using the treatment apparatus, an amount of force exerted on a portion of the treatment apparatus, a range of motion achieved on the treatment apparatus, a movement speed of a portion of the treatment apparatus, an indication of a plurality of pain levels using the treatment apparatus, a description of the treatment plan associated with the treatment apparatus, or some combination thereof, the measurement information comprises a vital sign, a respiration rate, a heartrate, a temperature, blood glucose, or some combination thereof, and the incentive information comprises information about an awardable product, object, activity, accolade, title, discount, coupon, money, cryptocurrency, or some combination thereof.

16. The computer-implemented method of claim 10, wherein the at least one attribute of the occupational task of the user comprises requirements associated with stamina, strength, flexibility, pliability, range of motion, sustained attention, speech, height, weight, limb use, body mass index, or some combination thereof.

17. A tangible, non-transitory computer-readable medium storing instructions for generating a treatment plan to modify at least one attribute of a user, wherein the at least one attribute of the user is associated with at least one attribute of an occupational task, wherein a processing device executes the instructions to:

receive data associated with the user, wherein the data comprises at least one modified attribute of the user and the at least one attribute of the occupational task;

access a database comprising data associated with one or more exercises associated with the at least one modified attribute of the user and the at least one attribute of the occupational task;

generate, via an artificial intelligence engine, the treatment plan comprising at least one exercise of the one or more exercises associated with the at least one modified attribute of the first user and the at least one attribute of the occupational task, wherein the artificial intelligence engine generates the treatment plan comprising the at least one exercise based on the data associated with the user and the data associated with the one or more exercises; and predict, via the artificial intelligence engine, an estimate of time for how long the user needs to perform the treatment plan to be capable of performing the occupational task to a targeted performance level, wherein the treatment plan includes first operating settings of the treatment apparatus for a first portion of the estimate of time and second operating settings of the treatment apparatus for a second portion of the estimate of time.

18. The computer-readable medium of claim 17, wherein the processing device is further configured to:

receive, based on injury information associated with the user, one or more target recovery outcomes for the user; and based on (i) the one or more target recovery outcomes for the user, (ii) the data associated with the user, and (iii) the data associated with the one or more exercises, generate, via the artificial intelligence engine, the treatment plan comprising the at least one exercise.

* * * * *